US012768844B2

(12) United States Patent
Tsui et al.

(10) Patent No.: US 12,768,844 B2
(45) Date of Patent: Oct. 20, 2026

(54) METHODS FOR SYSTEMATICALLY ASSESSING LOCAL INFLAMMATION AND ACTIVE REPAIR

(71) Applicant: KEYINTEL MEDICAL INC., Toronto (CA)

(72) Inventors: Florence Wing Ling Tsui, Oakville (CA); Kenneth Phillip Henry Pritzker, Toronto (CA)

(73) Assignee: KEYINTEL MEDICAL INC., Toronto (CA)

( * ) Notice: Subject to any disclaimer, the term of this patent is extended or adjusted under 35 U.S.C. 154(b) by 588 days.

(21) Appl. No.: 18/035,549

(22) PCT Filed: Nov. 5, 2021

(86) PCT No.: PCT/CA2021/051582
§ 371 (c)(1),
(2) Date: May 5, 2023

(87) PCT Pub. No.: WO2022/094722
PCT Pub. Date: May 12, 2022

(65) Prior Publication Data

US 2024/0012009 A1 Jan. 11, 2024

Related U.S. Application Data

(60) Provisional application No. 63/109,893, filed on Nov. 5, 2020.

(51) Int. Cl.

| | |
|---|---|
| ***G01N 33/68*** | (2006.01) |
| ***A61K 31/4418*** | (2006.01) |
| ***A61K 31/496*** | (2006.01) |
| ***A61P 19/02*** | (2006.01) |
| ***A61P 29/00*** | (2006.01) |
| ***C07K 16/24*** | (2006.01) |

(52) U.S. Cl.
CPC ..... *G01N 33/6893* (2013.01); *A61K 31/4418* (2013.01); *A61K 31/496* (2013.01); *A61P 19/02* (2018.01); *A61P 29/00* (2018.01); *C07K 16/241* (2013.01); *C07K 16/244* (2013.01); *C07K 2317/76* (2013.01); *G01N 2333/5412* (2013.01); *G01N 2333/96494* (2013.01); *G01N 2800/065* (2013.01); *G01N 2800/102* (2013.01)

(58) Field of Classification Search
None
See application file for complete search history.

(56) References Cited

U.S. PATENT DOCUMENTS

2008/0085524 A1 4/2008 Lois
2011/0244489 A1 10/2011 Devarajan et al.
2013/0177923 A1 7/2013 Uttenthal et al.
2019/0330328 A1* 10/2019 Mann ................. A61K 39/3955
2020/0064357 A1* 2/2020 Cheng .................. C12Q 1/6883

FOREIGN PATENT DOCUMENTS

WO 2018/089693 A2 5/2018
WO 2022032397 A1 2/2022

OTHER PUBLICATIONS

Lin, A. et al. Lipocalin 2 links inflammation and ankylosis in the clinical overlap of inflammatory bowel disease (IBD) and ankylosing spondylitis (AS). Arthritis Research & Therapy, Mar. 18, 2020. vol. 22, Article 51. Retrieved from the internet: https://arthritis-research.biomedcentral.com/articles/10.1186/s13075-020-02149-4.

Turina, M.C. et al. Lessons to be learned from serum biomarkers in psoriasis and IBD—the potential role in SpA. Expert Review of Clinical Immunology, Oct. 21, 2016. vol. 14, No. 4, pp. 333-344. Retrieved from the Internet: https://www.tandfonline.com/doi/pdf/10.1080/1744555X2017.1244004.

Korkosz, M. et al. Sera of patients with axial spondyloarthritis (axSpA) enhance osteoclastogenic potential of monocytes isolated from healthy individuals. BMC Musculoskeletal Disorders, Dec. 6, 2018, vol. 19, Article 434. Retrieved from the Internet: https://bmcmusculoskeletdisord.biomedcentral.com/articles/10.1186/s12891-018-2356-4.

Stallhofer, J. et al. Lipocalin-2 Is a Disease Activity Marker in Inflammatory Bowel Disease Regulated by IL-17A, IL-22, and TNF-α and Modulated by IL23R Genotype Status. Inflammatory Bowel Disease, Oct. 2015, vol. 21, No. 10, pp. 2327-2340. Retrieved from the Internet: https://academic.oup.com/ibdjournal/article/21/10/2327/4644920.

De Bruyn, M. et al. Neutrophil Gelatinase B-associated Lipocalin and Matrix Metalloproteinase-9 Complex as a Surrogate Serum Marker of Mucosal Healing in Ulcerative Colitis. Inflammatory Bowel Disease, May 27, 2014. vol. 20, No. 7, pp. 1198-1207. Retrieved from the Internet: https://academic.oup.com/ibdjournal/article/20/7/1198/4579560.

Blas, R. et al. Interleukin-6 blockade with tocilizumab decrease metalloproteinase-9 activity in synovial fibroblasts stimulated with synovial fluids of patients with rheumatoid arthritits or spondyloarthritits. Annals of the Rheumatic Diseases, Jun. 15, 2017, vol. 76, pp. 1064-1065. Retrieved from the Internet: https://ard.bmj.com/content/76/ Suppl_2/1064.3.info.

Tsui, Florence W.L. et al. The role of LCN2 and LCN2-MMP9 in spondylitis radiographic development: gender and HLA-B27 status differences. Arthritis Research & Therapy, 2022, 24:164.

(Continued)

*Primary Examiner* — Blaine Lankford
(74) *Attorney, Agent, or Firm* — Smart & Biggar LP; Herman Cheung

(57) ABSTRACT

Methods of assessing, monitoring and/or predicting clinical disease activity, treatment response, disease progression, and/or active repair for chronic inflammatory disease such as axial spondyloarthritis are provided based on the level and/or pattern of LCN2, LCN2-MMP9 and/or OSM.

9 Claims, 35 Drawing Sheets

(56) References Cited

OTHER PUBLICATIONS

De Bruyn, M. et al. Serum Neutrophil Gelatinase B-associated Lipocalin and Matrix Metalloproteinase-9 Complex as a Surrogate Marker for Mucosal Healing in Patients with Crohn's Disease. Journal of Crohn's and Colitis, 2015, 1079-1087.
Rodrigues Manica, Santiago et al. Early Recognition and Treatment of Spondyloarthritis: A Timeless Challenge. Rheumatology, Jul. 2020, pp. 72-79.
Lin, Aifeng. Novel Insights in Ankylosing Spondylitis Pathogenesis Mouse and Human Studies. Thesis submitted in 2018. Institute of Medical Sciences, University of Toronto.
Tsui, Florence W.L. et al. Serial Lipocalin 2 and Oncostatin M levels reflect inflammation staus and treatment response in axial spondyloarthritis. Arthritis Research & Therapy, 2021, 23:141.
Pritzker, Kenneth P. H. et al. Reducing Diagnostic Delay in Axial Spondyloarthritis: Could Lipocalin 2 Biomarkesrs Help? Rheumato, 2024, vol. 4, pp. 203-208.
Lin, Aifeng Novel Insights in Ankylosing Spondylitis Pathogenesis: Mouse and Human Studies. Thesis submitted in 2018, University of Toronto.

* cited by examiner cut-offs: ┆ L (150ng/ml); — — - LM (100ng/ml)

METHODS FOR SYSTEMATICALLY ASSESSING LOCAL INFLAMMATION AND ACTIVE REPAIR

RELATED APPLICATION

This disclosure claims benefit of U.S. Provisional Patent Application Ser. No. 63/109,893 filed Nov. 5, 2020, incorporated herein by reference in its entirety.

FIELD

The disclosure pertains to biomarkers and methods for assessing blood, serum, or plasma samples of subjects with or suspected of having chronic inflammatory disease such as axial spondyloarthritis (axSpA; also known as axial spondylitis or axial spondyloarthropathy) for clinical disease activity such as continuing inflammation, permitting monitoring clinical disease activity, treatment response, disease progression and/or active repair, or predicting potential disease progression and/or treatment response. The disclosure also pertains to biomarkers and methods for assessing, for example, blood, serum, or plasma samples of subjects with or suspected of having chronic inflammatory disease such as axial spondyloarthritis for developing inflammatory bowel diseases. The disclosure also pertains to biomarkers and methods for assessing blood, serum, or plasma samples of subjects with or suspected of having chronic inflammatory disease such as inflammatory bowel diseases for developing axial spondyloarthritis.

INTRODUCTION

Radiographic axial spondyloarthritis (r-axSpA; also known as ankylosing spondylitis (AS)), a subgroup of axial spondyloarthritis (axSpA), is a progressive debilitating disease which starts in young adults and proceeds through most of the lifespan. Males are preferentially affected. The distinctive features include sacroiliac joint (SIJ) and axial joint inflammation which precedes neo-ossification at previous inflammatory sites (Dakwar E, et al. 2008). r-axSpA is a heterogeneous and complex disease with a strong genetic component. Aside from the robust HLA-B27 genetic marker association with r-axSpA, genome-wide association studies (GWAS) have identified at least 48 r-axSpA non-major histocompatibility complex (MHC) immune-related loci (Ellinghaus D, et al. 2016). Yet the pathogenesis of r-axSpA is not entirely genetically determined. Environmental effects such as microbial factors, as implicated in reactive arthritis (ReA), might serve as a disease trigger (Kim T H, et al. 2005). To-date, there is no available model which adequately characterizes the biological determinants for the development of axSpA.

There are two central challenging aspects in the management of r-axSpA. First, there is a lack of informative serological markers to assess clinical disease activity and treatment response to ongoing local spinal and/or SIJ inflammation. Nonsteroidal anti-inflammatory drugs (NSAIDs) are the first-line drug treatment for r-axSpA patients with symptomatic disease (Song I H, et al. 2008). Patients with an inadequate clinical response to NSAIDs are candidates to receive biologics such as tumor necrosis factor alpha (TNF-alpha) inhibitors (TNFi). Current parameters used to evaluate treatment effectiveness include the Bath Ankylosing Spondylitis Disease Activity Index (BASDAI; a patient-reported outcome) and serum C-reactive protein (CRP), which is a nonspecific indicator of systemic inflammation.

CRP, a serum marker of systemic inflammation, is elevated in approximately only 30% of r-axSpA patients with active disease (Benhamou M, et al. 2010) and has been correlated poorly with clinical response to biologic treatments (De Vries M K, et al. 2009). In non-radiographic spondyloarthritis (nr-axSpA), a positive magnetic resonance imaging (MRI) or an elevated CRP level appeared to be good predictors to adalimumab treatment response for patients that would have advanced disease (Sieper J, et al. 2012). The r-axSpA disease activity score (ASDAS) incorporates some core elements of the BASDAI with the CRP (Machado P, et al. 2011). Better serum biomarkers, particularly biomarkers that are informative of local inflammation are a widely recognized need to provide personalized management of these patients (Brown M A, et al. 2020; Turina M C, et al. 2017). Secondly, there are shortcomings in current therapeutic options. TNFi therapies are highly effective in controlling symptoms such as back pain, working as effective analgesics independent of anti-inflammatory effects (Wu Q, et al. 2015) and improving quality of life of many r-axSpA patients. However, this treatment is not curative as symptoms often recurwhen biologics are discontinued, and the disease progresses in some patients while on these therapies. Additionally, at least 30% of r-axSpA patients are not responsive to, or are intolerant of, TNFi (Glinborg B, et al. 2013). Biomarkers which reflect treatment response could aid clinicians in better disease management and reduce health-care costs for this disease.

One of the most common extra-articular manifestations associated with r-axSpA is inflammatory bowel diseases (IBD). IBD is a group of chronic inflammatory disorders in the gut most prominent of which are ulcerative colitis and Crohn's disease that have distinctive and different pathology. Patients have symptoms such as diarrhea, abdominal pain, and weight loss, which affect dramatically their quality of life and productivity. A significant clinical overlap exists between IBD and r-axSpA. Up to one third of IBD patients develop articular disease featuring r-axSpA and 4-10% of the patients have concurrent r-axSpA (Bandinelli F, et al. 2016; Chan J et al, 2018; Kelly O B et al, 2019). Conversely, approximately 10% of r-axSpA cohorts are identified with clinical IBD (Rudwaleit M, et al. 2006). Importantly, there is frequently asymptomatic subclinical gut inflammation in 40-60% of patients with, r-axSpA both macroscopically and microscopically (Bandinelli F, et al. 2016; Chan J et al, 2018; Kelly O B et al, 2019). Furthermore, remission of joint inflammation is commonly associated with remission of gastrointestinal inflammation. Nevertheless, persistence of peripheral joint inflammation is usually associated with persistence of bowel involvement (Cuvelier C et al., 1987; Cuvelier C A et al., 1995).

Currently, there are no reliable biomarkers which can predict the development of r-axSpA in IBD patients, nor predict the development of IBD in r-axSpA patients. Currently, most but not all of these patients respond to TNFi therapy at least partially. Next generation biologics are emerging, but inhibitors which work for r-axSpA patients have been shown not to be as effective for IBD patients (e.g., IL17i, IL12/23i, & IL23i; Verstock B, et al. 2018; Agollo M C, et al. 2019; Davies S C, et al. 2019). The use of these inhibitors in patients with both IBD and r-axSpA could be problematic. Distinctive biomarkers would help the health-care providers in their selection of optimal therapy for these patients.

Lipocalin 2 (LCN2; also called neutrophil gelatinase B-associated lipocalin [NGAL] because of its original detection in neutrophil granules) was first recognized to be released by the liver in response to bacterial-triggered acute infections (Singh V, et al. 2016). LCN2 is produced in multiple cell types in different tissues (including gut, joint, liver, and adipose tissue) and has both pro- and anti-inflammatory properties which are context-dependent (Moschen A R, et al. 2017; Abella V, et al. 2015; Veeriah V, et al. 2016; Conde J, et al. 2016; Stallhofer J, et al. 2015). Elevated serum levels of LCN2 have been reported in patients with IBD (Stallhofer J, et al. 2015) and psoriasis (Ataseven A, et al. 2014). In patients with concurrent r-axSpA and IBD, elevated level of LCN2 was associated with coexisting ankylosis and gut inflammation (Lin A, et al. 2020).

Matrix metalloproteinase-9 (MMP9) plays a role in the degradation of extracellular matrix during early phase of inflammation and remodeling extracellular matrix thereafter (Yan L. et al, 2001). The complexation of MMP9 with LCN2 increases the stability of MMP9, which results in higher gelatinolytic activity of MMP9 in vitro (Fernandez et al, 2005). Aberrant levels of LCN2-MMP9 have been detected in patients with inflammatory diseases and rheumatic diseases (de Bruyn M, et al. 2014; de Bruyn M, et al. 2015; Gupta K, et al. 2007). Recently, LCN2-MMP9 has been shown as a surrogate marker for mucosal healing observed endoscopically in patients with Crohn's disease and ulcerative colitis (de Bruyn M, et al. 2014; de Bruyn M, et al. 2015).

Oncostatin M (OSM) has known involvement in IBD patients (Verstockt S, et al. 2019). OSM is also produced in multiple cells in different tissues (Kerfoot S M, et al. 2001; Richards C D 2013). OSM has known functions in inflammation and bone remodeling (West N R, et al. 2018; Walker E C, et al. 2010), as well as infection and injury.

SUMMARY

The inventors have identified several biomarker parameters in a subject having chronic inflammatory disease, such as axial spondyloarthritis (axSpA) or inflammatory bowel disease, that are associated with clinical disease activity such as local inflammation activity, treatment response and/or disease progression such as activity reflecting active repair following inflammation, favoring progression to joint fibrosis and ankylosis. Specifically, the inventors have identified key patterns of biomarker levels that can be used to assess inflammatory activity, monitor clinical disease activity, treatment response, disease progression, and/or active repair, as well as to predict disease progression and/or treatment response. This could help guide physicians in implementing personalized disease management in subjects with chronic inflammatory diseases such as axial spondyloarthritis and inflammatory bowel disease.

The disclosure provides in an aspect, methods for assessing inflammatory activity, monitoring disease progression, clinical disease activity, treatment response, and/or active repair, and/or predicting disease progression and/or treatment response in a subject with or suspected of having a chronic inflammatory disease such as axial spondyloarthritis.

One aspect of the present disclosure is a method for monitoring clinical disease activity, treatment response, disease progression, active repair, and/or predicting risk of developing a disease in a subject having or suspected of having a chronic inflammatory disease such as axSpA or inflammatory bowel disease, the method comprising:

measuring in vitro a level of lipocalin2 (LCN2), a level of LCN2-Matrix metallopeptidase 9 heterodimer (LCN2-MMP9), and/or a level of oncostatin M (OSM) in a sample obtained from the subject; and comparing the measured level of LCN2, LCN2-MMP9, and/or OSM to level in a previous sample and/or one or more reference profiles;

wherein a differential in the measured level of LCN2, LCN2-MMP9, and/or OSM compared to the previous sample, a differential in the measured level of LCN2, LCN2-MMP9, and/or OSM compared to the one or more reference profiles, or a pattern (e.g. persistence or transience) of the measured level of LCN2, LCN2-MMP9, and/or OSM similar to one or more reference profiles, is indicative of clinical disease activity, disease progression, treatment response, and/or active repair.

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM similar to one or more reference profiles. In some embodiments, the pattern is persistent elevation of the measured level of LCN2, LCN2-MMP9, and/or OSM similar to one or more reference profiles. In some embodiments, the one or more reference profile is LCN2elevatedOSMnormal, LCN2elevatedOSMelevated, LCN2normalOSMelevated or LCN2normalOSMnormal, LCN2elevatedLCN2-MMP9normalOSMnormal, LCN2elevatedLCN2-MMP9elevatedOSMnormal, LCN2elevatedLCN2-MMP9normalOSMelevated, LCN2elevatedLCN2-MMP9elevatedOSMelevated, LCN2normalLCN2-MMP9elevatedOSMnormal, LCN2normalLCN2-MMP9elevatedOSMelevated, LCN2normalLCN2-MMP9normalOSMelevated, or LCN2normalLCN2-MMP9normalOSMnormal.

In some embodiments, the LCN2elevatedOSMnormal is LCN2 transient (LCN2tOSMn). In some embodiments, the LCN2elevatedOSMnormal is LCN2 persistent (LCN2pOSMn). In some embodiments, the LCN2elevatedOSMelevated is LCN2 transient OSM transient (LCN2tOSMt). In some embodiments, the LCN2elevatedOSMelevated is LCN2 persistent OSM transient (LCN2pOSMt). In some embodiments, the LCN2elevatedOSMelevated is LCN2 persistent OSM persistent (LCN2pOSMp). In some embodiments, the LCN2elevatedOSMelevated is LCN2 transient OSM persistent (LCN2tOSMp). In some embodiments, the LCN2normalOSMelevated is OSM transient (LCN2nOSMt). In some embodiments, the LCN2normalOSMelevated is OSM persistent (LCN2nOSMp). In some embodiments, the LCN2elevatedLCN2-MMP9normalOSMnormal is LCN2 transient (LCN2tLCN2-MMP9nOSMn). In some embodiments, the LCN2elevatedLCN2-MMP9normalOSMnormal is LCN2 persistent (LCN2pLCN2-MMP9nOSMn). In some embodiments, the LCN2elevatedLCN2-MMP9elevatedOSMnormal is LCN2 transient LCN-MMP9 transient (LCN2tLCN2-MMP9tOSMn). In some embodiments, the LCN2elevatedLCN2-MMP9elevatedOSMnormal is LCN2 transient LCN-MMP9 persistent (LCN2tLCN2-MMP9pOSMn). In some embodiments, the LCN2elevatedLCN2-MMP9elevatedOSMnormal is LCN2 persistent LCN-MMP9 transient (LCN2pLCN2-MMP9tOSMn). In some embodiments, the LCN2elevatedLCN2-MMP9elevatedOSMnormal is LCN2 persistent LCN-MMP9 persistent (LCN2pLCN2-MMP9pOSMn). In some embodiments, the LCN2elevatedLCN2-MMP9normalOSMelevated is LCN2 transient OSM transient (LCN2tLCN2-MMP9nOSMt). In some embodiments, the LCN2elevatedLCN2-MMP9normalOSMelevated is LCN2 transient OSM persistent (LCN2tLCN2-MMP9nOSMp). In some embodiments, the LCN2elevatedLCN2-MMP9normalOSMelevated is LCN2 persistent OSM transient (LCN2pLCN2-MMP9nOSMt). In some embodiments, the LCN2elevatedLCN2-MMP9normalOSMelevated is LCN2 persistent OSM persistent (LCN2pLCN2-MMP9nOSMp). In some embodiments, the LCN2elevatedLCN2-MMP9elevatedOSMelevated is LCN2 transient LCN2-MMP9 transient OSM transient (LCN2tLCN2-MMP9tOSMt). In some embodiments, the LCN2elevatedLCN2-MMP9elevatedOSMelevated is LCN2 transient LCN2-MMP9 persistent OSM transient (LCN2tLCN2-MMP9pOSMt). In some embodiments, the LCN2elevatedLCN2-MMP9elevatedOSMelevated is LCN2 transient LCN2-MMP9 transient OSM persistent (LCN2tLCN2-MMP9tOSMp). In some embodiments, the LCN2elevatedLCN2-MMP9elevatedOSMelevated is LCN2 transient LCN2-MMP9 persistent OSM persistent (LCN2tLCN2-MMP9pOSMp). In some embodiments, the LCN2elevatedLCN2-MMP9elevatedOSMelevated is LCN2 persistent LCN2-MMP9 transient OSM transient (LCN2pLCN2-MMP9tOSMt). In some embodiments, the LCN2elevatedLCN2-MMP9elevatedOSMelevated is LCN2 persistent LCN2-MMP9 transient OSM persistent (LCN2pLCN2-MMP9tOSMp). In some embodiments, the LCN2elevatedLCN2-MMP9elevatedOSMelevated is LCN2 persistent LCN2-MMP9 persistent OSM transient (LCN2pLCN2-MMP9pOSMt). In some embodiments, the LCN2elevatedLCN2-MMP9elevatedOSMelevated is LCN2 persistent LCN2-MMP9 persistent OSM persistent (LCN2pLCN2-MMP9pOSMp). In some embodiments, the LCN2normalLCN2-MMP9elevatedOSMnormal is LCN2-MMP9 transient (LCN2nLCN2-MMP9tOSMn). In some embodiments, the LCN2normalLCN2-MMP9elevatedOSMnormal is LCN2-MMP9 persistent (LCN2nLCN2-MMP9pOSMn). In some embodiments, the LCN2normalLCN2-MMP9elevatedOSMelevated is LCN2-MMP9 transient OSM transient (LCN2nLCN2-MMP9tOSMt). In some embodiments, the LCN2normalLCN2-MMP9elevatedOSMelevated is LCN2-MMP9 transient OSM persistent (LCN2nLCN2-MMP9tOSMp). In some embodiments, the LCN2normalLCN2-MMP9elevatedOSMelevated is LCN2-MMP9 persistent OSM transient (LCN2nLCN2-MMP9pOSMt). In some embodiments, the LCN2normalLCN2-MMP9elevatedOSMelevated is LCN2-MMP9 persistent OSM persistent (LCN2nLCN2-MMP9pOSMp). In some embodiments, the LCN2normalLCN2-MMP9normalOSMelevated is OSM transient (LCN2nLCN2-MMP9nOSMt). In some embodiments, the LCN2normalLCN2-MMP9normalOSMelevated is OSM persistent (LCN2nLCN2-MMP9nOSMp).

In some embodiments, the disease is axSpA. In some embodiments, the disease progression is or comprises sacroiliac joint (SIJ) structural deterioration with or without increased scores toward spinal joint fusion as assessed by, for example, an X-ray clinical index such as modified Stoke Ankylosing Spondylitis Spinal Score (mSASSS; van der Heijde et al. 2019).

In some embodiments, the disease is axSpA. In some embodiments, the disease is r-axSpA. In some embodiments, the disease is nr-axSpA. In some embodiments, a good treatment response is or comprises improvement of inflammatory back pain, and/or disease modification by partial or complete resolution of ongoing inflammation as indicated by a decrease or normalization of measured LCN2, LCN2-MMP9, and/or OSM levels. In some embodiments, a decreased measured level of LCN2, LCN2-MMP9, and/or OSM compared to the previous sample and/or the one or more reference profile is indicative of a good treatment response. In some embodiments, a lack of decrease or persistent elevation of measured level of LCN2, LCN2-MMP9, and/or OSM, is indicative of disease progression, such as sacroiliac joint deterioration.

In some embodiments, the subject is receiving a treatment optionally for axSpA, for example prior to obtaining the sample and after obtaining the previous sample. In some embodiments, the subject is receiving a treatment for axSpA. In some embodiments, the subject is receiving a treatment for r-axSpA. In some embodiments, the subject is receiving a treatment for nr-axSpA. In some embodiments, the sample is taken after initiation of treatment and the measured level of LCN2, LCN2-MMP9, and/or OSM is compared to a previous sample taken prior to the initiation of treatment. In some embodiments, an increased measured level of LCN2, LCN2-MMP9, and/or OSM compared to the previous sample and/orthe one or more reference profiles is indicative that the subject is not responding to the treatment. In some embodiments, a decrease in the measured level of LCN2, LCN2-MMP9, and/or OSM compared to the previous sample is indicative that the subject is responding to treatment.

Another aspect of the present disclosure is a method of treating a subject with or suspected of having a chronic inflammatory disease such as axial spondyloarthritis, the method comprising:

a) administering to the subject a suitable treatment, optionally an anti-inflammatory therapy, an anti-inflammatory agent, an anti-fibrotic therapy, or an anti-fibrotic agent, when a sample from the subject exhibits a lipocalin 2 (LCN2), LCN2-MMP9, and/or oncostatin M (OSM) elevation or pattern (e.g., persistence or transience) compared to a previous sample and/or one or more reference profiles; or b) i) monitoring clinical disease activity, treatment response, disease progression, and/or active repair in the subject according to a method described herein; and ii) administering to the subject a suitable treatment, optionally an anti-inflammatory therapy, an anti-inflammatory agent, an anti-fibrotic therapy, or an anti-fibrotic agent, when a sample from the subject exhibits an LCN2, LCN2-MMP9, and/or OSM elevation or pattern (e.g. persistence or transience) compared to a previous sample and/or one or more reference profiles, optionally wherein the suitable treatment is administered until the level of LCN2, LCN2-MMP9, and/or OSM is decreased or about normal.

In some embodiments, the pattern is transient elevation of the level of LCN2, LCN2-MMP9, and/or OSM compared to the previous sample and/or one or more reference profiles. In some embodiments, the pattern is persistent elevation of the level of LCN2, LCN2-MMP9, and/or OSM compared to the previous sample and/or one or more reference profiles. In some embodiments, the pattern is transient elevation of the measured level of LCN2, LCN2-MMP9, and/or OSM similar to one or more reference profiles. In some embodiments, the pattern is persistent elevation of the measured level of LCN2, LCN2-MMP9, and/or OSM similar to one or more reference profiles. In some embodiments, the suitable treatment is or comprises an anti-inflammatory agent. In some embodiments, the anti-inflammatory agent is or comprises a nonsteroidal anti-inflammatory drug (NSAID), a disease modifying anti-rheumatic drug (DMARD), a tumor necrosis factor alpha (TNF-alpha) inhibitor such as adalimumab, and/or an interleukin 17 inhibitor such as secukinumab. In some embodiments, the suitable treatment is an anti-inflammatory agent. In some embodiments, the anti-inflammatory agent is or comprises a TNF-alpha inhibitor. In some embodiments, the anti-inflammatory agent is or comprises a TNF-alpha inhibitor when the sample exhibits elevated level of LCN2, or elevated level of LCN2 and LCN2-MMP9, or elevated level of LCN2, LCN2-MMP9 and OSM compared to a previous sample and/or one or more reference profiles. In some embodiments, the TNF-alpha inhibitor comprises adalimumab, certolizumab, etanercept, golimumab, infliximab, or a combination thereof. In some embodiments, the anti-inflammatory agent lacks a TNF-alpha inhibitor. In some embodiments, the subject was previously receiving a TNF alpha inhibitor. In some embodiments, the anti-inflammatory agent is or comprises an interleukin 17 (IL-17) inhibitor. In some embodiments, the IL-17 inhibitor is or comprises secukinumab. In some embodiments, the sample exhibits LCN2normal persistent increased OSM and the subject is receiving anti-inflammatory treatment and the administering comprises administering an increased dosage of the anti-inflammatory agent or the anti-inflammatory agent administered is different from the anti-inflammatory treatment. In some embodiments, the suitable treatment is or comprises an anti-fibrotic therapy. In some embodiments, the anti-fibrotic therapy is or comprises inhibition of nonreceptor tyrosine kinases and/or receptor tyrosine kinases. In some embodiments, the anti-fibrotic therapy is or comprises inhibition of fibroblast proliferation, transforming growth factor beta stimulated collagen production, and/or fibrogenic mediators production. In some embodiments, the suitable treatment is or comprises an anti-fibrotic agent. In some embodiments, the anti-fibrotic agent is or comprises nintedanib or pirfenidone. In some embodiments, the anti-fibrotic agent is or comprises nintedanib. In some embodiments, the anti-fibrotic agent is or comprises pirfenidone. In some embodiments, the subject is clinically quiescent when the sample is taken. In some embodiments, the clinically quiescent subject does not exhibit symptoms of worsening back pain or flare up. In some embodiments, the subject is exhibiting back pain or back pain flare up. In some embodiments, the sample exhibits normal LCN2 and OSM and the subject exhibits back pain, thereby indicating a source of pain other than r-axSpA. In some embodiments, the method further comprises subjecting the subject to additional tests when the sample exhibits normal LCN2 and OSM indicative of a source of pain other than r-axSpA. In some embodiments, the sample is a blood, serum, or plasma sample. In some embodiments, the sample is a blood sample. In some embodiments, the sample is a serum sample. In some embodiments, the sample is a plasma sample. In some embodiments, the subject with axial spondyloarthritis has r-axSpA. In some embodiments, the subject has axSpA without or with coexisting inflammatory bowel disease. In some embodiments, the subject is also afflicted with inflammatory bowel disease. In some embodiments, the subject is recently diagnosed with r-axSpA Another aspect of the present disclosure is a method of assessing if a subject has chronic inflammation, the method comprising:

measuring in vitro a level of lipocalin2 (LCN2), a level of LCN2-MMP9, and/or a level of oncostatin M (OSM) in a sample obtained from the subject; and comparing the measured level of LCN2, LCN2-MMP9, and/or OSM to level in a previous sample and/or one or more reference profiles;

wherein a differential in the measured level of LCN2, LCN2-MMP9, and/or OSM compared to the previous sample, or a differential in the measured level of LCN2, LCN2-MMP9, and/or OSM compared to the one or more reference profiles, is indicative of ongoing chronic inflammation.

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles.

Another aspect of the present disclosure is a method for treating a subject with a chronic inflammatory disease, the method comprising:

a) administering to the subject a suitable treatment, optionally an anti-inflammatory therapy, an anti-inflammatory agent, an anti-fibrotic therapy, or an anti-fibrotic agent, when a sample from the subject exhibits a lipocalin 2 (LCN2), LCN2-MMP9 and/or oncostatin M (OSM) elevation compared to a previous sample and/or one or more reference profiles; or b) i) monitoring clinical disease activity, treatment response, disease progression, and/or active repair in the subject according to a method described herein; and ii) administering to the subject a suitable treatment, optionally an anti-inflammatory therapy, an anti-inflammatory agent, an anti-fibrotic therapy, or an anti-fibrotic agent, when a sample from the subject exhibits an LCN2, LCN2-MMP9, and/or OSM elevation or pattern (e.g., persistence or transience) compared to a previous sample and/or one or more reference profiles, optionally wherein the therapy or agent is administered until the level of LCN2, LCN2-MMP9, and/or OSM is decreased or about normal.

In some embodiments, the pattern is transient elevation of the level of LCN2, LCN2-MMP9, and/or OSM compared to the previous sample and/or one or more reference profiles. In some embodiments, the pattern is persistent elevation of the level of LCN2, LCN2-MMP9, and/or OSM compared to the previous sample and/or one or more reference profiles. In some embodiments, the chronic inflammatory disease is axSpA. In some embodiments, a good treatment response comprises improvement or resolve of inflammatory back pain, SIJ inflammation, persistent pain, and/or pain flare up frequency or intensity.

Another aspect of the present disclosure is a method for predicting risk of spinal ankylosis development in a subject with axSpA, comprising:

measuring in vitro a level of lipocalin2 (LCN2), a level of LCN2-MMP9 and/or a level of oncostatin M (OSM) in a sample obtained from the subject; and comparing the measured level of LCN2, LCN2-MMP9, and/or OSM to level in a previous sample and/or one or more reference profile;

wherein the subject having a pattern of measured level of LCN2, LCN2-MMP9, and/or OSM similar to a reference profile of LpLMp, LtLMp, LpLMt, LnLMpOp, or LpLMnOp has an increased risk of spinal ankylosis development.

Another aspect of the present disclosure is a method for predicting risk of spondyloarthritis development in a subject having inflammatory bowel disease (IBD), comprising:

measuring in vitro a level of lipocalin2 (LCN2), a level of LCN2-MMP9 and/or a level of oncostatin M (OSM) in a sample obtained from the subject; and comparing the measured level of LCN2, LCN2-MMP9, and/or OSM to levels in one or more reference profile;

wherein the subject having the measured level of LCN2, LCN2-MMP9, and/or OSM similar to a reference profile of LCN2elevatedOSMnormal, LCN2elevatedOSMelevated, LCN2-MMP9elevatedOSMnormal, and/or LCN2-MMP9elevatedOSMelevated has an increased risk of spondyloarthritis development;

wherein the subject having the measured level of LCN2, LCN2-MMP9, and/or OSM similar to a reference profile of a weight ratio of LCN2-MMP9:LCN2 (w/w) of greater than or about 1:1 has an increased risk of spondyloarthritis development; or wherein the subject having the measured level of LCN2, LCN2-MMP9, and/or OSM similar to a reference profile LCN2normalLCN2-MMP9normal and a weight ratio of LCN2-MMP9:LCN2 (w/w) of greater than or about 1:1 has an increased risk of spondyloarthritis development.

In some embodiments, the spondyloarthritis is axSpA.

Another aspect of the present disclosure is a method for predicting risk of spondyloarthritis such as axSpA, in a subject, comprising:

measuring in vitro a level of lipocalin2 (LCN2), a level of LCN2-MMP9, and/or a level of oncostatin M (OSM) in a sample such as a blood, serum, or plasma sample obtained from the subject; and comparing the measured level of LCN2, LCN2-MMP9, and/or OSM to level in a previous sample and/or one or more reference profiles;

wherein a differential in the measured level of LCN2, LCN2-MMP9, and/or OSM compared to the previous sample, a differential in the measured level of LCN2, LCN2-MMP9, and/or OSM compared to the one or more reference profiles, or a pattern (e.g. persistence or transience) of the measured level of LCN2, LCN2-MMP9, and/or OSM similar to the one or more reference profiles, is indicative of an increased risk of developing spondyloarthritis such as axSpA, and wherein the subject has or suspected of having chronic inflammatory disease such as inflammatory bowel diseases (IBD).

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, the subject having the measured level of LCN2, LCN2-MMP9, and/or OSM similar to a reference profile of LCN2elevatedLCN2-MMP9normalOSMnormal has an increased risk of developing axSpA. In some embodiments, the axial spondyloarthritis is r-axSpA.

Another aspect of the present disclosure is a method for predicting risk of developing inflammatory bowel diseases (IBD) in a subject, comprising:

measuring in vitro a level of lipocalin2 (LCN2), a level of LCN2-MMP9, and/or a level of oncostatin M (OSM) in a sample such as a blood, serum, or plasma sample obtained from the subject; and comparing the measured level of LCN2, LCN2-MMP9, and/or OSM to level in a previous sample and/or one or more reference profiles;

wherein a differential in measured level of LCN2, LCN2-MMP9, and/or OSM compared to the previous sample, a differential in the measured level of LCN2, LCN2-MMP9, and/or OSM compared to the one or more reference profiles, or a pattern (e.g. persistence or transience) of the measured level LCN2, LCN2-MMP9, and/or OSM similar to one or more reference profiles, is indicative of an increased risk of developing IBD, and wherein the subject has or suspected of having chronic inflammatory disease such as spondyloarthritis, optionally axSpA.

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, the chronic inflammatory disease is r-axSpA. In some embodiments, the chronic inflammatory disease is nr-axSpA, In some embodiments, the subject having the measured level of LCN2, LCN2-MMP9, and/or OSM similar to a reference profile of LCN2normalLCN2-MMP9elevated, LCN2normalLCN2-MMP9elevatedOSMnormal, LCN2normalLCN2-MMP9elevatedOSMelevated has an increased risk of developing IBD. In some embodiments, the subject having the measured level of LCN2, LCN2-MMP9, and/or OSM similar to a reference profile of LCN2elevatedlLCN2-MMP9elevatedOSMelevated has an increased risk of developing IBD. In some embodiments, the subject having the measured level of LCN2, LCN2-MMP9, and/or OSM similarto a reference profile of LCN2elevatedLCN2-MMP9elevatedOSMelevated has an increased risk of developing IBD. In some embodiments, the level of LCN2, LCN2-MMP9, and/or OSM is measured by enzyme-linked immunosorbent assay (ELISA).

Another aspect of the present disclosure is a method for providing a treatment plan for a subject having axial spondyloarthritis undergoing a treatment comprises: measuring in vitro concentration of lipocalin2 (LCN2) and concentration of LCN2-Matrix metallopeptidase 9 heterodimer (LCN2-MMP9) in a sample obtained from the subject;

determining the weight ratio of the concentration of LCN2 to the concentration of LCN2-MMP9 in the sample;

wherein if the weight concentration of LCN2 and LCN2-MMP9 are within normal limits, and the weight ratio of the concentration of LCN2 to the concentration of LCN2-MMP9 is between about 0.8 and about 1.2, it is indicative of the subject having disease activity fluctuation, and if it is indicative that the subject is having disease activity fluctuation, the treatment plan comprises administration of an alternative treatment.

The preceding section is provided by way of example only and is not intended to be limiting on the scope of the present disclosure and appended claims. Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DRAWINGS

Further objects, features and advantages of the disclosure will become apparent from the following detailed description taken in conjunction with the accompanying figures showing illustrative embodiments of the disclosure, in which:

FIG. 1A shows the detection of LCN2 and LCN2-MMP9 levels in axSpA patients with the involvement of LCN2 pathway alone. LCN2 and LCN2-MMP9 levels were compared in patients with normal OSM but persistent LCN2 elevation (LpOn, n=82) vs. transient LCN2 elevation (LtOn, n=41) vs. normal LCN2 (LnOn, n=62). One-way analysis of variance (ANOVA) followed by Bonferroni's multiple comparison test was used.

FIG. 1B shows the detection of LCN2, LCN2-MMP9, and OSM levels in axSpA patients with the involvement of OSM pathway alone. LCN2, LCN2-MMP9 and OSM levels were compared in patients with normal LCN2 but persistent OSM elevation (LnOp, n=24) vs. transient OSM elevation (LnOt, n=3). Student's t test was used.

FIG. 2A shows the detection of LCN2, LCN2-MMP9, and OSM levels in axSpA patients with persistently elevated level of LCN2, among those with both LCN2 and OSM pathways involved. LCN2, LCN2-MMP9, and OSM levels were compared in patients with persistent LCN2 and OSM elevation (LpOp, n=27) vs. those with persistent LCN2 and transient OSM elevation (LpOt, n=8). Student's t test was used.

FIG. 2B shows the detection of LCN2, LCN2-MMP9, and OSM levels in axSpA patients with the transiently elevated level of LCN2, among those with both LCN2 and OSM pathways involved. LCN2, LCN2-MMP9, and OSM levels were compared in patients with transient LCN2 and persistent OSM elevation (LtOp, n=22) vs. transient LCN2 and OSM elevation (LtOt, n=17). Student's t test was used.

Figure 6:
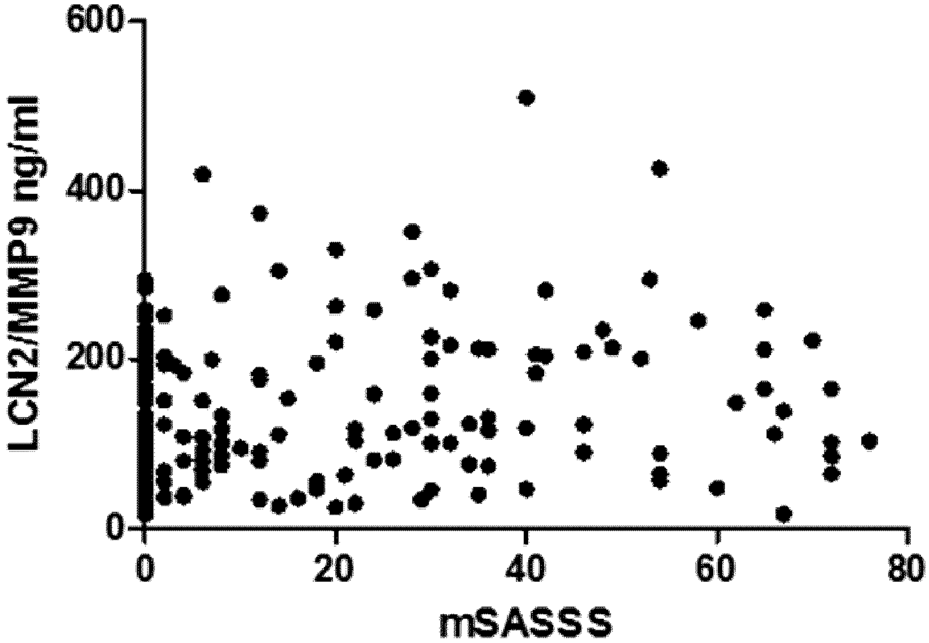

FIG. 6 shows the correlation of LCN2-MMP9 levels with mSASS scores. A positive correlation of mSASSS with the levels of LCN2-MMP9 of patients with axSpA (n=197) is established. Pearson's correlation coefficient test was used.

Figure 7:
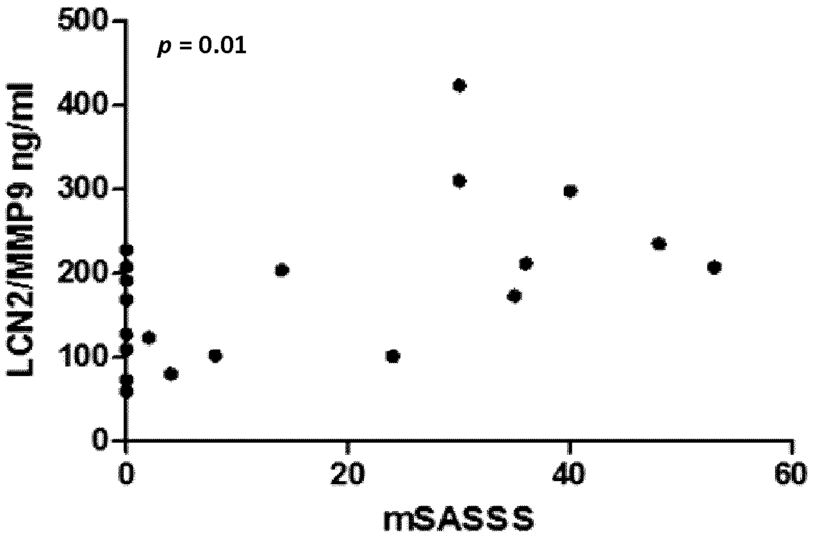

FIG. 7 shows the correlation of LCN2-MMP9 levels with mSASS scores in patients with persistent elevation of LCN2 and OSM (LpOp; n=20). Only LCN2-MMP9 levels but not LC2 levels were positively correlated with mSASSS in patients with LpOp (p=0.01). Pearson's correlation coefficient test was used.

Figure 8:
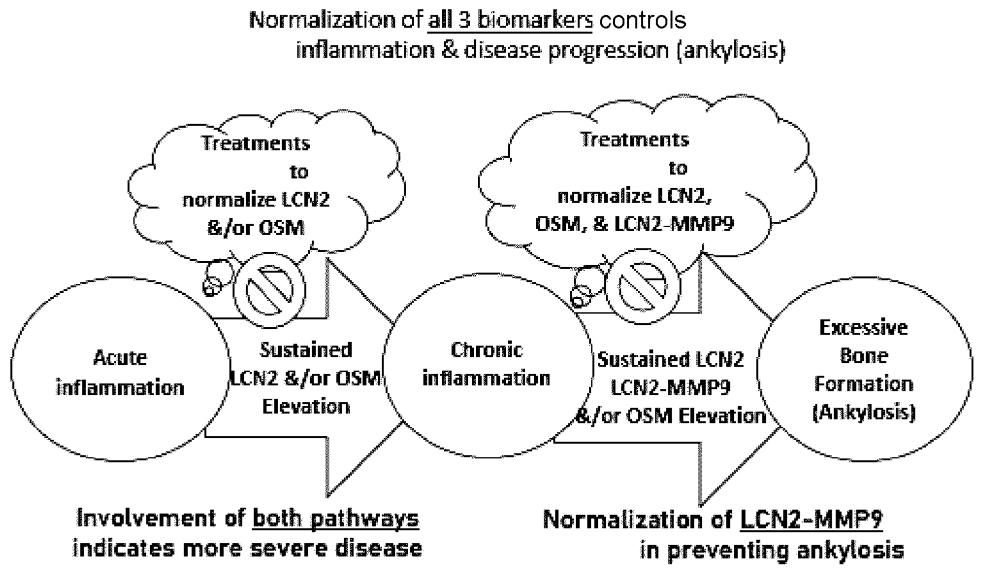

FIG. 8 shows a model describing the use of LCN2, LCN2-MMP9, and OSM for personalized disease management. During acute inflammation, prolonged LCN2 and/or OSM elevation leads to chronic inflammation. Normalized LCN2 and/or OSM can prevent the initiation of the disease. During chronic inflammation, persistent elevation of LCN2, LCN2-MMP9, and/or OSM promotes ankylosis progression. The use of corresponding treatments which can normalize the elevated biomarkers would enable personalized management of axSpA patients.

Figure 9:
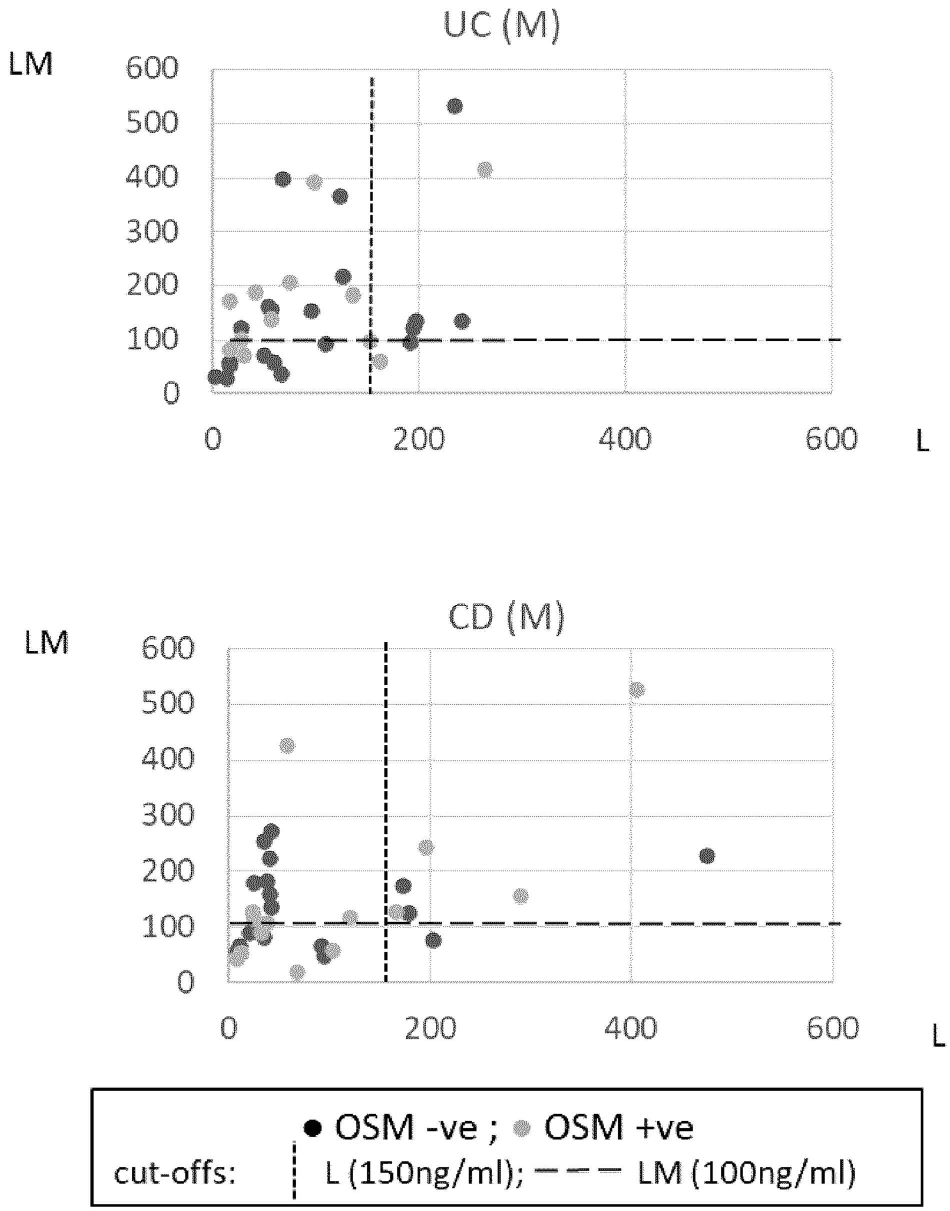

FIG. 9 shows LCN2 (L) and LCN2-MMP9 (LM) levels in ulcerative colitis (UC; top panel) and Crohn's disease (CD; bottom panel) male (M) patients with no detectable OSM (black dots) vs with detectable OSM (gray dots).

Figure 10:
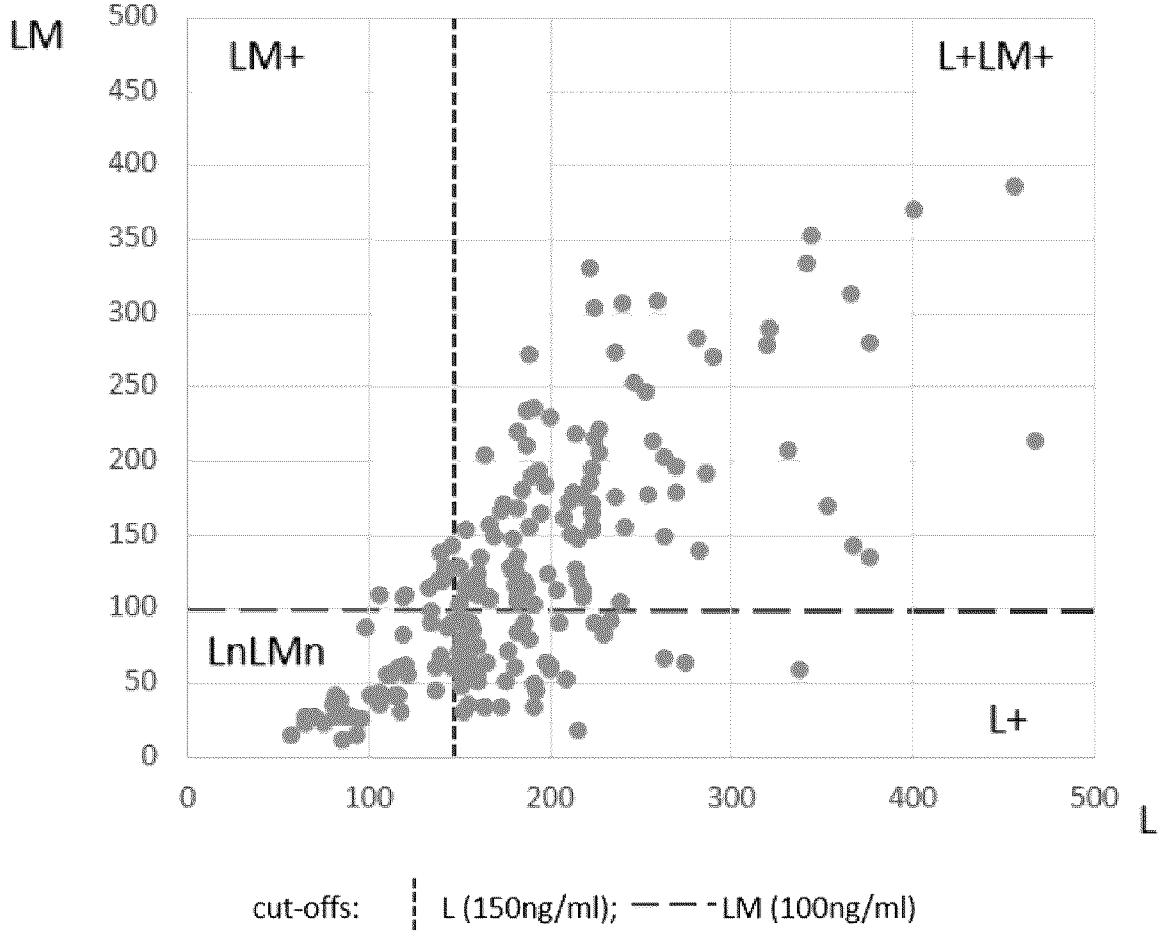

FIG. 10 shows LCN2 (L) and LCN2-MMP9 (LM) levels in axSpA patients with no detectable OSM. L (x-axis) and LM (y-axis) levels were measured in a single blood sample from each of the 190 axSpA patients. There are 3 patterns of L and/or LM elevation: L+ (22%), LM+(6%), L+LM+ (52%).

Figure 11A:
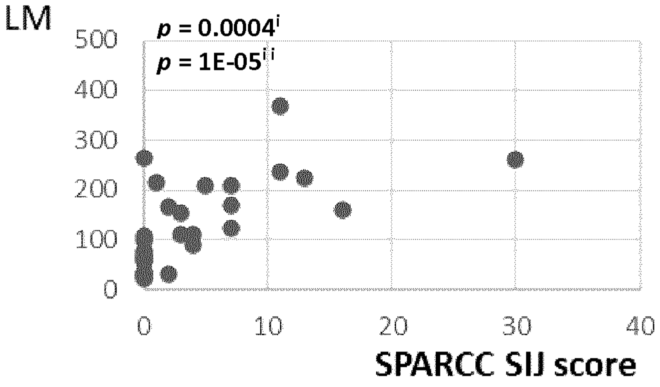
Figure 11A:
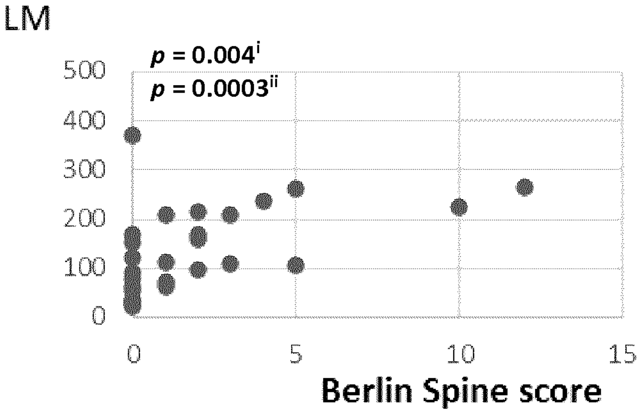

FIG. 11A shows the correlation of LM levels with SPARCC SIJ scores and Berlin Spine Scores in L+LM+ patients (n=16) and LnLMn patients (n=13) (total n=29). i) Pearson's correlation coefficient test and ii) Spearman's Rho correlation calculation were used to determine significance.

Figure 11B:
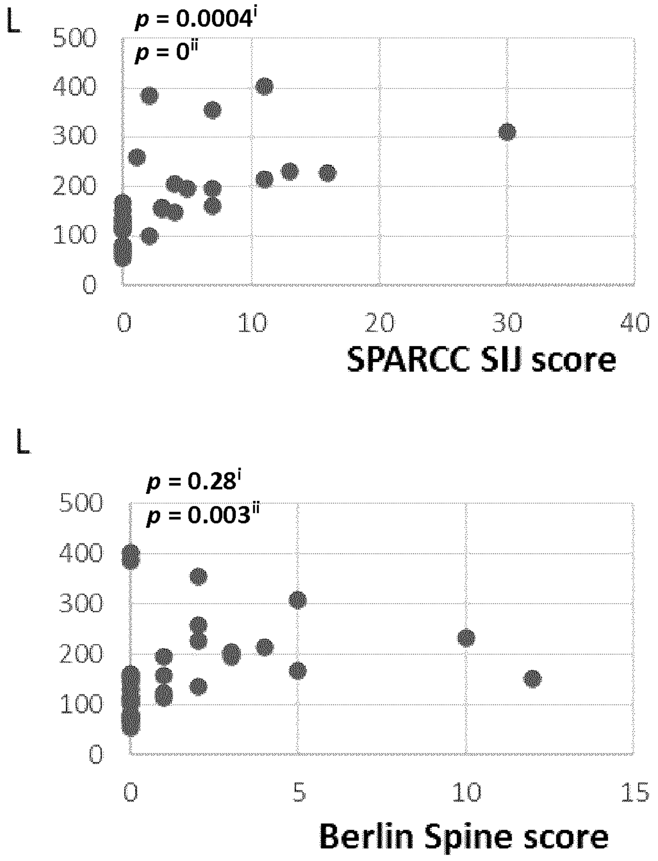

FIG. 11B shows the correlation of L levels with SPARCC SIJ scores and Berlin Spine Scores in L+LM+ and LnLMn patients (total n=29). i) Pearson's correlation coefficient test and ii) Spearman's Rho correlation calculation were used to determine significance.

Figure 11C:
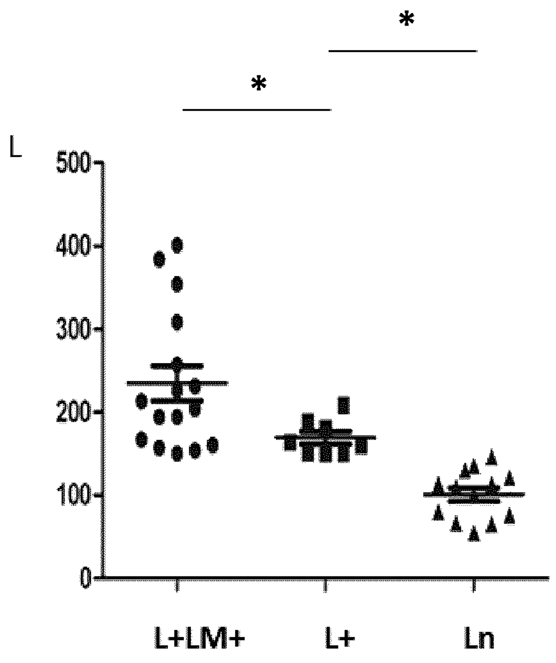

FIG. 11C shows that L levels in L+LM+ patients (n=16) are significantly higher than L levels in L+ (8) patients. One-way analysis of variance (ANOVA) including Tukey Honestly Significant Difference (HSD) were used to determine significance.

Figure 12A:
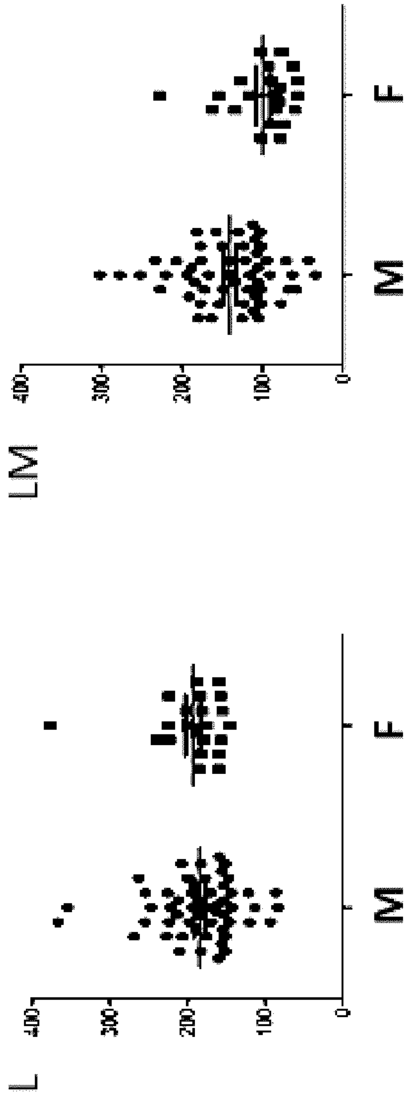

FIG. 12A shows gender differences in LCN2 (L) and LCN2-MMP9 (LM) patterns in r-axSpA patients with mSASSS<10. Female patients (n=22) have significantly lower LM levels compare to male patients (n=54). Independent Student's t tests were used to determine significance.

Figure 12B:
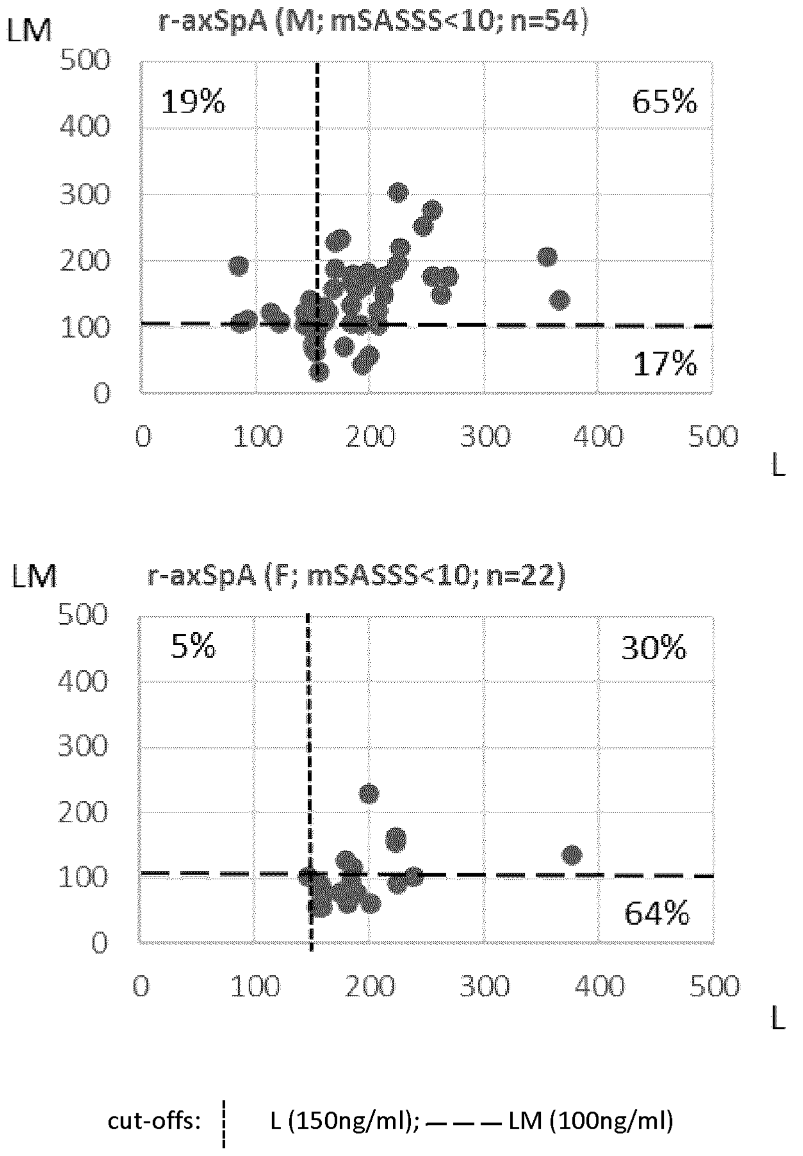

FIG. 12B shows gender differences in LCN2 (L) and LCN2-MMP9 (LM) patterns in r-axSpA patients with mSASSS<10. Pattern profiling of male vs female patients showed significant differences. 65% male patients are L+LM+ and 64% female patients are L+. $Chi^2$ test was used to determine significance.

Figure 12C:
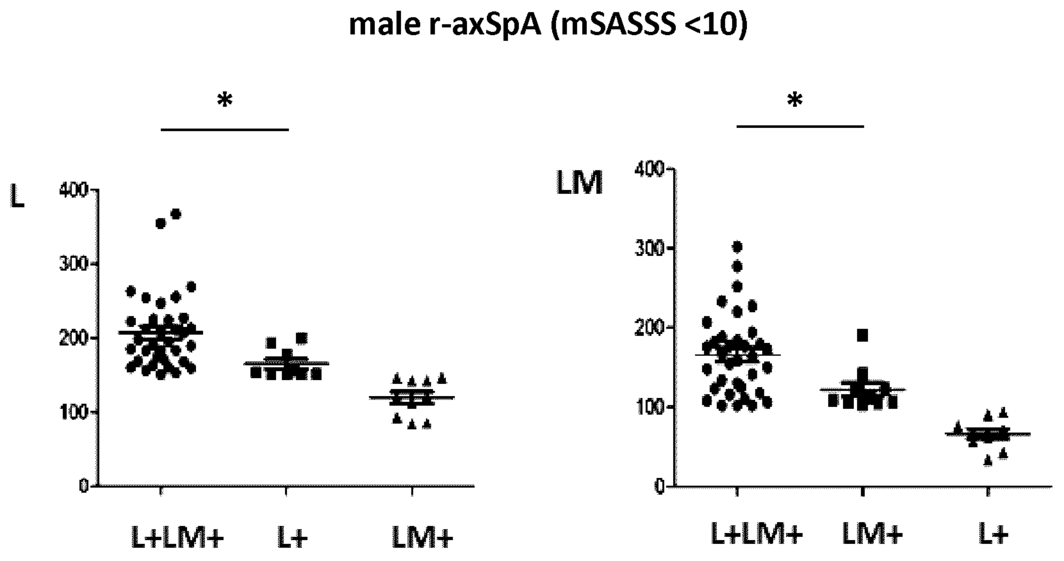

FIG. 12C shows LCN2 (L) and LCN2-MMP9 (LM) patterns in male r-axSpA patients with mSASSS<10. Significant quantitative difference in L and LM levels on comparing L levels in L+LM+ (n=35) vs L+ (n=9) male patients and LM levels in L+LM+ vs LM+ (n=10) male patients. One-way analysis of variance (ANOVA) including Tukey Honestly Significant Difference (HSD) were used to determine significance.

Figure 12D:
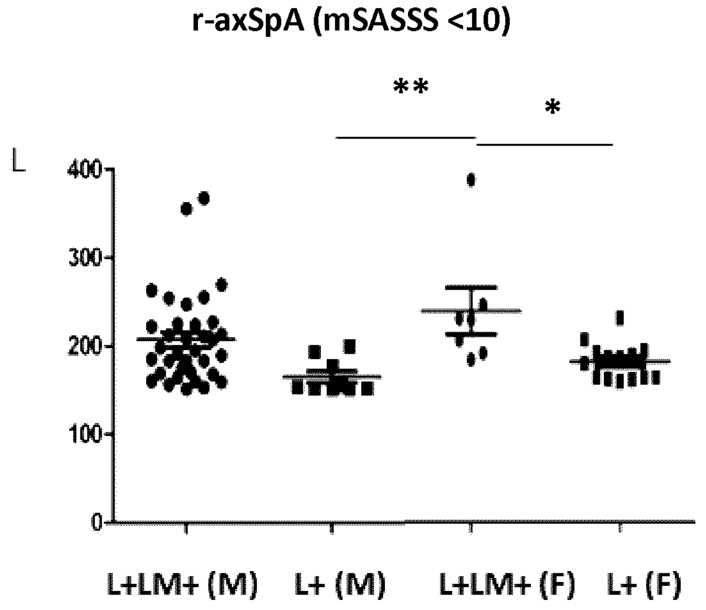

FIG. 12D shows gender differences in LCN2 (L) and LCN2-MMP9 (LM) patterns in r-axSpA patients with mSASSS<10. L levels in L+LM+ female patients (n=7) are higher than L levels in L+ patients (male [n=9] and female [n=14]). One-way analysis of variance (ANOVA) including Tukey Honestly Significant Difference (HSD) were used to determine significance.

Figure 13A:
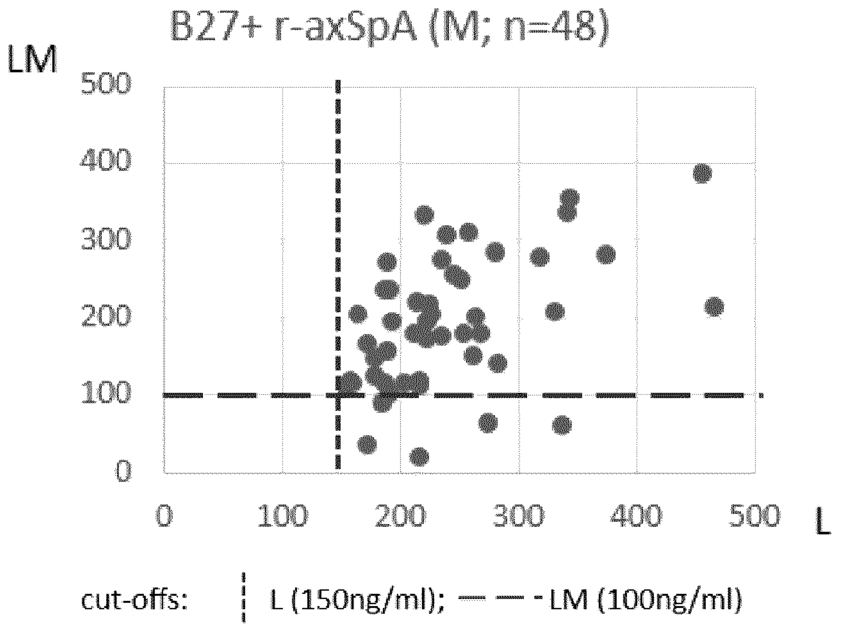

FIG. 13A shows LCN2 (L; x-axis) and LCN2-MMP9 (LM; y-axis) levels in male B27+r-axSpA patients.

Figure 13B:
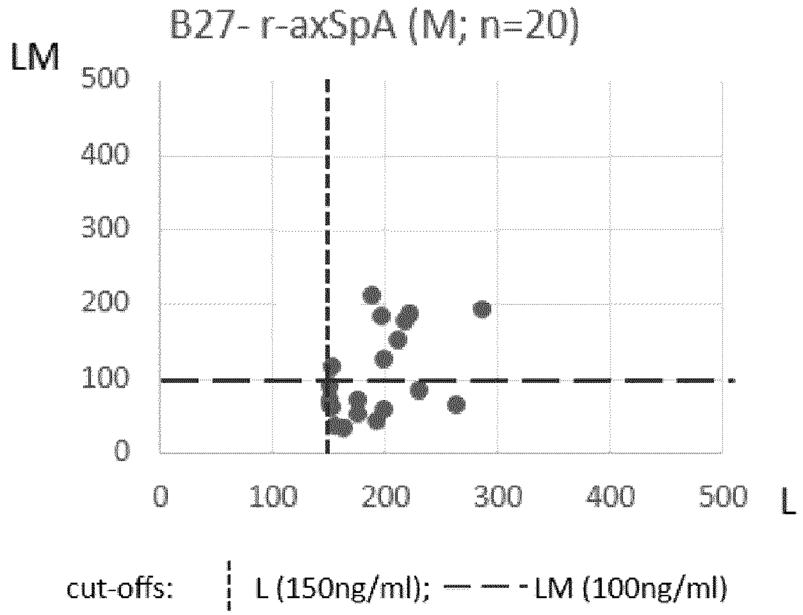

FIG. 13B shows LCN2 (L; x-axis) and LCN2-MMP9 (LM; y-axis) levels in male B27− r-axSpA patients.

Figure 14A:
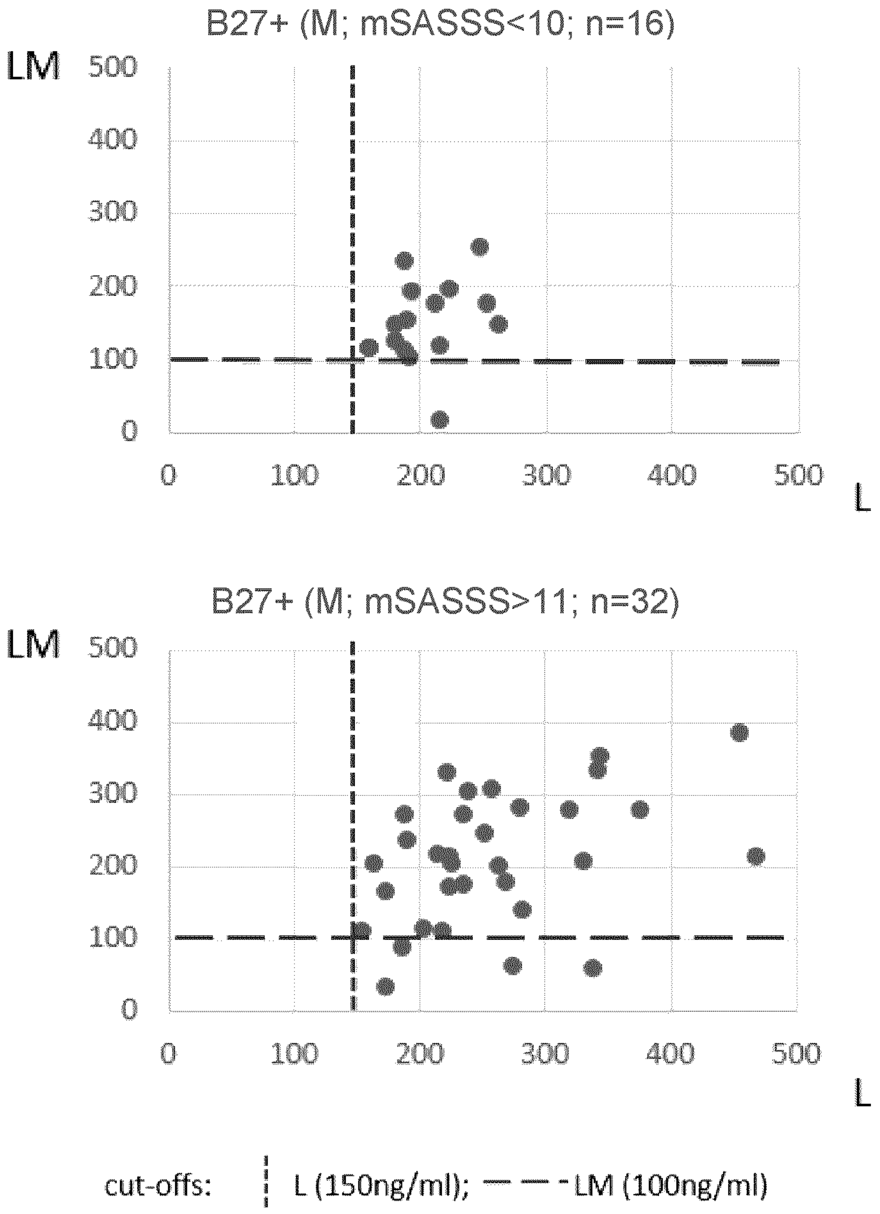

FIG. 14A shows plots of LCN2-MMP9 (LM; y-axis) vs LCN2 (L; x-axis) levels in B27+ patients with mSASSS<10 (upper graph; n=16) and B27+ patients with mSASSS>11 (lower graph; n=32). B27+L+LM+ patients with mSASSS>11 have significantly higher L and LM levels compared to those with mSASSS<10. One-way analysis of variance (ANOVA) including Tukey Honestly Significant Difference (HSD) was used to determine significance.

Figure 14B:
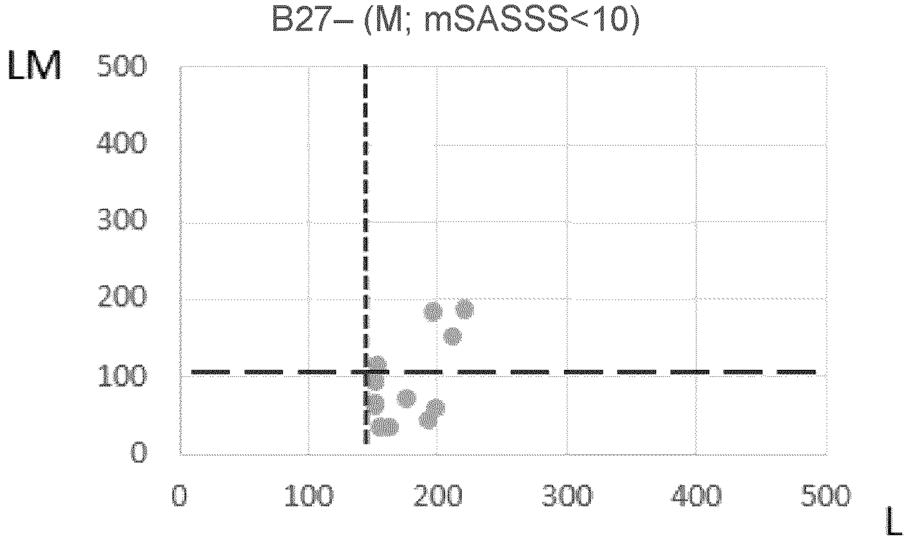
Figure 14B:
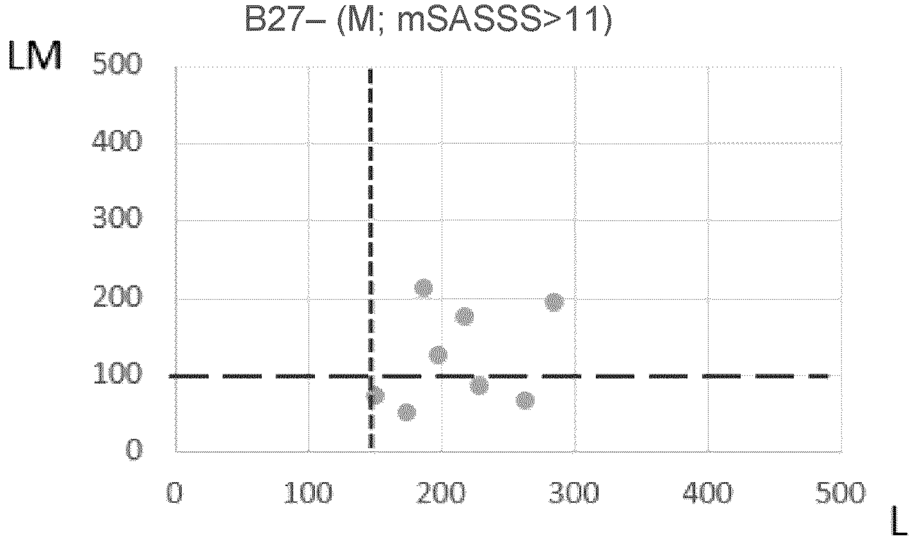

FIG. 14B shows plots of LCN2-MMP9 (LM; y-axis) vs LCN2 (L; x-axis) levels in B27− patients with mSASSS<10 (upper graph; n=12) and B27− patients with mSASSS>11 (lower graph; n=8). B27−L+ patients with mSASSS>11 have significantly higher L levels compared to those with mSASSS<10. One-way analysis of variance (ANOVA) including Tukey Honestly Significant Difference (HSD) was used to determine significance.

Figure 15A:
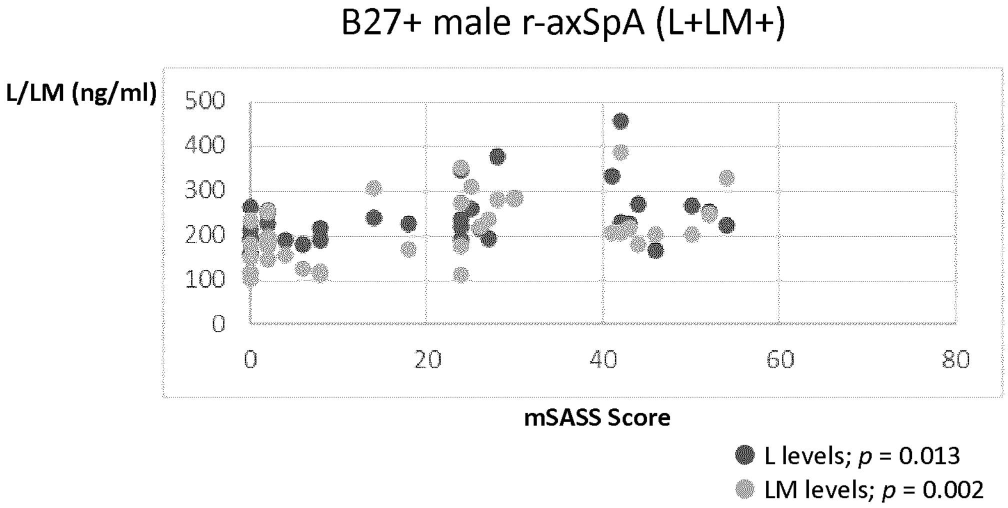

FIG. 15A shows the correlation of LCN2 (L; black dots) and LCN2-MMP9 (LM; gray dots) levels with mSASSS in B27+L+LM+ patients (mSASSS 11-55; n=20) vs those with mSASSS<10 (n=15). Pearson's correlation coefficient tests were used to determine significance.

Figure 15B:
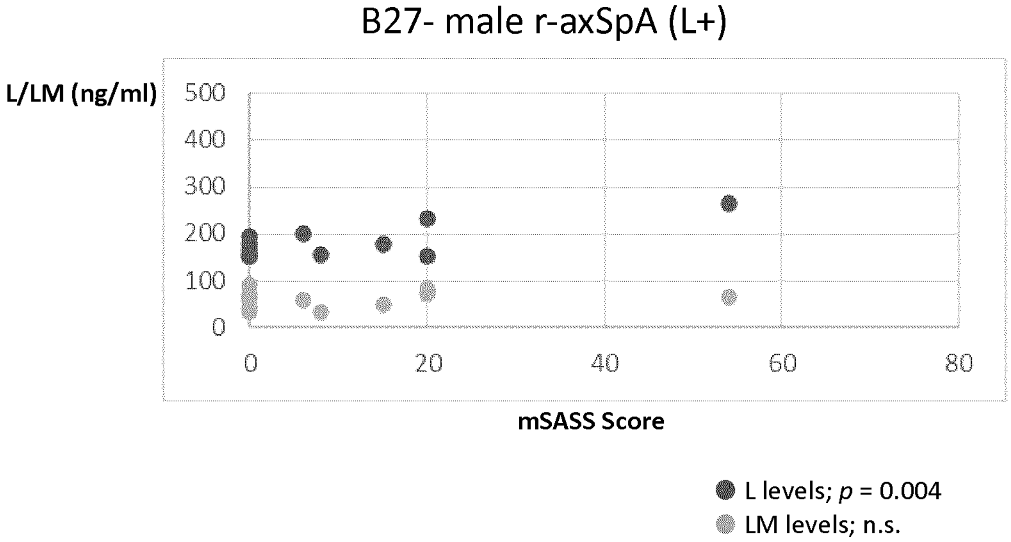

FIG. 15B shows the correlation of LCN2 (L; black dots) and LCN2-MMP9 (LM; gray dots) levels with male B27− L+ patients (mSASSS 11-55; n=4) vs those with mSASSS<10 (n=8). Pearson's correlation coefficient tests were used to determine significance. n.s. stands for not significant.

Figure 16A:
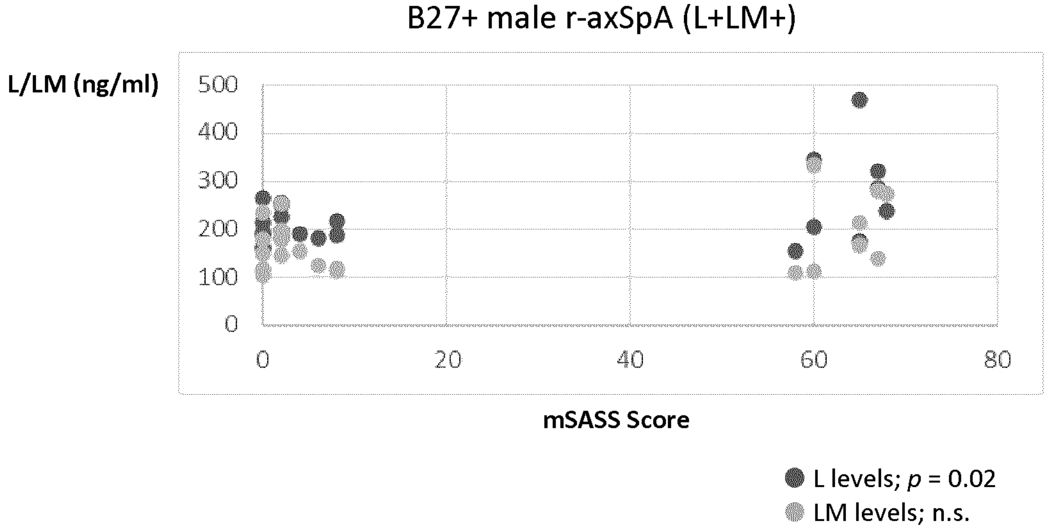

FIG. 16A shows the correlation of LCN2 (L; black dots) and LCN2-MMP9 (LM; gray dots) levels with mSASSS in B27+L+LM+ patients (mSASSS 56-72; n=8) vs those with mSASSS<10 (n=15). L but not LM levels were significantly correlated with mSASSS. Pearson's correlation coefficient tests were used to determine significance. n.s. stands for not significant.

Figure 16B:
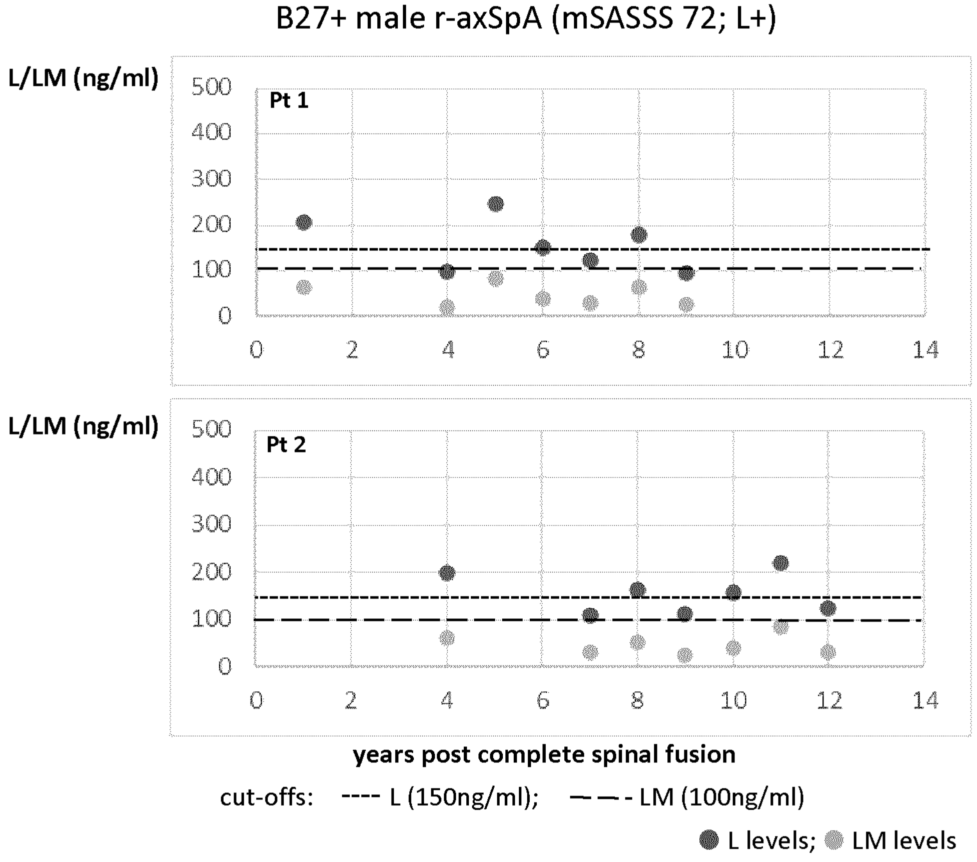

FIG. 16B shows sequential measurements of LCN2 (L; black dots) and LCN2-MMP9 levels (LM; gray dots) in two (Pt 1 and Pt 2) B27+ male patients with completely fused spine (mSASSS 72).

Figure 17:
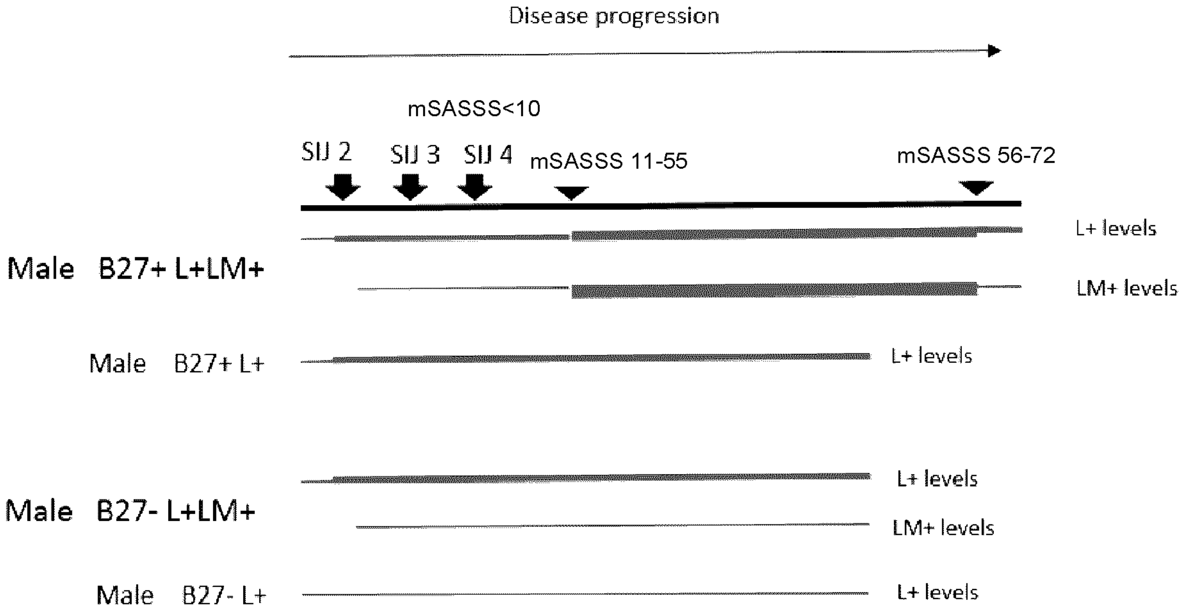

FIG. 17 shows schematics of the differences in LCN2 (L+) and LCN2-MMP9 (LM+) levels during disease progression in male r-axSpA patients with different B27 status and L/LM patterns.

Figure 18:
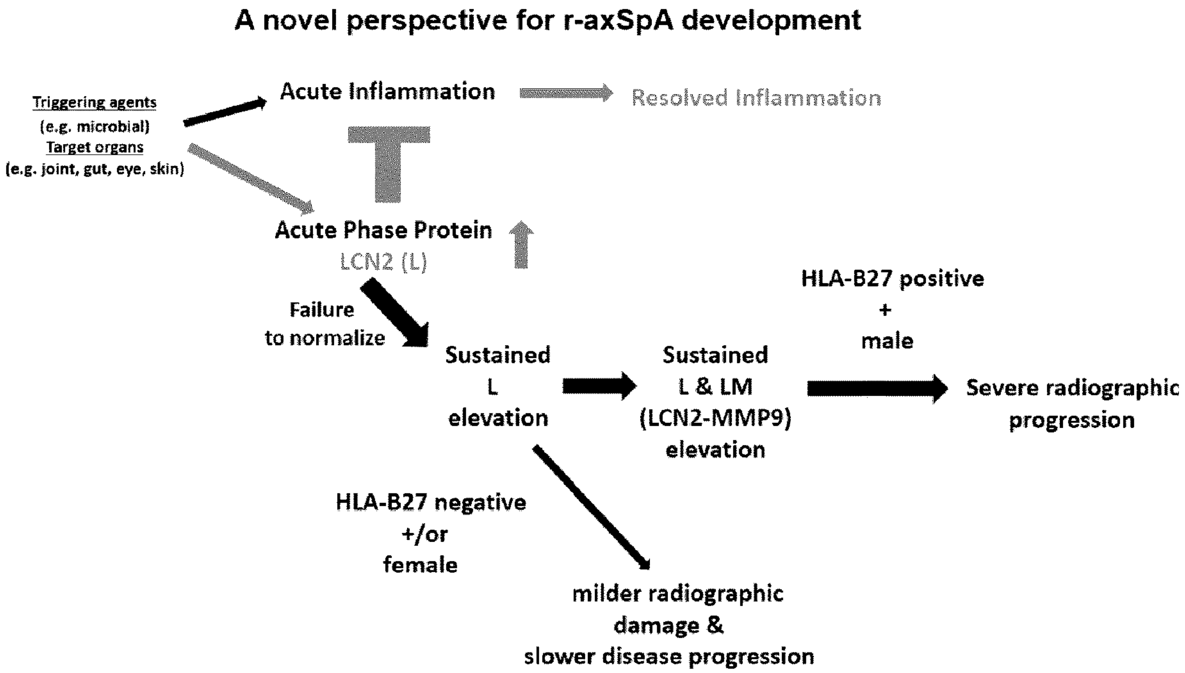

FIG. 18 shows a model of r-axSpA development. LCN2 (L) as one of the acute phase proteins of the self-defense mechanism (innate immunity), is produced when triggered by agents such as microbial factors to prevent acute infection. Failure to normalize L in a timely manner would lead to chronic inflammation, reflected by elevation of L (L+) as well as concurrent elevation of L and LM (L+LM+) in the circulation. In HLA-B27 positive male patients, L+LM+ is the predominant pattern, resulting in severe SIJ and spinal inflammation and eventual drastic radiographic damage. In HLA-B27 negative male patients, and female patients (irrespective of HLA-B27 status), L+ is the predominant pattern, resulting in mainly SIJ inflammation and milder radiographic damage in the spine.

Figure 19A:
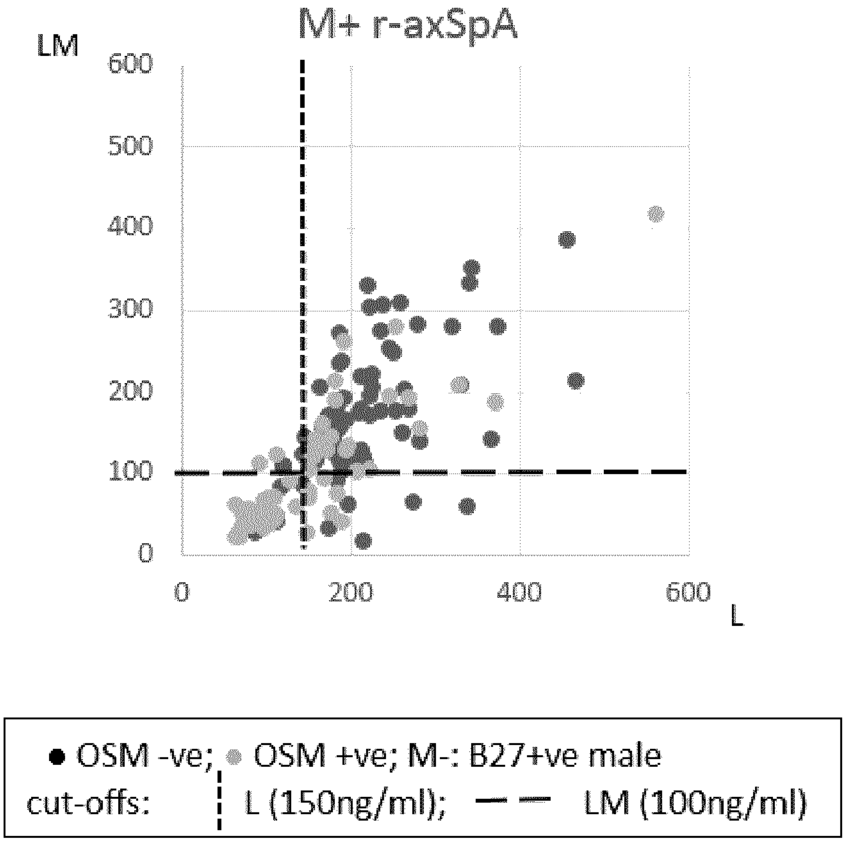

FIG. 19A shows a comparison of LCN2 (L) and LCN2-MMP9 (LM) levels between male OSM− (n=72; black dots) and OSM+ (n=54; 43%; gray dots) patients. Both L and LM levels are significantly lower in OSM+ patients than OSM− patients. Independent Student's t tests were used to determine significance.

Figure 19B:
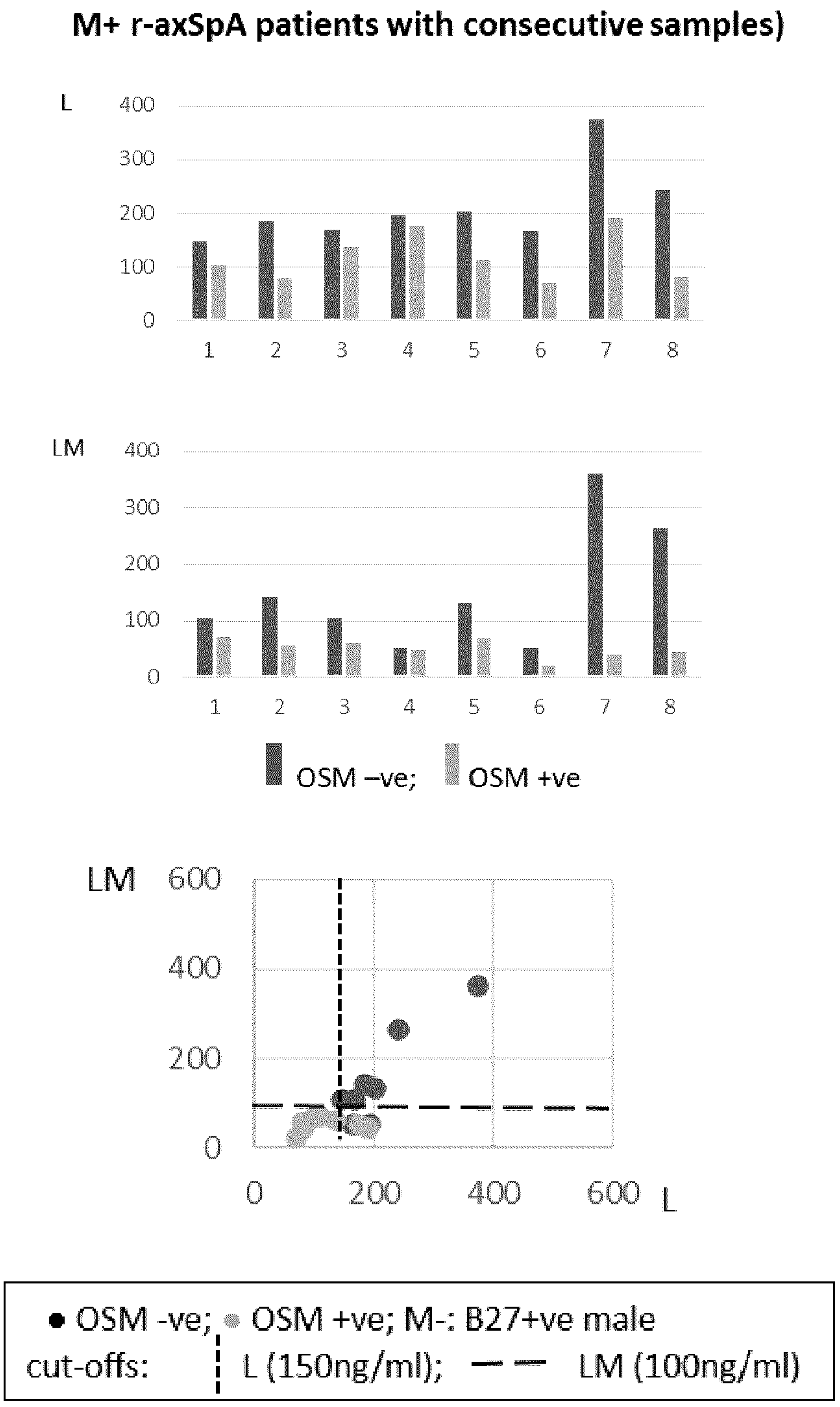

FIG. 19B shows LCN2 (L) and LCN2-MMP9 (LM) levels in 8 male patients with 2 consecutive samples in which one sample is OSM− (black bars and dots) and the other is OSM+(gray bars and dots). Patients 1-4 have mSASSS<10 and patients 5-8 have mSASSS>11. OSM positivity is associated with lower L and LM levels. Paired Student's t tests were used to determine significance.

Figure 19C:
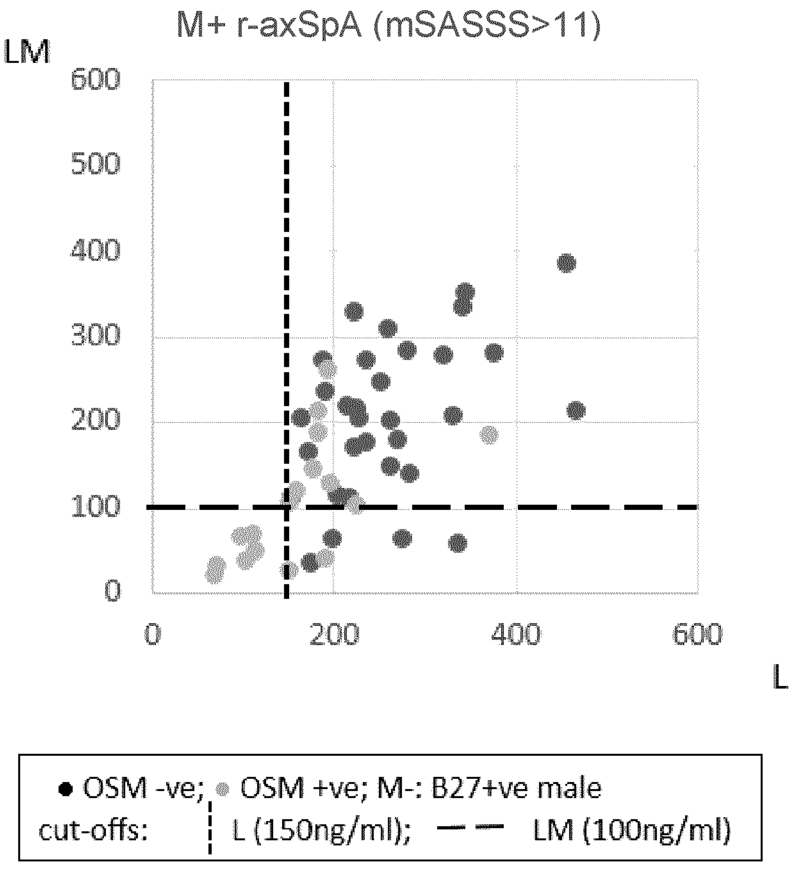

FIG. 19C shows a comparison of LCN2 (L) and LCN2-MMP9 (LM) levels between male OSM− (n=32; black dots) and OSM+ (n=17; 35%; gray dots) patients with mSASSS>11. OSM+ mSASSS>11 patients have significantly higher L and LM levels than do OSM− mSASSS>11 patients. Independent Student's t tests were used to determine significance.

Figure 20A:
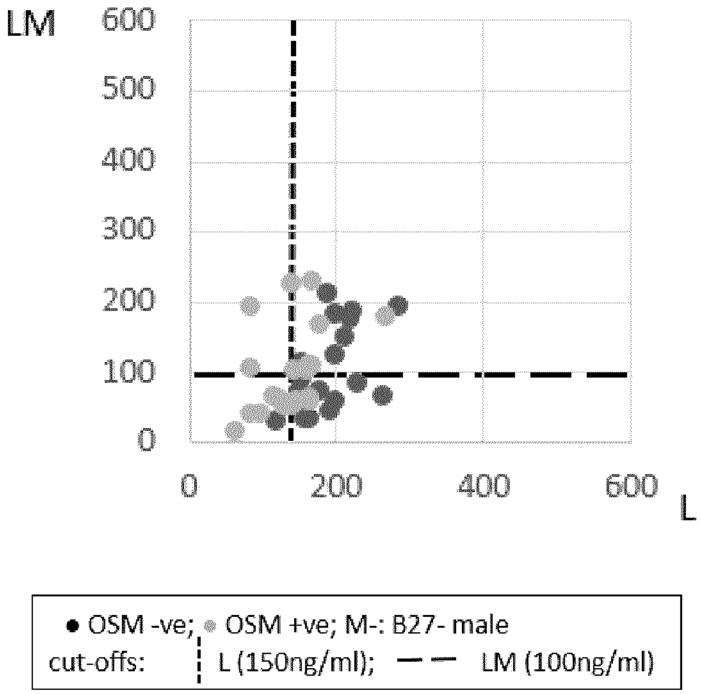

FIG. 20A shows a comparison of LCN2 (L) and LCN2-MMP9 (LM) levels between male B27− OSM− (n=21; black dots) and male B27− OSM+ (n=20; 49%; gray dots) patients. B27− OSM+ patients had significantly lower L but not LM levels. Independent Student's t tests were used to determine significance.

Figure 20B:
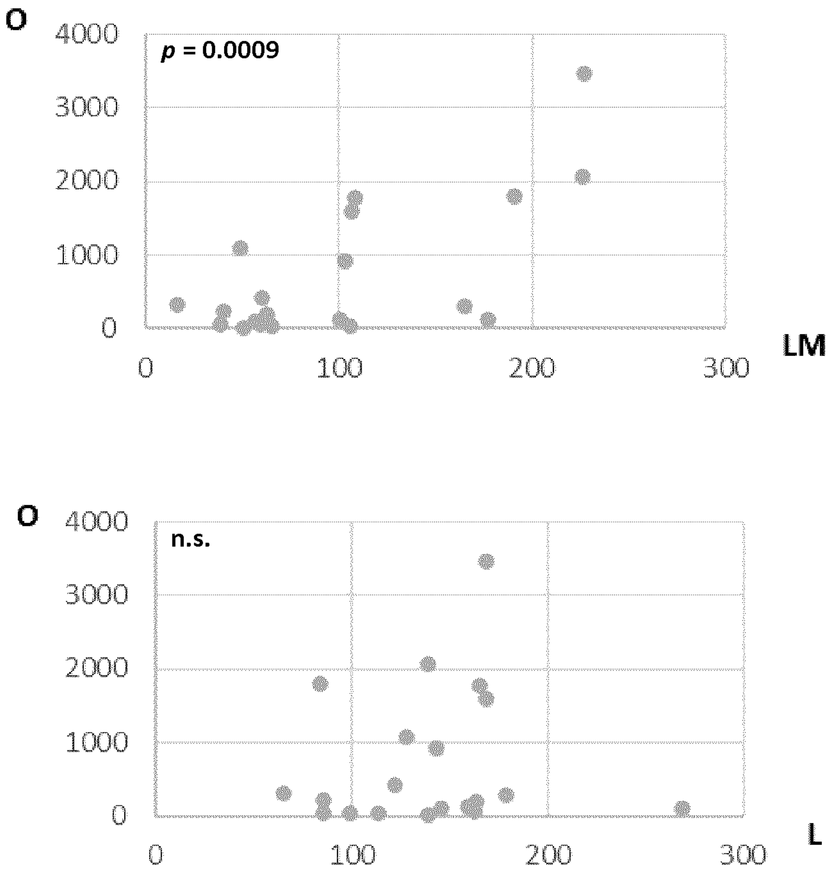

FIG. 20B shows comparisons between OSM (O) levels and LCN2-MMP9 (LM) levels (on top) and between O levels and LCN2 (L) levels (on the bottom) in male B27− OSM+ patients. LM levels, but not L levels, are correlated with O levels in these patients. Pearson's correlation coefficient tests were used to determine significance. n.s. stands for not significant.

DESCRIPTION OF VARIOUS EMBODIMENTS

The following is a detailed description provided to aid those skilled in the art in practicing the present disclosure.

Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

I. Definitions

As used herein, the following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present specification, including definitions, will control. In addition, the materials, methods, and Examples are illustrative only and not intended to be limiting.

The term "spondyloarthritis" as understood in the art and used herein refers to a family of related autoinflammatory diseases, including reactive arthritis (ReA), psoriatic arthritis (PsA), IBD-related SpA, undifferentiated SpA (USpA), radiographic axial spondyloarthritis (r-axSpA), also referred to as ankylosing spondylitis (AS) and non-radiographic axial SpA (nr-axSpA).

The term "axial spondyloarthritis" (known interchangeably as "axial spondylitis"), also referred to as axSpA, as understood in the art and used herein refers to a subset of spondyloarthritis that predominantly affect the axial skeleton, including the sacroiliac joints (SIJs) and the spine, and includes undifferentiated SpA, non-radiographic axial spondyloarthritis (nr-axSpA) and radiographic axial spondyloarthritis (r-axSpA; also referred to as ankylosing spondylitis (AS)). The distinctive features include sacroiliac joint and/or axial joint inflammation which precede neo-ossification at inflammatory sites.

The term "ankylosing spondylitis" also referred to as "radiographic axial spondyloarthritis" (r-axSpA) as understood in the art and used herein, refers to a disease featured by chronic inflammatory arthritis primarily affecting the axial joints.

The term "polypeptide" as used herein refers to a polymer consisting a number of amino acid residues bonded together in a chain. The polypeptide can form a part or the whole of a protein. The polypeptide may be arranged in a long, continuous and unbranched peptide chain. The polypeptide may also be arranged in a biologically functional way. The polypeptide may be folded into a specific three-dimensional structure that confers it a defined activity. The term "polypeptide" as used herein is used interchangeably with the term "protein".

The term "LCN2" or "L", also referred to as NGAL and HNL, as used herein means lipocalin 2 and includes all naturally occurring forms, including monomers, homo-dimers and homo-oligomers, for example, from all species and particularly human including for example accession number P80188.2 herein incorporated by reference. The LCN2 homodimer is produced primarily by neutrophils. The homodimer is released by neutrophils at sites of local inflammation where neutrophils are involved in acute inflammation. In chronic inflammation such as r-axSpA, LCN2 monomer, produced by local reacting cells is dominant. Heterodimers such as LCN2-MMP9 are considered a separate entity from LCN2.

The term "OSM" or "O", also referred to as OncoM, as used herein means oncostatin M which is a cytokine and includes all naturally occurring forms, for example from all species and particularly human including for example accession number P13725.2, herein incorporated by reference.

The term "LCN2-MMP9" or "LM", as used herein means heterodimers having LCN2 and MMP9 as components and includes all naturally occurring forms, for example from all species and particularly human including for example having the MMP9 component under accession number P14780, herein incorporated by reference.

The term "monitoring" as used herein refers observation of a disease, condition or one or several medical parameters over time, as relating to clinical disease activity, treatment response, disease progression, and/or active repair.

The term "clinical disease activity" as used herein refers to observation of lower back pain evaluated by a patient's self-assessment scores and/or inflammation reflected by elevated levels of biomarkers. For example, clinical disease activity in axSpA can be identified by symptoms, e.g., local back pain can be quantified by self-administered tools such as BASDAI, and/or signs such as restriction of back movement, and/or imaging e.g., MRI. The skilled person recognizes that MRI is more sensitive than X rays, but not as sensitive as clinical symptoms and signs or as laboratory tests of blood (e.g., erythrocyte sedimentation rate (ESR) and CRP, which have their own limitations). In axSpA, the current blood tests have limitations. ESR and CRP measure the liver's secretion of proteins, fibrinogen, and CRP, respectively, as a response to inflammation elsewhere. This is termed systemic inflammation and in the case of axSpA is quite insensitive as, for example, some patients have active disease without elevation of these markers. The biomarkers LCN2 and LCN2-MMP9 are produced locally at inflammation sites and therefore serum LCN2 and serum LCN2-MMP9 (but not serum MMP-9 itself) directly reflect local inflammation activity. As disclosed herein, when elevated these would be biomarkers of clinical disease activity that indicate the presence and severity of local inflammation.

The term "treatment response" refers to stabilization of disease, an improvement in disease status, or normalization of ongoing inflammation. The term "good treatment response" in the context of a subject as used herein refers to a positive therapeutic response to treatment, for example alleviation or amelioration of one or more symptoms or conditions, diminishment of extent of disease, stabilized (i.e., not worsening) state of disease, preventing spread of disease, reversal of disease, amelioration or palliation of the disease state, and remission (whether partial or total), whether detectable or undetectable. For example, good treatment response can be the improvement or resolve of one or more disease features, in the context of axSpA, including but not limited to inflammatory back pain, SIJ inflammation, decreased or ceased persistent pain, and/or decreased pain flare up frequency or intensity. The skilled person recognizes that inflammation reflected by MRI is reversible. While MRI can profile structural changes such as erosions and ankylosis, SPARCC score is for evaluating bone marrow edema, which is thought to represent inflammation and is potentially reversible. A responder is a subject that exhibits a good treatment response. Also, a positive therapeutic response to treatment refers to, for example, decrease in LCN2, LCN2-MMP9, and/or OSM levels (a reflection of ongoing joint inflammation); or normalization of LCN2, LCN2-MMP9, and/or OSM levels; and/or decrease in the scores of low back pain functional indices. Resolution of low back pain together with normalization of LCN2, LCN2-MMP9, and/or OSM levels is regarded as good treatment response. Resolution of low back pain but LCN2, LCN2-MMP9, and/or OSM levels remain elevated is considered as a partial clinical response (pain relieved, but inflammation remain ongoing) to treatment. The skilled person recognizes that the clinical response is to symptoms and maybe a result of analgesic effects of drugs which can be quite distinct from their anti-inflammatory effects.

The term "disease progression" as used herein means the lack of or insufficient treatment response, for example the worsening or lack of resolve of one or more disease features including in the context of axSpA, structural changes detected by progression, imaging changes including X-ray, arthritis in an axial joint which shows a site or new site of neo-ossification and ankylosis, in an axial joint located in SIJ and/or spine. Disease progression can be activity reflecting active repair following inflammation, favoring progression to joint fibrosis and ankylosis. Ankylosis, joint fusion by fibrosis or ossification, is an end stage and in r-axSpA implies previous inflammatory activity with subsequent active repair. These processes can continue in presence of ankylosis. Active repair can be detected by skilled observer in some MRI imaging patterns. Serum LCN2-MMP9 in the present disclosure is a definitive marker of active repair. In connective tissues, it is important to recognize that repair processes can lead either to restitution (regeneration) or can be excessive leading to fibrosis (scar) and hence to disease progression resulting ultimately in fibrous or osseous ankylosis. X-rays using mSASSS are a measure of structural changes (syndesmophyte formation, etc.), Worsening of disease features might also involve SIJ inflammation, ankylosis of the spine, active disease persistence, and/or requirement of hospitalization for clinical disease activity. Ankylosis of spinal components is end stage disease and inflammation can still be ongoing in patients with a completely fused spine. Some patients with fused spines remain having elevated levels of LCN2, LCN2-MMP9, and/or OSM, or elevated level of LCN2 only, indicating active ongoing local inflammation. Ongoing inflammation and/or pain are features of active disease persistence. A non-responder is a subject with elevated LCN2, LCN2-MMP9 and/or OSM levels (ongoing inflammation) and/or with unresolved back pain post-treatment. Patients with resolved back pain but remain having elevated LCN2, LCN2-MMP9 and/or OSM levels after treatment are considered as clinical partial responders. Patients with reduced but still elevated marker levels irrespective of pain status are also considered partial responders. The skilled person recognizes that, typically, the threshold for partial clinical response is a 25% reduction although allowances are permitted because in practice this is difficult to measure.

The term "back pain score" as used herein refers to any back pain score, for example a score obtained from a self-reported pain assessment such as the BASDAI questionnaire, for example, question number 2 in the BASDAI questionnaire.

The term "chronic inflammation" as used herein refers to inflammation that is present in a subject for a prolonged period, for example at least 3 months.

The term "chronic inflammatory disease" as used herein is an inflammatory disease persisting for more than 3 months as exemplified by axSpA and inflammatory bowel disease (IBD).

The term "chronic inflammatory bowel disease" as used herein is inflammatory bowel disease persisting for >3 months without defined microbial cause amenable to antibiotic treatments. In particular, inflammatory bowel disease (IBD) refers to ulcerative colitis, Crohn's disease and cases which are deemed intermediate between these two entities. Both main types of IBD (i.e., ulcerative colitis and Crohn's disease) could benefit from assessment using biomarkers described herein such as in predicting spondylitis development in IBD and predicting IBD development in spondylitis. It is recognized that both ulcerative colitis and Crohn's disease can have acute clinical exacerbations.

The term "flares" as used herein refers to clinical exacerbations of clinical disease activity usually involving increase in symptoms and signs.

The term "disease activity fluctuation" as used herein refers to rise, fall and subsequent rise, and/or fall, rise and subsequent fall, of any or all of symptoms, signs, lab test analytes, imaging features associated with a disease. Disease activity fluctuation is indicative of instability or periodicity of disease activity. A subject under treatment who is experiencing disease activity fluctuation is suffering from inadequate treatment, and such a subject may benefit from a change in treatment.

The term "antibody" as used herein is intended to include monoclonal antibodies including chimeric and humanized monoclonal antibodies, polyclonal antibodies, humanized antibodies, human antibodies, and chimeric antibodies. The antibody may be from recombinant sources and/or produced in transgenic animals. The term "antibody fragment" as used herein is intended to include Fab, Fab', $F(ab')_2$, scFv, dsFv, ds-scFv, dimers, minibodies, diabodies, and multimers thereof and bispecific antibody fragments. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques. The skilled person can readily recognize that a suitable antibody for the disclosure is any antibody useful for detecting biomarkers described herein in any detection method described herein. For example, useful antibodies include antibodies that specifically bind to LCN2, LCN2-MMP9, and/or OSM polypeptide. Useful methods for detecting LCN2-MMP9 include, for example, ELISA in which anti-MMP9 antibodies are first coated onto an assay plate for capturing MMP9, including LCN2-MMP9 heterodimers, and then the captured LCN2-MMP9 heterodimers are detected by anti-LCN2 antibodies that are capable of recognizing LCN2-MMP9 heterodimers.

The term "detection agent" refers to an agent (optionally a detection antibody) that selectively binds and is capable of binding its cognate biomarker compared to another molecule and which can be used to detect a level and/or the presence of the biomarker. A biomarker specific detection agent can include probes and the like as well as binding polypeptides such as antibodies which can for example be used with immunohistochemistry (IHC), Luminex® based assays, ELISA, immunofluorescence, radioimmunoassay, dot blotting, FACS, protein microarray, Western blots, immunoprecipitation followed by SDS-PAGE immunocytochemistry Simple Plex assay or Mass Spectrometry to detect the polypeptide level of a biomarker described herein. Similarly, "an antibody or fragment thereof" (e.g. binding fragment), that specifically binds a biomarker refers to an antibody or fragment that selectively binds its cognate biomarker compared to another molecule. "Selective" is used contextually, to characterize the binding properties of an antibody. An antibody that binds specifically or selectively to a given biomarker or epitope thereof will bind to that biomarker and/or epitope either with greater avidity or with more specificity, relative to other, different molecules. For example, the antibody can bind 3-5, 5-7, 7-10, 10-15, 5-15, or 5-30 fold more efficiently to its cognate biomarker compared to another molecule. The "detection agent" can for example be coupled to or labeled with a detectable marker. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The term "level" as used herein refers to an amount (e.g., relative amount or concentration as well as parameter values calculable based thereon such as a rate or ratio) of biomarker (i.e. polypeptide related level) that is detectable, measurable or quantifiable in a test biological sample and/or a reference biological sample, for example a test sample and/or a reference sample. For example, the level can be a concentration, e.g., of a polypeptide or a complex of polypeptides, in weight units such as mg/L, μg/L, ng/mL, or pg/mL, or in mass molar units such as pM, nM, μM, or mM. For example, when the level is determined by ELISA assay, the level can be a concentration in weight units such as mg/L, μg/L, ng/mL, or pg/mL.

The term "reference profile" as used herein is a cut-off value or values or range indicative of normal or elevated protein expression, for example for a selected specificity and/or sensitivity and can also include expression pattern parameters such as persistent or transient, related to one or more biomarker protein concentrations in a control or a group of samples, such as an average or median level based on known disease progression/outcome or treatment response patients. For example, where the reference profile being compared to is a cut off value, above or below said cut-off value a subject is identified as having elevated or normal protein expression and where the reference profile being compared to comprises a range, within a range can be indicative of normal and above the range can be indicative of elevated protein expression. Where the reference profile further comprises a pattern, the sample measured level is compared to the cut off value or range and the pattern. A reference profile can for example be derived from a value derived from a population of subjects that are known to have elevated and/or normal protein expression and is calculated for a preselected degree of specificity and/or sensitivity, and which classifies other subjects as having elevated and/or normal protein expression. In some embodiments, the cut-off for LCN2 is about 100 ng/mL or about 150 ng/ml. In some embodiments, the cut-off for LCN2 is about 100 ng/mL. In some embodiments, the cut-off for LCN2 is about 150 ng/ml. In some embodiments, the cut-off for LCN2-MMP9 is about 50 ng/mL or about 100 ng/mL. In some embodiments, the cut-off for LCN2-MMP9 is about 50 ng/mL. In some embodiments, the cut-off for LCN2-MMP9 is about 100 ng/mL.

The term "transient" or "t" as used herein refers to a level of protein expression that lasts a short time for example less than 3 months, less than two months or less than one month, and no longer than 3 years. For time periods greater than 3 months and less than 3 years, transient elevation refers to only one out of several samples collected within this time period which has elevated protein expression. A transient elevation can for example mean that only one out of several samples (2 or more) within a time period has elevated protein expression, or that a subsequent sample taken within a time period after a sample with elevated expression has normal or about normal expression, for example wherein the samples are taken within a period of 1 month, 2 months or 3 months or longer, or where the sample(s) exhibits a similar pattern to a transient reference profile. Transient may also refer to a change in the level of protein expression with or without a change in therapy.

The term "persistent" or "p" as used herein refers to a level of protein expression that persists for a sustained period, for example greater than 3 months. A persistent elevation can for example mean that elevated protein expression is maintained above a certain threshold, for example, above normal range, in samples assessed taken at different times over the period, for example 3 months or longer, or where the sample exhibits a similar pattern to a transient reference profile but over a longer period of time. A persistent elevation does not necessarily mean persistently elevated at the same level but rather any elevated level persisting over time as described above.

The term "normal" or "n" as used herein refers to a level of protein expression that is not elevated as compared to a range based on samples (e.g., healthy individuals) reference range or for example a reference profile indicative of normal expression, for example the group of individuals with the signature LnLMnOn. For instance, the reference range for healthy individuals was determined by analyzing the markers in separate cohorts of healthy male and female individuals and determining the concentration distribution of the analytes range. The upper limit of the reference range (normal range) is chosen at the average level of 2 standard deviations of the reference healthy cohort population.

The term "elevated" or "e" as used herein refers to a level of protein expression that is increased above normal as compared to a range based on normal samples (e.g., healthy control reference) or for example a reference profile indicative of normal expression.

The term "LCN2tOSMt" or "LtOt" as used herein refers to a reference profile where LCN2 levels are transiently elevated and OSM levels are transiently elevated. The reference profile comprises a value or values for LCN2 and a value or values for OSM.

The term "LCN2pOSMt" or "LpOt" as used herein refers to a reference profile where LCN2 levels are persistently elevated and OSM levels are transiently elevated. The reference profile comprises a value or values for LCN2 and a value or values for OSM.

The term "LCN2pOSMp" or "LpOp" as used herein refers to a reference profile where LCN2 levels are persistently elevated and OSM levels are persistently elevated. The reference profile comprises a value or values for LCN2 and a value for OSM.

The term "LCN2tOSMp" or "LtOp" as used herein refers to a reference profile where LCN2 levels are transiently elevated and OSM levels are persistently elevated. The reference profile comprises a value for LCN2 and a value or values for OSM.

The term "LCN2nOSMp" or "LnOp" as used herein refers to a reference profile where normal LCN2 levels and OSM levels are persistently elevated. The reference profile comprises a value or values for LCN2 and a value or values for OSM.

The term "LCN2nOSMt" or "LnOt" as used herein refers to a reference profile where normal LCN2 levels and OSM levels are transiently elevated. The reference profile comprises a value or values for LCN2 and a value or values for OSM.

The term "LCN2pOSMn" or "LpOn" as used herein refers to a reference profile where LCN2 levels are persistently elevated and OSM levels are normal. The reference profile comprises a value or values for LCN2 and a value or values for OSM.

The term "LCN2tOSMn" or "LtOn" as used herein refers to a reference profile where LCN2 levels that are transiently elevated and OSM levels are normal. The reference profile comprises a value or values for LCN2 and a value or values for OSM.

The term "LCN2nOSMn" or "LnOn" as used herein refers to a reference profile where LCN2 levels are normal and OSM levels are normal. The reference profile comprises a value or values for LCN2 and a value or values for OSM.

The term "LCN2tLCN2-MMP9tOSMt" or "LtLMtOt" as used herein refers to a reference profile where LCN2 levels are transiently elevated, LCN2-MMP9 levels are transiently elevated, and OSM levels are transiently elevated. The reference profile comprises a value or values for LCN2, a value or values for LCN2-MMP9, and a value or values for OSM.

The term "LCN2tLCN2-MMP9tOSMp" or "LtLMtOp" as used herein refers to a reference profile where LCN2 levels are transiently elevated, LCN2-MMP9 levels are transiently elevated, and OSM levels are persistently elevated. The reference profile comprises a value or values for LCN2, a value or values for LCN2-MMP9, and a value or values for OSM.

The term "LCN2tLCN2-MMP9pOSMt" or "LtLMpOt" as used herein refers to a reference profile where LCN2 levels are transiently elevated, LCN2-MMP9 levels are persistently elevated, and OSM levels are transiently elevated. The reference profile comprises a value or values for LCN2, a value or values for LCN2-MMP9, and a value or values for OSM.

The term "LCN2tLCN2-MMP9pOSMp" or "LtLMpOp" as used herein refers to a reference profile where LCN2 levels are transiently elevated, LCN2-MMP9 levels are persistently elevated, and OSM levels are persistently elevated. The reference profile comprises a value or values for LCN2, a value or values for LCN2-MMP9, and a value or values for OSM.

The term "LCN2pLCN2-MMP9tOSMt" or "LpLMtOt" as used herein refers to a reference profile where LCN2 levels are persistently elevated, LCN2-MMP9 levels are transiently elevated, and OSM levels are transiently elevated. The reference profile comprises a value or values for LCN2, a value or values for LCN2-MMP9, and a value or values for OSM.

The term "LCN2pLCN2-MMP9tOSMp" or "LpLMtOp" as used herein refers to a reference profile where LCN2 levels are persistently elevated, LCN2-MMP9 levels are transiently elevated, and OSM levels are persistently elevated. The reference profile comprises a value or values for LCN2, a value or values for LCN2-MMP9, and a value or values for OSM.

The term "LCN2pLCN2-MMP9pOSMt" or "LpLMpOt" as used herein refers to a reference profile where LCN2 levels are persistently elevated, LCN2-MMP9 levels are persistently elevated, and OSM levels are transiently elevated. The reference profile comprises a value or values for LCN2, a value or values for LCN2-MMP9, and a value or values for OSM.

The term "LCN2pLCN2-MMP9pOSMp" or "LpLMpOp" as used herein refers to a reference profile where LCN2 levels are persistently elevated, LCN2-MMP9 levels are persistently elevated, and OSM levels are persistently elevated. The reference profile comprises a value or values for LCN2, a value or values for LCN2-MMP9, and a value or values for OSM.

The term "LCN2nLCN2-MMP9tOSMt" or "LnLMtOt" as used herein refers to a reference profile where LCN2 levels are normal, LCN2-MMP9 levels are transiently elevated, and OSM levels are transiently elevated. The reference profile comprises a value or values for LCN2, a value or values for LCN2-MMP9, and a value or values for OSM.

The term "LCN2nLCN2-MMP9tOSMp" or "LnLMtOp" as used herein refers to a reference profile where LCN2 levels are normal, LCN2-MMP9 levels are transiently elevated, and OSM levels are persistently elevated. The reference profile comprises a value or values for LCN2, a value or values for LCN2-MMP9, and a value or values for OSM.

The term "LCN2nLCN2-MMP9pOSMt" or "LnLMpOt" as used herein refers to a reference profile where LCN2 levels are normal, LCN2-MMP9 levels are persistently elevated, and OSM levels are transiently elevated. The reference profile comprises a value or values for LCN2, a value or values for LCN2-MMP9, and a value or values for OSM.

The term "LCN2nLCN2-MMP9pOSMp" or "LnLMpOp" as used herein refers to a reference profile where LCN2 levels are normal, LCN2-MMP9 levels are persistently elevated, and OSM levels are persistently elevated. The reference profile comprises a value or values for LCN2, a value or values for LCN2-MMP9, and a value or values for OSM.

The term "LCN2tLCN2-MMP9nOSMt" or "LtLMnOt" as used herein refers to a reference profile where LCN2 levels are transiently elevated, LCN2-MMP9 levels are normal, and OSM levels are transiently elevated. The reference profile comprises a value or values for LCN2, a value or values for LCN2-MMP9, and a value or values for OSM.

The term "LCN2tLCN2-MMP9nOSMp" or "LtLMnOp" as used herein refers to a reference profile where LCN2 levels are transiently elevated, LCN2-MMP9 levels are normal, and OSM levels are persistently elevated. The reference profile comprises a value or values for LCN2, a value or values for LCN2-MMP9, and a value or values for OSM.

The term "LCN2pLCN2-MMP9nOSMt" or "LpLMnOt" as used herein refers to a reference profile where LCN2 levels are persistently elevated, LCN2-MMP9 levels are normal, and OSM levels are transiently elevated. The reference profile comprises a value or values for LCN2, a value or values for LCN2-MMP9, and a value or values for OSM.

The term "LCN2pLCN2-MMP9nOSMp" or "LpLMnOp" as used herein refers to a reference profile where LCN2 levels are persistently elevated, LCN2-MMP9 levels are normal, and OSM levels are persistently elevated. The reference profile comprises a value or values for LCN2, a value or values for LCN2-MMP9, and a value or values for OSM.

The term "LCN2tLCN2-MMP9tOSMn" or "LtLMtOn" as used herein refers to a reference profile where LCN2 levels are transiently elevated, LCN2-MMP9 levels are transiently elevated, and OSM levels are normal. The reference profile comprises a value or values for LCN2, a value or values for LCN2-MMP9, and a value or values for OSM.

The term "LCN2tLCN2-MMP9pOSMn" or "LtLMpOn" as used herein refers to a reference profile where LCN2 levels are transiently elevated, LCN2-MMP9 levels are persistently elevated, and OSM levels are normal. The reference profile comprises a value or values for LCN2, a value or values for LCN2-MMP9, and a value or values for OSM.

The term "LCN2pLCN2-MMP9tOSMn" or "LpLMtOn" as used herein refers to a reference profile where LCN2 levels are persistently elevated, LCN2-MMP9 levels are transiently elevated, and OSM levels are normal. The reference profile comprises a value or values for LCN2, a value or values for LCN2-MMP9, and a value or values for OSM.

The term "LCN2pLCN2-MMP9pOSMn" or "LpLMpOn" as used herein refers to a reference profile where LCN2 levels are persistently elevated, LCN2-MMP9 levels are persistently elevated, and OSM levels are normal. The reference profile comprises a value or values for LCN2, a value or values for LCN2-MMP9, and a value or values for OSM.

The term "LCN2nLCN2-MMP9nOSMt" or "LnLMnOt" as used herein refers to a reference profile where LCN2 levels are normal, LCN2-MMP9 levels are normal, and OSM levels are transiently elevated. The reference profile comprises a value or values for LCN2, a value or values for LCN2-MMP9, and a value or values for OSM.

The term "LCN2nLCN2-MMP9nOSMp" or "LnLMnOp" as used herein refers to a reference profile where LCN2 levels are normal, LCN2-MMP9 levels are normal, and OSM levels are persistently elevated. The reference profile comprises a value or values for LCN2, a value or values for LCN2-MMP9, and a value or values for OSM.

The term "LCN2nLCN2-MMP9tOSMn" or "LnLMtOn" as used herein refers to a reference profile where LCN2 levels are normal, LCN2-MMP9 levels are transiently elevated, and OSM levels are normal. The reference profile comprises a value or values for LCN2, a value or values for LCN2-MMP9, and a value or values for OSM.

The term "LCN2nLCN2-MMP9pOSMn" or "LnLMpOn" as used herein refers to a reference profile where LCN2 levels are normal, LCN2-MMP9 levels are persistently elevated, and OSM levels are normal. The reference profile comprises a value or values for LCN2, a value or values for LCN2-MMP9, and a value or values for OSM.

The term "LCN2tLCN2-MMP9nOSMn" or "LtLMnOn" as used herein refers to a reference profile where LCN2 levels are normal, LCN2-MMP9 levels are normal, and OSM levels are persistently elevated. The reference profile comprises a value or values for LCN2, a value or values for LCN2-MMP9, and a value or values for OSM.

The term "LCN2pLCN2-MMP9nOSMn" or "LpLMnOn" as used herein refers to a reference profile where LCN2 levels are normal, LCN2-MMP9 levels are normal, and OSM levels are transiently elevated. The reference profile comprises a value or values for LCN2, a value or values for LCN2-MMP9, and a value or values for OSM.

The term "LCN2tLCN2-MMP9tOSMt" or "LtLMtOt" as used herein refers to a reference profile where LCN2 levels are transiently elevated, LCN2-MMP9 levels are transiently elevated, and OSM levels are transiently elevated. The reference profile comprises a value or values for LCN2, a value or values for LCN2-MMP9, and a value or values for OSM.

The term "LCN2nLCN2-MMP9nOSMn" or "LnLMnOn" as used herein refers to a reference profile where LCN2 levels are normal, LCN2-MMP9 levels are normal, and OSM levels are normal. The reference profile comprises a value or values for LCN2, a value or values for LCN2-MMP9, and a value or values for OSM.

The term "subject" also referred as patient, as used herein includes all members of the animal kingdom including mammals, and suitably refers to humans.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made.

As used in this specification and the appended claims, the singular forms "a", "an" and "the" include plural references unless the content clearly dictates otherwise. Thus, for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be under-stood by a person skilled in the art. For example, in the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Although any methods and materials similar or equivalent to those described herein can also be used in the practice or testing of the present disclosure, examples of methods and materials are now described.

II. Methods

Described herein are polypeptide biomarkers that can be used to assess, monitor, and/or predict clinical disease activity, treatment response, disease progression, and/or active repair in a subject having a chronic inflammatory disease such as axial spondyloarthritis (axSpA) or suspected of having axial spondyloarthritis. When the disease is axSpA, MRI SPARCC sacroiliac joint (SIJ) scores and MRI Berlin spine scores are accepted indication of inflammation in SIJ and spine, respectively. The modified Stoke Ankylosing Spondylitis Spinal Score (mSASSS) is an accepted imaging evaluator for degree of disease progression (ankylosis). The present disclosure provides for methods that can be used instead of MRI or CRP for assessing, monitoring, and/or predict clinical disease activity, treatment response, and/or disease progression, in a subject having a chronic inflammatory disease such as axial spondyloarthritis or suspected of having axial spondyloarthritis.

Informative serum biomarkers for monitoring treatment responses in axSpA are previously lacking. As demonstrated in the Examples, the level of Lipocalin 2 (LCN2) and Oncostatin M (OSM) can reflect axSpA inflammation and treatment response. As described therein retrospective analysis of a longitudinal axSpA cohort was performed in 286 axSpA patients having multiple clinical assessments and concurrent measurements of serum LCN2 and OSM for up to 12 years. Biomarkers levels were correlated with treatment response and with MRI scoring. Two patterns of LCN2, LCN2-MMP9 and OSM elevation were observed in axSpA patients: persistent and transient. Both concordant and discordant patterns of LCN2, LCN2-MMP9, and OSM in relationship to back pain, the cardinal clinical symptom in axSpA was seen. With respect to treatment responses, responder (R) and non-responder (NR) were found in the concordant subset. Patients with Pain Resolved (PR; LCN2/LCN2-MMP9/OSM elevated) and Pain Persisted (PP; LCN2/LCN2-MMP9/OSM normal) constituted the discordant subset. Transient elevation of LCN2 or OSM over time was indicative of better response to all treatments. Half of patients with persistent OSM elevation had pain resolved (PR), the rest remained having pain and elevated level of LCN2/OSM (NR). Persistent elevation of LCN2 LCN2-MMP9, or OSM, but not CRP was correlated with SIJ MRI SPARCC scores. The data show that failure to normalize LCN2, LCN2-MMP9, and OSM leads to chronic inflammation. The inventors demonstrate that in axSpA, for example, elevated level of LCN2 or LCN2-MMP9 compared to a reference profile of LCN2normalLCN2-MMP9normalOSMnormal, LCN2normalLCN2-MMP9elevatedOSMnormal, LCN2elevatedLCN2-MMP9normalOSM-normal, or LCN2elevatedLCN2-MMP9elevatedOSMnormal, or persistent LCN2, LCN2-MMP9, and/or OSM elevation, reflects chronic axial and/or SIJ inflammation and lack of good treatment response.

One aspect of the present disclosure is a method for monitoring clinical disease activity, treatment response, disease progression, active repair, and/or predicting risk of developing a disease in a subject having or suspected of having a chronic inflammatory disease, optionally axial spondyloarthritis or inflammatory bowel disease, the method comprising:

- measuring in vitro a level of lipocalin2 (LCN2), a level of LCN2-MMP9, and/or a level of oncostatin M (OSM) in a sample obtained from the subject; and
- comparing the measured level of LCN2, LCN2-MMP9, and/or OSM to level in a previous sample and/or one or more reference profiles;
- wherein a differential in the measured level of LCN2, LCN2-MMP9, and/or OSM compared to the previous sample, a differential in the measured level of LCN2, LCN2-MMP9, and/or OSM compared to the one or more reference profiles, or a pattern (e.g. persistence or transience) of the measured level of LCN2, LCN2-MMP9, and/or OSM similar to the one or more reference profiles, is indicative of clinical disease activity, treatment response, disease progression, and/or active repair.

In some embodiments, the chronic inflammatory disease is axial spondyloarthritis. In some embodiments, the LCN2 is a monomer and/or homodimer. In some embodiments, the chronic inflammatory disease is inflammatory bowel disease. In some embodiments, the subject is male. In some embodiments, the subject is female. In some embodiments, the similarity of the measured level and/or pattern of LCN2, LCN2-MMP9, and/or OSM is compared to the previous sample and/or compared to the one or more reference profiles. Depending on the similarity of the sample to the one or more reference profiles, the subject is having their disease progress or not progress and if receiving treatment, is responding or not responding to treatment. A sample may be compared to a previous sample and/or previous sequential samples only, if for example it is known whether the previous sample and/or previous sequential samples have a normal or elevated protein expression for the biomarker measured. In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, elevated measured level of LCN2 and/or LCN2-MMP9 compared to a reference profile is indicative of axSpA. In some embodiments, elevated measured level of LCN2 and/or LCN2-MMP9 compared to a reference profile is indicative of chronic axial and/or SIJ inflammation. In some embodiments, elevated measured level of LCN2 and/or LCN2-MMP9 compared to a reference profile is indicative of SIJ inflammation. In some embodiments, elevated measured level of LCN2 and/or LCN2-MMP9 compared to a reference profile is indicative of chronic axial and/or SIJ inflammation. In some embodiments, elevated measured level of LCN2 compared to a reference profile is indicative of disease progression. In some embodiments, elevated measured level of LCN2 compared to a reference profile is indicative of spinal radiographic progression. In some embodiments, elevated measured level of LCN2 compared to a reference profile is indicative of spinal inflammation. In some embodiments, elevated measured level of LCN2 compared to a reference profile is indicative of ankylosis. In some embodiments, elevated measured level of LCN2 compared to a reference profile is indicative of spinal inflammation and ankylosis. In some embodiments, elevated measured level of LCN2 and LCN2-MMP9 compared to a reference profile is indicative of spinal inflammation and ankylosis. In some embodiments, the reference profile is LCN2normalLCN2-MMP9normal-OSMnormal, LCN2normalLCN2-MMP9elevatedOSMnormal, LCN2elevatedLCN2-MMP9-normalOSMnormal, or LCN2elevatedLCN2-MMP9elevatedOSMnormal. In some embodiments, the reference profile is LCN2normalLCN2-MMP9normalOSMnormal. In some embodiments, the reference profile is LCN2normalLCN2-MMP9elevatedOSMnormal. In some embodiments, the reference profile is LCN2elevatedLCN2-MMP9-normalOSMnormal. In some embodiments, the reference profile is LCN2elevatedLCN2-MMP9-elevatedOSMnormal. In some embodiments, elevated measured level of LCN2 compared to a reference profile is indicative of joint inflammation. In some embodiments, elevated measured level of LCN2 compared to a reference profile is indicative of joint inflammation in a subject having near fused spine.

In some embodiments, a sample from the subject exhibits level of LCN2 and LCN2-MMP9 similar to a reference profile of a weight ratio of LCN2-MMP9:LCN2 (w/w) of greater than or about 1:1 indicates that the subject has an increased risk of spondyloarthritis development. In some embodiments, a sample from the subject exhibits level of LCN2 and LCN2-MMP9 similar to a reference profile LCN2normalLCN2-MMP9normal and a ratio of LCN2-MMP9:LCN2 (w/w) of greater than or about 1:1 indicates that the subject has an increased risk of spondyloarthritis development. In some embodiments, the spondyloarthritis is axial spondyloarthritis.

In some embodiments, disease progression may be selected from progression of imaging changes including MRI and conventional X-rays, a site or new site of neo-ossification in SIJ and/or axial joints, and ankylosis of the spine.

In some embodiments, active repair is detected by MRI imaging patterns. In some embodiments, active repair is detected by a biomarker described herein. In some embodiments, a differential in the measured level of LCN2, LCN2-MMP9 and/or OSM compared to the previous sample, a differential in the measured level or of LCN2, LCN2-MMP9 and/or OSM compared to the one or more reference profiles, or a pattern (e.g., persistence or transience) of the measured level of LCN2, LCN2-MMP9 and/or OSM compared to the previous sample and/or the one or more reference profiles, is indicative of active repair.

In some embodiments, lack of good treatment response for inflammation may be a decreased improvement in inflammatory back pain, and/or acquisition of a comorbidity. In some embodiments, the comorbidity is inflammatory bowel disease (IBD), acute anterior uveitis (AAU), peripheral arthritis, cutaneous psoriasis, or vascular disease such as hypertension.

In some embodiments, a decrease in measured level of LCN2, LCN2-MMP9, and/or OSM compared to a previous sample and/or compared to one or more reference profiles is indicative of a treatment response. In some embodiments, a decrease in measured level of LCN2, LCN2-MMP9, and/or OSM compared to a previous sample and/or compared to one or more reference profiles is indicative of a good treatment response. For example, when a measured level of LCN2, LCN2-MMP9, and/or OSM is decreased relative to a previous sample, where the previous sample when compared to a reference profile is identified as having elevated measured level of LCN2, LCN2-MMP9, and/or OSM, the subject is having a treatment response. In some embodiments, when a measured level of LCN2, LCN2-MMP9, and/or OSM is decreased relative to a previous sample, where the previous sample when compared to a reference profile is identified as having elevated measured level of LCN2, LCN2-MMP9, and/or OSM, the subject is having a treatment response. In some embodiments, the treatment response is a good treatment response.

In some embodiments, a measured level is only compared to reference profile. In some embodiments, the reference profile is a cut-off level. For example, where a subject has been experiencing back pain, or has radiologic findings, etc. indicative of active disease, it is not necessary to compare to a previous sample. It is known in the art that to assess inflammation activity a single time point is indicative, whereas to assess treatment response two or more serial samples are used and not if the markers at a single time point is a real normal and the patient had clinically active disease previously.

In some embodiments, elevated measured level of LCN2 and/or LCN2-MMP9 compared to a reference profile is indicative of clinical disease activity and/or disease progression. In some embodiments, elevated measured level of LCN2 compared to a reference profile is indicative of disease progression. In some embodiments, elevated measured level of LCN2 compared to a reference profile is indicative of spinal radiographic progression. In some embodiments, elevated measured level of LCN2 compared to a reference profile is indicative of spinal inflammation. In some embodiments, elevated measured level of LCN2 compared to a reference profile is indicative of ankylosis. In some embodiments, elevated measured level of LCN2 compared to a reference profile is indicative of spinal inflammation and ankylosis. In some embodiments, elevated measured level of LCN2 and LCN2-MMP9 compared to a reference profile is indicative of spinal inflammation and ankylosis. In some embodiments, elevated measured level of LCN2 and/or LCN2-MMP9 compared to a reference profile is indicative of spinal inflammation and ankylosis in a male subject. In some embodiments, elevated measured level of LCN2 and/or LCN2-MMP9 compared to a reference profile is indicative of spinal inflammation and ankylosis in a female subject. In some embodiments, elevated measured level of LCN2 and/or LCN2-MMP9 compared to a reference profile is indicative of spinal inflammation and ankylosis in a B27+ male. In some embodiments, elevated measured level of LCN2 and/or LCN2-MMP9 compared to a reference profile is indicative of spinal inflammation and ankylosis in a B27+ female. In some embodiments, elevated measured level of LCN2 compared to a reference profile is indicative of joint inflammation. In some embodiments, elevated measured level of LCN2 compared to a reference profile is indicative of joint inflammation in a female subject having near fused spine. In some embodiments, elevated measured level of LCN2 compared to a reference profile is indicative of joint inflammation in a male subject having near fused spine. In some embodiments, the reference profile is LCN2normalLCN2-MMP9normal-OSMnormal, LCN2normalLCN2-MMP9elevatedOSMnormal, LCN2elevatedLCN2-MMP9-normalOSMnormal, or LCN2elevatedLCN2-MMP9elevatedOSMnormal. In some embodiments, the reference profile is LCN2normalLCN2-MMP9normalOSMnormal. In some embodiments, the reference profile is LCN2normalLCN2-MMP9elevatedOSMnormal. In some embodiments, the reference profile is LCN2elevatedLCN2-MMP9-normalOSMnormal. In some embodiments, the reference profile is LCN2elevatedLCN2-MMP9-elevatedOSMnormal.

In some embodiments, the subject is male having elevated measured levels of LCN2, LCN2-MMP9 and OSM compared to a reference profile. In some embodiments, the subject is a B27+ male. In some embodiments, the subject is a B27− male. In some embodiments, the subject is a B27− male having elevated measured levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is female having elevated measured levels of LCN2, LCN2-MMP9 and OSM compared to a reference profile. In some embodiments, the subject is a B27+ female. In some embodiments, the subject is a B27− female. In some embodiments, the subject is a B27− female having elevated measured levels of LCN2 and OSM compared to a reference profile. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA. In some embodiments, the method for monitoring clinical disease activity, treatment response, disease progression, active repair, and/or predicting risk of developing a disease determines an axSpA disease state in a subject by a method described herein.

Another aspect of the present disclosure is a method of determining an axSpA disease state in a subject, the method comprising:

- measuring in vitro a level of lipocalin2 (LCN2), a level of LCN2-Matrix metallopeptidase 9 heterodimer (LCN2-MMP9), and/or a level of oncostatin M (OSM) in a sample obtained from the subject;
- comparing the measured level of LCN2, LCN2-MMP9, and/or OSM to level in a previous sample and/or one or more reference profile; and determining the axSpA disease state according to the similarity of the measured level and/or pattern of LCN2, LCN2-MMP9, and/or OSM compared to the previous sample and/or compared to the one or more reference.

In some embodiments, the subject has axSpA. In some embodiments, the subject is suspected to have axSpA. In some embodiments, the disease state early manifests clinically as chronic back pain extending >3 months duration or the following phase in which changes of inflammation can be detected with MRI or subsequent phases in which conventional x-ray images show new bone formation in the spine and/or sacroiliacjoint (SIJ) deterioration and changes toward fusion. In some embodiments, the methods are for early monitoring of disease. In some embodiments, the early monitoring of disease is by the classification criteria from the Assessment of Spondylo Arthritis international Society (ASAS) group as described in Manica SR 2020, herein incorporated by reference. In some embodiments, the methods are for early monitoring of disease in a subject with chronic back pain without or before detection of MRI and CRP changes. Classification diagnosis criteria for axial spondyloarthritis under ASAS include >3 months back pain and age at onset <45 years, sacroiliitis on imaging+>1 SpA feature (out of 11), 2 SpA feature (out of 11), optionally radiography and MRI, inflammatory markers such as CRP, Human leukocyte antigen [HLA]-B27 positive. The ASAS criteria allow classification as pSpA or axSpA, where axSpA is classified into imaging or clinical arm, and axSpA imaging arm can be further classified as r-axSpA versus nr-axSpA.

In some embodiments, the sample is a blood sample. In some embodiments, the sample is a serum sample. In some embodiments, the sample is a plasma sample.

Any suitable method for detecting and/or measuring protein expression may be used in the methods described herein. Suitable methods include, without limitation, ELISA, protein microarray, and mass spectroscopy. Accordingly, in some embodiments, the method is ELISA, protein microarray, and/or mass spectroscopy. In some embodiments, the method is ELISA. In some embodiments, the ELISA assay for LCN2 shows no cross reactivity with MMP9 and does not measure LCN2-MMP9. In some embodiments, the ELISA assay LCN2-MMP9 shows no cross reactivity with LCN2 monomers or LCN2 homodimers. In some embodiments, the sample is a blood sample. In some embodiments, the sample is a serum sample. In some embodiments, the sample is a plasma sample.

In some embodiments, the measurement comprises contacting the sample with one or more detectable binding agents that specifically bind to the one or more biomarkers and detecting specific binding between the specific binding agent(s) and the biomarker(s) using a detection assay comprising biomarker controls. The skilled person recognizes that a standard curve constructed with different concentrations of LCN2, LCN2-MMP9, or OSM is used in each ELISA assay to determine the level, in weight concentration units such as mg/mL, ng/mL, or pg/mL, or another suitable unit.

The measured level of LCN2, LCN2-MMP9 and/or OSM in a sample obtained from the subject is compared to the level of LCN2, LCN2-MMP9, and/or OSM in a previous sample, one or more reference profiles, or both a previous sample and one or more reference profiles. For example, the measured level in the sample obtained from the subject can be compared to a previous sample to confirm if the sample obtained from the subject exhibits persistent or transient elevation, and the measured level can be compared to a reference profile that may comprise a cut-off value or range indicative of whether the measured level is elevated or normal and/or pattern parameters, e.g. persistent or transient, indicative of whether said pattern is associated with clinical disease activity, treatment response, disease progression, and/or active repair.

In some embodiments, the reference profile is one or more of LCN2elevatedOSMnormal, LCN2elevatedOSMelevated, LCN2normalOSMelevated or LCN2normalOSMnormal, LCN2elevatedLCN2-MMP9normalOSMnormal, LCN2elevatedLCN2-MMP9elevatedOSMnormal, LCN2elevatedLCN2-MMP9normalOSMelevated, LCN2elevatedLCN2-MMP9elevatedOSMelevated, LCN2normalLCN2-MMP9elevatedOSMnormal, LCN2normalLCN2-MMP9elevatedOSMelevated, LCN2normalLCN2-MMP9normalOSMelevated, LCN2normalLCN2-MMP9normalOSMnormal, where the reference profile comprises a cut off value or range for the protein expression of each LCN2, LCN2-MMP9, and/or OSM which is indicative of either a normal or elevated level. In some embodiments, the reference profile comprises a cut off value or range for the protein expression of each LCN2, LCN2-MMP9, and/or OSM which is indicative of either a normal or elevated level based on a preselected degree of specificity and sensitivity.

In some embodiments, the reference profile comprises pattern values. In some embodiments, the pattern of expression for a biomarker exhibiting an elevated measured level of protein expression is persistently elevated or transiently elevated. In some embodiments, the reference profile is one or more of LCN2 transient OSM transient (LCN2tOSMt), LCN2 persistent OSM transient (LCN2pOSMt), LCN2 persistent OSM persistent (LCN2pOSMp), LCN2 transient OSM persistent (LCN2tOSMp), LCN2 transient LCN2-MMP9 transient OSM transient (LCN2tLCN2-MMP9tOSMp), LCN2 transient LCN2-MMP9 transient OSM persistent (LCN2tLCN2-MMP9tOSMp), LCN2 transient LCN2-MMP9 persistent OSM transient (LCN2tLCN2-MMP9pOSMt), LCN2 transient LCN2-MMP9 persistent OSM persistent (LCN2tLCN2-MMP9pOSMp), LCN2 persistent LCN2-MMP9 transient OSM transient (LCN2pLCN2-MMP9tOSMt), LCN2 persistent LCN2-MMP9 persistent OSM transient (LCN2pLCN2-MMP9pOSMt), LCN2 persistent LCN2-MMP9 transient OSM persistent (LCN2pLCN2-MMP9tOSMp), or LCN2 persistent LCN2-MMP9 persistent OSM persistent (LCN2pLCN2-MMP9pOSMp).

In some embodiments, the LCN2elevatedOSMnormal is LCN transient (LCN2tOSMn). In some embodiments, the LCN2elevatedOSMnormal is LCN persistent (LCN2pOSMn).

In some embodiments, the LCN2normalOSMelevated is OSM transient (LCN2nOSMt). In some embodiments, the LCN2normalOSMelevated is OSM persistent (LCN2nOSMp).

In some embodiments, the LCN2elevatedOSMelevated is LCN2 transient OSM transient (LCN2tOSMt). In some embodiments, the LCN2elevatedOSMelevated is LCN2 transient OSM persistent (LCN2tOSMp). In some embodiments, the LCN2elevatedOSMelevated is LCN2 persistent OSM transient (LCN2pOSMt). In some embodiments, the LCN2elevatedOSMelevated is LCN2 persistent OSM persistent (LCN2pOSMp).

In some embodiments, the LCN2elevatedLCN2-MMP9normalOSMnormal is LCN2 transient (LCN2tLCN2-MMP9nOSMn). In some embodiments, the LCN2elevatedLCN2-MMP9normalOSMnormal is LCN2 persistent (LCN2pLCN2-MMP9nOSMn).

In some embodiments, the LCN2elevatedLCN2-MMP9elevatedOSMnormal is LCN2 transient LCN-MMP9 transient (LCN2tLCN2-MMP9tOSMn). In some embodiments, the LCN2elevatedLCN2-MMP9elevatedOSMnormal is LCN2 transient LCN-MMP9 persistent (LCN2tLCN2-MMP9pOSMn). In some embodiments, the LCN2elevatedLCN2-MMP9elevatedOSMnormal is LCN2 persistent LCN-MMP9 transient (LCN2pLCN2-MMP9tOSMn). In some embodiments, the LCN2elevatedLCN2-MMP9elevatedOSMnormal is LCN2 persistent LCN-MMP9 persistent (LCN2pLCN2-MMP9pOSMn).

In some embodiments, the LCN2elevatedLCN2-MMP9normalOSMelevated is LCN2 transient OSM transient (LCN2tLCN2-MMP9nOSMt). In some embodiments, the LCN2elevatedLCN2-MMP9normalOSMelevated is LCN2 transient OSM persistent (LCN2tLCN2-MMP9nOSMp). In some embodiments, the LCN2elevatedLCN2-MMP9normalOSMelevated is LCN2 persistent OSM transient (LCN2pLCN2-MMP9nOSMt). In some embodiments, the LCN2elevatedLCN2-MMP9normalOSMelevated is LCN2 persistent OSM persistent (LCN2pLCN2-MMP9nOSMp).

In some embodiments, the LCN2elevatedLCN2-MMP9elevatedOSMelevated is LCN2 transient LCN2-MMP9 transient OSM transient (LCN2tLCN2-MMP9tOSMt). In some embodiments, the LCN2elevatedLCN2-MMP9elevatedOSMelevated is LCN2 transient LCN2-MMP9 persistent OSM transient (LCN2tLCN2-MMP9pOSMt). In some embodiments, the LCN2elevatedLCN2-MMP9elevatedOSMelevated is LCN2 transient LCN2-MMP9 transient OSM persistent (LCN2tLCN2-MMP9tOSMp). In some embodiments, the LCN2elevatedLCN2-MMP9elevatedOSMelevated is LCN2 transient LCN2-MMP9 persistent OSM persistent (LCN2tLCN2-MMP9pOSMp). In some embodiments, the LCN2elevatedLCN2-MMP9elevatedOSMelevated is LCN2 persistent LCN2-MMP9 transient OSM transient (LCN2pLCN2-MMP9tOSMt). In some embodiments, the LCN2elevatedLCN2-MMP9elevatedOSMelevated is LCN2 persistent LCN2-MMP9 transient OSM persistent (LCN2pLCN2-MMP9tOSMp). In some embodiments, the LCN2elevatedLCN2-MMP9elevatedOSMelevated is LCN2 persistent LCN2-MMP9 persistent OSM transient (LCN2pLCN2-MMP9pOSMt). In some embodiments, the LCN2elevatedLCN2-MMP9elevatedOSMelevated is LCN2 persistent LCN2-MMP9 persistent OSM persistent (LCN2pLCN2-MMP9pOSMp).

In some embodiments, the LCN2normalLCN2-MMP9elevatedOSMnormal is LCN2-MMP9 transient (LCN2nLCN2-MMP9tOSMn). In some embodiments, the LCN2normalLCN2-MMP9elevatedOSMnormal is LCN2-MMP9 persistent (LCN2nLCN2-MMP9pOSMn).

In some embodiments, the LCN2normalLCN2-MMP9elevatedOSMelevated is LCN2-MMP9 transient OSM transient (LCN2nLCN2-MMP9tOSMt). In some embodiments, the LCN2normalLCN2-MMP9elevatedOSMelevated is LCN2-MMP9 transient OSM persistent (LCN2nLCN2-MMP9tOSMp). In some embodiments, the LCN2normalLCN2-MMP9elevatedOSMelevated is LCN2-MMP9 persistent OSM transient (LCN2nLCN2-MMP9pOSMt). In some embodiments, the LCN2normalLCN2-MMP9elevatedOSMelevated is LCN2-MMP9 persistent OSM persistent (LCN2nLCN2-MMP9pOSMp).

In some embodiments, the LCN2normalLCN2-MMP9normalOSMelevated is OSM transient (LCN2nLCN2-MMP9nOSMt). In some embodiments, the LCN2normalLCN2-MMP9normalOSMelevated is OSM persistent (LCN2nLCN2-MMP9nOSMp).

In some embodiments, a measured level is only compared to reference profile. In some embodiments, the reference profile is a cut-off level. For example, where a subject has been experiencing back pain, or has radiologic findings, etc. indicative of active disease, it is not necessary to compare to a previous sample. It is known in the art that to assess inflammation activity a single time point is indicative, whereas to assess treatment response two or more serial samples are used and not if the markers at a single time point is a real normal and the patient had clinically active disease previously.

In some embodiments, a decrease in measured level of LCN2, LCN2-MMP9, and/or OSM compared to a previous sample and/or compared to one or more reference profiles is indicative of a treatment response. In some embodiments, a decrease in measured level of LCN2, LCN2-MMP9, and/or OSM compared to a previous sample and/or compared to one or more reference profiles is indicative of a good treatment response. For example, when a measured level of LCN2, LCN2-MMP9, and/or OSM is decreased relative to a previous sample, where the previous sample when compared to a reference profile is identified as having elevated measured level of LCN2, LCN2-MMP9, and/or OSM, the subject is having a treatment response. In some embodiments, when a measured level of LCN2, LCN2-MMP9, and/or OSM is decreased relative to a previous sample, where the previous sample when compared to a reference profile is identified as having elevated measured level of LCN2, LCN2-MMP9, and/or OSM, the subject is having a treatment response. In some embodiments, the treatment response is a good treatment response.

In some embodiments, elevated measured level of LCN2 and/or LCN2-MMP9 compared to a reference profile is indicative of clinical disease activity and/or disease progression. In some embodiments, elevated measured level of LCN2 compared to a reference profile is indicative of disease progression. In some embodiments, elevated measured level of LCN2 compared to a reference profile is indicative of spinal radiographic progression. In some embodiments, elevated measured level of LCN2 compared to a reference profile is indicative of spinal inflammation. In some embodiments, elevated measured level of LCN2 compared to a reference profile is indicative of ankylosis. In some embodiments, elevated measured level of LCN2 compared to a reference profile is indicative of spinal inflammation and ankylosis. In some embodiments, elevated measured level of LCN2 and LCN2-MMP9 compared to a reference profile is indicative of spinal inflammation and ankylosis. In some embodiments, elevated measured level of LCN2 and/or LCN2-MMP9 compared to a reference profile is indicative of spinal inflammation and ankylosis in a male subject. In some embodiments, elevated measured level of LCN2 and/or LCN2-MMP9 compared to a reference profile is indicative of spinal inflammation and ankylosis in a female subject. In some embodiments, elevated measured level of LCN2 and/or LCN2-MMP9 compared to a reference profile is indicative of spinal inflammation and ankylosis in a B27+ male. In some embodiments, elevated measured level of LCN2 and/or LCN2-MMP9 compared to a reference profile is indicative of spinal inflammation and ankylosis in a B27+ female. In some embodiments, elevated measured level of LCN2 compared to a reference profile is indicative of joint inflammation. In some embodiments, elevated measured level of LCN2 compared to a reference profile is indicative of joint inflammation in a subject having near fused spine. In some embodiments, elevated measured level of LCN2 compared to a reference profile is indicative of joint inflammation in a male subject having near fused spine. In some embodiments, the reference profile is LCN2normalLCN2-MMP9normal-OSMnormal, LCN2normalLCN2-MMP9elevatedOSMnormal, LCN2elevatedLCN2-MMP9-normalOSMnormal, or LCN2elevatedLCN2-MMP9elevatedOSMnormal. In some embodiments, the reference profile is LCN2normalLCN2-MMP9normalOSMnormal. In some embodiments, the reference profile is LCN2normalLCN2-MMP9elevatedOSMnormal. In some embodiments, the reference profile is LCN2elevatedLCN2-MMP9-normalOSMnormal. In some embodiments, the reference profile is LCN2elevatedLCN2-MMP9-elevatedOSMnormal.

In some embodiments, a sample from the subject exhibits level of LCN2 and LCN2-MMP9 similar to a reference profile of a weight ratio of LCN2-MMP9:LCN2 (w/w) of greater than or about 1:1 indicates that the subject has an increased risk of axial spondyloarthritis development. In some embodiments, a sample from the subject exhibits level of LCN2 and LCN2-MMP9 similar to a reference profile LCN2normalLCN2-MMP9normal and a ratio of LCN2-MMP9:LCN2 (w/w) of greater than or about 1:1 indicates that the subject has an increased risk of axial spondyloarthritis development.

In some embodiments, the subject is female. In some embodiments, the subject is male. In some embodiments, the subject is male having elevated measured levels of LCN2, LCN2-MMP9 and OSM compared to a reference profile. In some embodiments, the subject is a B27+ male. In some embodiments, the subject is a B27− male. In some embodiments, the subject is a B27− male having elevated measured levels of LCN2 and OSM compared to a reference profile. In some embodiments, the subject is a B27+ female. In some embodiments, the subject is a B27− female. In some embodiments, the subject is a B27− female having elevated measured levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA. [00184] r-axSpA patients are recommended to be assessed periodically, for example, every 6-12 months. Ordinarily the standard follow-up time for patients is every 12 months unless there is significant increase in clinical disease activity such as back pain, onset of new comorbidities or intercurrent infections, which would occasion more frequent assessments.

Accordingly, in some embodiments of the disclosure, a sample is obtained from a subject having stable disease about every 6 months to about every 12 months. In some embodiments, a sample is obtained from a subject having stable disease about every 6 months, about every 7 months, about every 8 months, about every 9 months, about every 10 months, about every 11 months, or about every 12 months. In some embodiments, a sample is obtained from a subject having increased clinical disease activity about every 1 month to about every 3 months. In some embodiments, a sample is obtained from a subject having increased clinical disease activity about every month, about every 2 months, about every 3 months, about every six weeks, or about every nine weeks. In some embodiments, the level of lipocalin2 (LCN2), the level of LCN2-Matrix metallopeptidase 9 heterodimer (LCN2-MMP9), and/or the level of oncostatin M (OSM) is measured from a sample obtained from a subject having stable disease or increased clinical disease activity.

In some embodiments, the subject is receiving treatment for axial spondyloarthritis. In some embodiments, treatment for axial spondyloarthritis is or comprises NSAIDs, DMARDs, TNFi, IL17i, or a combination thereof. In some embodiments, treatment for axial spondyloarthritis is or comprises IL17i.

In some embodiments, the sample is taken after initiation of treatment and the measured level of LCN2, LCN2-MMP9, and/or OSM is compared to a previous sample taken prior to the initiation of treatment. In other embodiments, both the previous sample and the sample are obtained after initiation of treatment.

The methods can also include a step of obtaining the sample.

In some embodiments, an increased or similar measured level of LCN2, LCN2-MMP9, and/or OSM compared to the previous sample and/or one or more reference profiles wherein the previous sample and/or the reference profile comprises or is an elevated measured level of LCN2, LCN2-MMP9, and/or OSM containing sample or reference profile, indicates that the subject is not responding to the treatment.

If a subject is experiencing disease progression or is not responding to treatment, the subject may be treated. For example, if the subject is receiving a treatment, and not responding, the treatment can be altered. Accordingly, also provided is a method for providing a treatment plan, the method comprising monitoring clinical disease activity, treatment response, disease progression, and/or active repair according to a method described herein, and providing a treatment plan based on the measured levels. In some embodiments, the method for providing a treatment plan for a subject having axSpA undergoing a treatment comprises:

measuring in vitro concentration of lipocalin2 (LCN2) and concentration of LCN2-Matrix metallopeptidase 9 heterodimer (LCN2-MMP9) in a sample obtained from the subject;

determining the weight ratio of the concentration of LCN2 to the concentration of LCN2-MMP9 in the sample;

wherein if the concentration of LCN2 and LCN2-MMP9 are within normal limit, and the weight ratio of the concentration of LCN2 to the concentration of LCN2-MMP9 is between about 0.8 and about 1.2, it is indicative of the subject having disease activity fluctuation, and if it is indicative that the subject is having disease activity fluctuation, the treatment plan comprises administration of an alternative treatment.

In some embodiments, the sample is a blood sample. In some embodiments, the sample is a serum sample. In some embodiments, the sample is a plasma sample. In some embodiments, the normal limit of the concentration of LCN2 is up to about 150 ng/mL. In some embodiments, the normal limit of the concentration of LCN2-MMP2 is up to about 100 ng/mL.

In some embodiments, the alternative treatment is an increase dose of a treatment the subject is undergoing. In some embodiments, the alternative treatment is addition or removal of an agent or therapy from a combination of treatment the subject is undergoing. In some embodiments, the alternative treatment is a different agent or therapy from the treatment the subject is undergoing. In some embodiments, the subject is undergoing treatment comprising an analgesic, an NSAID and/or an anti-inflammatory agent, and the alternative treatment is any alternative treatment described herein. In some embodiments, the alternative treatment is or comprises a biologic. In some embodiments, the alternative treatment is or comprises an anti-inflammatory therapy, an anti-inflammatory agent, an anti-fibrotic therapy, or an anti-fibrotic agent.

In some embodiments, the alternative treatment is or comprises an anti-inflammatory therapy. In some embodiments, the anti-inflammatory therapy is or comprises inhibition or promotion of innate lymphoid cells. In some embodiments, the alternative treatment is an anti-inflammatory agent. In some embodiments, the anti-inflammatory agent is or comprises a nonsteroidal anti-inflammatory drug. In some embodiments, the anti-inflammatory agent is or comprises a tumor necrosis factor alpha (TNF-alpha) inhibitor. In some embodiments, the TNF-alpha inhibitor comprises adalimumab, certolizumab, etanercept, golimumab, infliximab, or a combination thereof. In some embodiments, the anti-inflammatory agent is or comprises a tumor necrosis factor alpha (TNF-alpha) inhibitor.

In some embodiments, the anti-inflammatory agent lacks a TNF-alpha inhibitor. In some embodiments, the subject was previously receiving a TNF alpha inhibitor.

In some embodiments, the anti-inflammatory agent is or comprises an interleukin 17 (IL-17) inhibitor. In some embodiments, the anti-inflammatory agent is or comprises a biological response modifier such as a cytokine inhibitor. In some embodiments, the cytokine inhibitor is or comprises an interleukin-12 (IL-12) inhibitor, IL-17 inhibitor, or an IL-23 inhibitor. In some embodiments, the IL-12 inhibitor is ustekinumab. In some embodiments, the IL-17 inhibitor is secukinumab. In some embodiments, the IL-23 inhibitor is briakinumab. In some embodiments, the anti-inflammatory agent is or comprises a biological response modifier downstream of cytokine signaling. In some embodiments, the response modifier downstream of cytokine signaling is a Janus kinase (JAK) inhibitor. In some embodiments, the JAK inhibitor comprises baricitinib, tofacitinib, upadacitinib, ruxolitinib, fedratinib, or a combination thereof.

Anti-fibrotic therapy or anti-fibrotic agent can also be an alternative treatment for axial spondyloarthritis. In some embodiments, the alternative treatment is or comprises an anti-fibrotic therapy. In some embodiments, the anti-fibrotic therapy is or comprises inhibition of nonreceptor tyrosine kinases and/or receptor tyrosine kinases. In some embodiments, the anti-fibrotic therapy is or comprises inhibition of fibroblast proliferation, transforming growth factor beta stimulated collagen production, and/or fibrogenic mediators production. In some embodiments, the alternative treatment is or comprises an anti-fibrotic agent. In some embodiments, the anti-fibrotic agent is or comprises nintedanib or pirfenidone. In some embodiments, the anti-fibrotic agent is or comprises nintedanib. In some embodiments, the anti-fibrotic agent is or comprises pirfenidone.

In some embodiments, the subject is female. In some embodiments, the subject is male. In some embodiments, the subject is male having elevated measured levels of LCN2, LCN2-MMP9 and OSM compared to a reference profile. In some embodiments, the subject is a B27+ male. In some embodiments, the subject is a B27− male. In some embodiments, the subject is a B27+ female. In some embodiments, the subject is a B27− female.

Another aspect of the present disclosure is a method of treating a subject with axial spondyloarthritis, the method comprising:

a) administering to the subject a suitable treatment, optionally an anti-inflammatory therapy, an anti-inflammatory agent, an anti-fibrotic therapy, or an anti-fibrotic agent, when a sample from the subject exhibits a lipocalin 2 (LCN2), LCN2-Matrix metallopeptidase 9 heterodimer (LCN2-MMP9) elevation, and/or oncostatin M (OSM) elevation or pattern (e.g. persistence or transience) compared to a previous sample and/or one or more reference profiles; or b) i) monitoring clinical disease activity, treatment response, disease progression, and/or active repair in the subject using a method described herein; and ii) administering to the subject a suitable treatment, optionally an anti-inflammatory therapy, an anti-inflammatory agent, an anti-fibrotic therapy, or an anti-fibrotic agent, when a sample from the subject exhibits an LCN2, LCN2-MMP9, and/or OSM elevation compared to a previous sample and/or a pattern (e.g. persistence or transience) similar to one or more reference profiles, optionally wherein the treatment is administered until the level of LCN2, LCN2-MMP9, and/or OSM is decreased or about normal.

In some embodiments, the axial spondyloarthritis is r-axSpA. In some embodiments, the axial spondyloarthritis is nr-axSpA. In some embodiment, the sample from the subject exhibits an LCN2, LCN2-MMP9, and/or OSM elevation compared to a previous sample. In some embodiments, the pattern is transient elevation of the level of LCN2, LCN2-MMP9, and/or OSM similar to the one or more reference profiles. In some embodiments, the pattern is persistent elevation of the level of LCN2, LCN2-MMP9, and/or OSM similar to one or more reference profiles. In some embodiments, the suitable treatment is or comprises an anti-inflammatory therapy. In some embodiments, the anti-inflammatory therapy is or comprises inhibition or promotion of innate lymphoid cells.

In some embodiments, the suitable is or comprises a biologic. In some embodiments, the suitable treatment is an anti-inflammatory agent. In some embodiments, the anti-inflammatory agent is or comprises a nonsteroidal anti-inflammatory drug. In another embodiment the anti-inflammatory agent is or comprises a tumor necrosis factor alpha (TNF-alpha) inhibitor. In some embodiments, the TNF-alpha inhibitor comprises adalimumab, certolizumab, etanercept, golimumab, infliximab, or a combination thereof.

In some embodiments, the anti-inflammatory agent is or comprises a tumor necrosis factor alpha (TNF-alpha) inhibitor, optionally when the sample exhibits elevated level of LCN2, elevated level of LCN2-MMP9, and/or elevated level of OSM. In some embodiments, the sample exhibits elevated level of LCN2-MMP9. In some embodiments, the anti-inflammatory agent is or comprises a tumor necrosis factor alpha (TNF-alpha) inhibitor when the sample exhibits elevated level of LCN2, elevated level of LCN2-MMP9, and/or elevated level of OSM. In some embodiments, the sample exhibits elevated level of LCN2. In some embodiments, the sample exhibits elevated level of LCN2-MMP9. In some embodiments, the sample exhibits elevated levels of LCN2 and LCN2-MMP9.

In some embodiments, the anti-inflammatory agent lacks a TNF-alpha inhibitor.

In some embodiments, the subject was previously receiving a TNF alpha inhibitor.

In some embodiments, the anti-inflammatory agent is or comprises an interleukin 17 (IL-17) inhibitor.

In some embodiments, the anti-inflammatory agent is or comprises a biological response modifier such as a cytokine inhibitor. In some embodiments, the cytokine inhibitor is or comprises an interleukin-12 (IL-12) inhibitor, IL-17 inhibitor, or an IL-23 inhibitor. In some embodiments, the cytokine inhibitor is or comprises an interleukin-12 (IL-12) inhibitor, IL-17 inhibitor, or an IL-23 inhibitor when the sample exhibits elevated level of LCN2, or elevated level of LCN2 and elevated OSM, or elevated level of LCN2-MMP9 with or without elevated OSM. In some embodiments, the sample exhibits elevated level of LCN2. In some embodiments, the sample exhibits elevated level of LCN2 and elevated OSM. In some embodiments, the sample exhibits elevated level of LCN2-MMP9. In some embodiments, the IL-12 inhibitor is ustekinumab. In some embodiments, the IL-17 inhibitor is secukinumab. In some embodiments, the IL-23 inhibitor is briakinumab. In some embodiments, the anti-inflammatory agent is or comprises a biological response modifier downstream of cytokine signaling. In some embodiments, the response modifier downstream of cytokine signaling is a Janus kinase (JAK) inhibitor. In some embodiments, the JAK inhibitor comprises baricitinib, tofacitinib, upadacitinib, ruxolitinib, fedratinib, or a combination thereof.

Anti-fibrotic therapy or anti-fibrotic agent can be suitable treatment for axial spondyloarthritis. In some embodiments, the suitable treatment is or comprises an anti-fibrotic therapy. In some embodiments, the anti-fibrotic therapy is or comprises inhibition of nonreceptor tyrosine kinases and/or receptor tyrosine kinases. In some embodiments, the anti-fibrotic therapy is or comprises inhibition of fibroblast proliferation, transforming growth factor beta stimulated collagen production, and/or fibrogenic mediators production. In some embodiments, the suitable treatment is or comprises an anti-fibrotic agent. In some embodiments, the anti-fibrotic agent is or comprises nintedanib or pirfenidone. In some embodiments, the anti-fibrotic agent is or comprises nintedanib. In some embodiments, the anti-fibrotic agent is or comprises pirfenidone.

In some embodiments, the suitable treatment is administered by injection or infusion. For example, the suitable treatment can be administered systemically, orally, subcutaneously or intravenously. In some embodiments, NSAIDs are administered orally. In some embodiments, DMARDS are administered orally, subcutaneously or intravenously. In some embodiments, cytokine inhibitor is administered intravenously or subcutaneously. In some embodiments, TNFi is administered intravenously or subcutaneously. In some embodiments, IL17i is administered intravenously or subcutaneously. In some embodiments, nintedanib is administered orally. In some embodiments, pirfenidone is administered orally.

The suitable treatment can be an altered treatment. For example in embodiments where the subject is receiving a treatment and the methods suggest the subject is not responding to treatment, the subject may be administered an altered treatment. For example, if the sample exhibits LCN2normal LCN2-MMP9normal OSMp pattern and the subject is receiving anti-inflammatory treatment, the administering can comprise administering an increased dosage of the anti-inflammatory agent the subject was already receiving or the anti-inflammatory agent administered is a different agent or therapy from the anti-inflammatory treatment the subject was already receiving, for example, an anti-fibrotic therapy or an anti-fibrotic agent.

The suitable treatment can be administered prior to the subject exhibits spondyloarthritis related pain or while the subject exhibits spondyloarthritis related pain. In some embodiments, the subject does not exhibit axial spondyloarthritis related pain. In some embodiments, the suitable treatment is administered to the subject prior to and/or while the subject exhibits axial spondyloarthritis related pain. In some embodiments, the suitable treatment is administered to the subject prior to the subject exhibits axial spondyloarthritis related pain.

In some embodiments, the method further comprises assessing a back pain score. Back pain scores as described by the patient serve as the key clinical decision-making criterion for treatment. A significant increase in back pain currently is the main reason to change ongoing treatment. All current treatments have analgesic effects (more so in some treatments such as TNFi). Accordingly, in some embodiments, assessing back pain score is done with a self-reported BASDAI questionnaire.

In some embodiments, the subject is clinically quiescent (e.g., not exhibiting symptoms of worsening back pain or flare up) when the sample is taken. In some embodiments, the clinically quiescent subject does not exhibit symptoms of worsening back pain or flare up. In some embodiments, the subject is exhibiting back pain or back pain flare up when the sample is taken.

In some embodiments, the sample exhibits normal measured LCN2, LCN2-MMP9, and/or OSM and the subject exhibits back pain, thereby indicating a source of pain other than axSpA. In some embodiments, the method further comprises subjecting the subject to additional tests when the sample exhibits normal measured LCN2 and OSM indicative of a source of pain other than axSpA.

In some embodiments, the subject has either non-radiographic axSpA (nr-axSpA or radiographic axSpA (r-axSpA; also known as ankylosing spondylitis (AS)). In some embodiments, the subject has nr-axSpA.

In some embodiments, the subject has r-axSpA. In some patients, nr-axSpA can progress to r-axSpA with increase in disease duration. Accordingly, in some embodiments, the subject has nr-axSpA progressed to r-axSpA. In some embodiments, the subject has recently been diagnosed with r-axSpA.

In some embodiments, the subject is also afflicted with inflammatory bowel disease (IBD) including ulcerative colitis (UC) or Crohn's disease (CD).

In some embodiments, the subject is female. In some embodiments, the subject is male. In some embodiments, the subject is male having elevated levels of LCN2, LCN2-MMP9 and OSM compared to a reference profile. In some embodiments, the subject is a B27+ male. In some embodiments, the subject is a B27− male. In some embodiments, the subject is a B27− male having elevated levels of LCN2 and OSM compared to a reference profile. In some embodiments, the subject is a B27+ female. In some embodiments, the subject is a B27− female. In some embodiments, the subject is a B27− female having elevated measured levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA.

Treatment does not begin, put on hiatus, or can cease if the biomarkers described herein are, or have decreased to, levels within normal limits that are indicative of no elevated local inflammation. Conversely, treatment begins or restarts if biomarkers level outside of normal limits that indicative of elevated local inflammation. In some embodiments, no treatment is administered when a sample from the subject exhibits concentration of LCN2-MMP9 at less than about 50 ng/mL, LCN2 at less than about 100 ng/ml, and OSM at less than about 50 pg/mL, which is indicative of no elevated local inflammation. In some embodiments, no treatment is administered when a sample from the subject exhibits concentration of LCN2-MMP9 at less than about 50 ng/mL, LCN2 at less than about 100 ng/ml, OSM at less than about 50 pg/mL, and a weight ratio of concentration of LCN2 to concentration of LCN2-MMP9 is at least about 1.2:1, which is indicative of no elevated local inflammation. In some embodiments, the weight ratio of concentration of LCN2 to concentration of LCN2-MMP9 is between about 1.2:1 to about 5:1. In some embodiments, a treatment is administered when a sample from the subject exhibits concentration of LCN2-MMP9 at between about 51 ng/mL and about 100 ng/mL, LCN2 at between about 101 ng/mL and about 150 ng/ml, and OSM at about 50 pg/mL, which is indicative of slightly elevated local inflammation. In some embodiments, a treatment is administered when a sample from the subject exhibits concentration of LCN2-MMP9 at between about 101 ng/mL and about 200 ng/mL, LCN2 at between about 150 and about 250 ng/ml, and OSM at between about 50 and about 500 pg/mL, which is indicative of elevated local inflammation. In some embodiments, a treatment is administered when a sample from the subject exhibits concentration of LCN2-MMP9 at great than about 200 ng/mL, LCN2 at greater than about 250 ng/ml, and OSM at greater than about 500 pg/mL, which is indicative of high local inflammation. In some embodiments, the treatment is or comprises a biologic. In some embodiments, the treatment is or comprises an anti-inflammatory therapy, an anti-inflammatory agent, an anti-fibrotic therapy, or an anti-fibrotic agent described herein.

In some embodiments, no treatment is administered when a sample from the subject exhibits concentration of LCN2-MMP9 at less than about 50 ng/mL, LCN2 at less than about 100 ng/ml, OSM at less than about 50 pg/mL, and a weight ratio of concentration of LCN2 to concentration of LCN2-MMP9 is greater than about 2:1 or a molar ratio of concentration of LCN2 to concentration of LCN2-MMP9 is great than about 6:1, which is indicative of no elevated active chronic inflammation and/or no elevated risk for resistance to anti-inflammatory therapy. In some embodiments, a treatment is administered when a sample from the subject exhibits concentration of LCN2-MMP9 at between about 51 ng/mL and about 100 ng/mL, LCN2 at between about 101 ng/mL and about 150 ng/ml, OSM at about 50 pg/mL, and a molar ratio of concentration of LCN2 to concentration of LCN2-MMP9 is between about 5:1 and about 6:1, which is indicative of slightly elevated active chronic inflammation and/or slightly elevated risk for resistance to anti-inflammatory therapy. In some embodiments, a treatment is administered when a sample from the subject exhibits concentration of LCN2-MMP9 at between about 101 ng/mL and about 200 ng/mL, LCN2 at between about 150 ng/mL and about 250 ng/ml, OSM at between about 50 ng/mL and about 500 pg/mL, and a molar ratio of concentration of LCN2 to concentration of LCN2-MMP9 is between about 4:1 and about 5:1, which is indicative of elevated active chronic inflammation and/or risk for resistance to anti-inflammatory therapy. In some embodiments, a treatment is administered when a sample from the subject exhibits concentration of LCN2-MMP9 at great than about 200 ng/mL, LCN2 at greater than about 250 ng/ml, OSM at greater than 500 pg/mL, and a weight ratio of concentration of LCN2 to concentration of LCN2-MMP9 is less than about 1:1 or a molar ratio of concentration of LCN2 to concentration of LCN2-MMP9 is less than about 4:1, which is indicative of highly active chronic inflammation and/or high risk for resistance to anti-inflammatory therapy. In some embodiments, the treatment is or comprises a biologic. In some embodiments, the treatment is or comprises an anti-fibrotic therapy or an anti-fibrotic agent described herein.

In some embodiments, no treatment is administered when a sample from the subject exhibits concentration of LCN2-MMP9 at less than about 70 ng/mL and OSM is not detectable, which is indicative of low progression probability towards fibrosis, spine neo-ossification and/or ankylosis. In some embodiments, a treatment is administered when a sample from the subject exhibits concentration of LCN2-MMP9 at between about 71 ng/mL and about 100 ng/mL and OSM at less than about 100 pg/mL, which is indicative of slightly elevated progression probability towards fibrosis, spine neo-ossification and/or ankylosis. In some embodiments, a treatment is administered when a sample from the subject exhibits concentration of LCN2-MMP9 at between about 101 ng/mL and about 150 ng/mL, OSM at between about 101 pg/mL and about 999 pg/mL, and a molar ratio of concentration of LCN2 to concentration of LCN2-MMP9 is less than about 1:1, which is indicative of elevated progression probability towards fibrosis, spine neo-ossification and/or ankylosis. In some embodiments, a treatment is administered when a sample from the subject exhibits concentration of LCN2-MMP9 at great than about 151 ng/mL, LCN at less than about 50 ng/mL, OSM at greater than about 1000 pg/mL, and a weight ratio of concentration of LCN2 to concentration of LCN2-MMP9 is less than about 1:1, which is indicative of high progression probability towards fibrosis. In some embodiments, a treatment is administered when a sample from the subject exhibits concentration of LCN2-MMP9 at greater than about 151 ng/mL, LCN at less than about 50 ng/mL, and a weight ratio of concentration of LCN2 to concentration of LCN2-MMP9 is less than about 0.5:1, which is indicative of high progression probability towards fibrosis, spine neo-ossification and/or ankylosis. In some embodiments, the weight ratio of concentration of LCN2 to concentration of LCN2-MMP9 is less than about 0.4:1, 0.3:1, 0.25:1, 0.2:1, 0.15:1, 0.1:1, or 0.05:1. In some embodiments, the treatment is or comprises a biologic. In some embodiments, the treatment is or comprises an anti-fibrotic therapy or an anti-fibrotic agent described herein.

Another aspect of the present disclosure is a method of assessing chronic inflammation, the method comprising:

- measuring in vitro a level of lipocalin2 (LCN2), a level of LCN2-Matrix metallopeptidase 9 heterodimer (LCN2-MMP9), and a level of oncostatin M (OSM) in a sample obtained from the subject; and
- comparing the measured level of LCN2, LCN2-MMP9 and OSM to level in a previous sample and/or one or more reference profiles;
- wherein a differential in the measured level of LCN2, LCN2-MMP9, and/or OSM compared to the previous sample, a differential in the measured level of LCN2, LCN2-MMP9, and/or OSM compared to the one or more reference profiles or thresholds, or a pattern (e.g. persistence or transience) of the measured level of LCN2, LCN2-MMP9, and/or OSM similar to the one or more reference profiles, is indicative of ongoing chronic inflammation.

In some embodiments, the differential in the measured level of LCN2, LCN2-MMP9, and/or OSM compared to the previous sample and/or one or more reference profiles or thresholds is an elevation in the measured level of LCN2, LCN2-MMP9, and/or OSM compared to the previous sample and/or one or more reference profiles or thresholds. In some embodiments, the pattern is transient elevation of the measured level of LCN2, LCN2-MMP9, and/or OSM compared to the previous sample and/or one or more reference profiles or thresholds. In some embodiments, the pattern is persistent elevation of the measured level of LCN2, LCN2-MMP9, and/or OSM compared to the previous sample and/or one or more reference profiles or thresholds. In some embodiments, the differential in the measured level of LCN2, LCN2-MMP9, and/or OSM compared to the previous sample, or the differential in the measured level of LCN2, LCN2-MMP9, and/or OSM compared to the one or more reference profiles or thresholds, is elevated measured level of LCN2, LCN2-MMP9, and/or OSM compared to the previous sample, or elevated measured level of LCN2, LCN2-MMP9, and/or OSM compared to the one or more reference profiles or thresholds. In some embodiments, elevated measured level of LCN2 and/or LCN2-MMP9 compared to a reference profile or threshold is indicative of chronic axial inflammation. In some embodiments, elevated measured level of LCN2 compared to a reference profile or threshold is indicative of chronic axial inflammation. In some embodiments, elevated measured level of LCN2-MMP9 compared to a reference profile or threshold is indicative of chronic axial inflammation. In some embodiments, elevated measured level of LCN2 and LCN2-MMP9 compared to a reference profile or threshold is indicative of chronic axial inflammation. In some embodiments, the reference profile is LCN2normalLCN2-MMP9normalOSMnormal, LCN2normalLCN2-MMP9elevatedOSM-normal, LCN2elevatedLCN2-MMP9normalOSMnormal, or LCN2elevatedLCN2-MMP9-elevatedOSMnormal. In some embodiments, the reference profile is LCN2normal-LCN2-MMP9normalOSMnormal. In some embodiments, the reference profile is LCN2normalLCN2-MMP9elevatedOSMnormal. In some embodiments, the reference profile is LCN2elevatedLCN2-MMP9-normalOSMnormal. In some embodiments, the reference profile is LCN2elevatedLCN2-MMP9-elevatedOSMnormal. In some embodiments, the reference threshold of LCN2 is about 150 ng/mL. In some embodiments, the reference threshold of LCN2 is about 100 ng/mL. In some embodiments, the reference threshold of LCN2-MMP9 is about 100 ng/mL. In some embodiments, the reference threshold of LCN2-MMP9 is about 50 ng/mL.

In some embodiments, a sample from the subject exhibits level of LCN2 and LCN2-MMP9 similar to a reference profile of a weight ratio of LCN2-MMP9:LCN2 (w/w) of greater than or about 1:1 indicates that the subject has an increased risk of spondyloarthritis development. In some embodiments, a sample from the subject exhibits level of LCN2 and LCN2-MMP9 similar to a reference profile LCN2normalLCN2-MMP9normal and a ratio of LCN2-MMP9:LCN2 (w/w) of greater than or about 1:1 indicates that the subject has an increased risk of spondyloarthritis development. In some embodiments, the spondyloarthritis is axial spondyloarthritis.

In some embodiments, the subject is female. In some embodiments, the subject is male. In some embodiments, the subject is male having elevated measured levels of LCN2, LCN2-MMP9 and OSM compared to a reference profile. In some embodiments, the subject is a B27+ male. In some embodiments, the subject is a B27− male. In some embodiments, the subject is a B27− male having elevated measured levels of LCN2 and OSM compared to a reference profile. In some embodiments, the subject is a B27+ female. In some embodiments, the subject is a B27− female. In some embodiments, the subject is a B27− female having elevated measured levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA.

Another aspect of the present disclosure is a method of treating a subject with an inflammatory disease, comprising:

a) administering to the subject an anti-inflammatory agent when a sample from the subject exhibits a lipocalin 2

(LCN2), LCN2-MMP9, and/or oncostatin M (OSM) elevation compared to a previous sample and/or one or more reference profiles; or b) i) monitoring clinical disease activity, treatment response, disease progression, and/or active repair in the subject according to a method of assessing chronic inflammation described herein; and ii) administering to the subject an anti-inflammatory agent when a sample from the subject exhibits an LCN2, LCN2-MMP9, and/or OSM elevation compared to a previous sample and/or one or more reference profiles, optionally wherein the agent is administered until the level of LCN2, LCN2-MMP9, and/or OSM is decreased or about normal.

In some embodiments, the subject is female. In some embodiments, the subject is male. In some embodiments, the subject is male having elevated levels of LCN2, LCN2-MMP9 and OSM compared to a reference profile. In some embodiments, the subject is a B27+ male. In some embodiments, the subject is a B27− male. In some embodiments, the subject is a B27− male having elevated levels of LCN2 and OSM compared to a reference profile. In some embodiments, the subject is a B27+ female. In some embodiments, the subject is a B27− female. In some embodiments, the subject is a B27− female having elevated levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA.

In some embodiments, the inflammatory disease is inflammatory bowel diseases (IBD). In some embodiments, the IBD is treated with IL17i, IL12/IL23i, or IL23i. In some embodiments, the IBD is treated with IL17i. In some embodiments, the IBD is treated with IL12/IL23i. In some embodiments, the IBD is treated with IL23i.

Another aspect of the present disclosure is a method for predicting risk of spinal ankylosis development in a subject having r-axSpA, the method comprises:

measuring in vitro a level of lipocalin2 (LCN2), a level of LCN2-MMP9 and/or a level of oncostatin M (OSM) in a sample obtained from the subject; and comparing the measured level of LCN2, LCN2-MMP9, and/or OSM to levels in a previous sample and/or one or more reference profile;

wherein the subject having a pattern of measured level of LCN2, LCN2-MMP9, and/or OSM similar to a reference profile of LpLMp, LtLMp, LpLMt, LnLMpOp, or LpLMnOp has an increased risk of spinal ankylosis development.

In some embodiments, the subject having a pattern of measured level of LCN2 and LCN2-MMP9 similarto a reference profile of LpLMp indicates that the subject has an increased risk of spinal ankylosis development. In some embodiments, the subject having a pattern of measured level of LCN2 and LCN2-MMP9 more similar to a reference profile of LtLMp than to a reference profile of LpLMt indicates that the subject has an increased risk of spinal ankylosis development. In some embodiments, the subject having a pattern of measured level of LCN2, LCN2-MMP9, and/or OSM similar to a reference profile of LnLMpOp indicates that the subject has an increased risk of spinal ankylosis development. In some embodiments, the subject having a pattern of measured level of LCN2, LCN2-MMP9, and/or OSM similar to a reference profile of LpLMnOp indicates that the subject has an increased risk of spinal ankylosis development. In some embodiments, the subject is female. In some embodiments, the subject is male. In some embodiments, the subject is a B27+ male. In some embodiments, the subject is a B27− male. In some embodiments, the subject is a B27+ female. In some embodiments, the subject is a B27− female.

Another aspect of the present disclosure is a method for predicting risk of spondyloarthritis in a subject, comprising:

measuring in vitro a level of lipocalin2 (LCN2), a level of LCN2-MMP9, and/or a level of oncostatin M (OSM) in a sample such as a blood, serum, or a plasma sample obtained from the subject; and comparing the measured level of LCN2, LCN2-MMP9, and/or OSM to level in a previous sample and/or one or more reference profiles;

wherein a differential in the measured level of LCN2, LCN2-MMP9, and/or OSM compared to the previous sample, a differential in the measured level of LCN2, LCN2-MMP9, and/or OSM compared to the one or more reference profiles, or a pattern (e.g. persistence or transience) of the measured level of LCN2, LCN2-MMP9, and/or OSM similar to the one or more reference profiles, is indicative of an increased risk of developing spondyloarthritis, and wherein the subject has or suspected of having chronic inflammatory disease such as inflammatory bowel diseases (IBD).

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, the spondyloarthritis is axial spondyloarthritis. In some embodiments, the subject having a measured level of LCN2, LCN2-MMP9, and/or OSM similar to a reference profile of LCN2elevatedLCN2-MMP9normalOSMnormal has an increased risk of developing axial spondyloarthritis. In some embodiment the axial spondyloarthritis is r-axSpA. In some embodiments, the subject is female. In some embodiments, the subject is male. In some embodiments, the subject is male having elevated levels of LCN2, LCN2-MMP9 and OSM compared to a reference profile. In some embodiments, the subject is a B27+ male. In some embodiments, the subject is a B27− male. In some embodiments, the subject is a B27− male having elevated measured levels of LCN2 and OSM compared to a reference profile. In some embodiments, the subject is a B27+ female. In some embodiments, the subject is a B27− female. In some embodiments, the subject is a B27− female having elevated measured levels of LCN2 and OSM compared to a reference profile. In some embodiments, the subject is a B27+ male who has not previously been diagnosed with axSpA. In some embodiments, the subject is a B27+ male who has not previously been diagnosed with r-axSpA. In some embodiments, the subject is a B27+ male who has not previously been diagnosed with nr-axSpA. In some embodiments, the subject is a B27+ female who has not previously been diagnosed with axSpA. In some embodiments, the subject is a B27+ female who has not previously been diagnosed with r-axSpA. In some embodiments, the subject is a B27+ female who has not previously been diagnosed with nr-axSpA.

Another aspect of the present disclosure is a method for predicting risk of inflammatory bowel diseases (IBD) in a subject, comprising:

- measuring in vitro a level of lipocalin2 (LCN2), a level of LCN2-MMP9, and/or a level of oncostatin M (OSM) in a sample such as a blood, serum, or a plasma sample obtained from the subject; and
- comparing the measured level of LCN2, LCN2-MMP9, and/or OSM to level in a previous sample and/or one or more reference profiles;
- wherein a differential in the measured level of LCN2, LCN2-MMP9, and/or OSM compared to the previous sample, a differential in the measured level or pattern of LCN2, LCN2-MMP9, and/or OSM compared to the one or more reference profiles, or a pattern (e.g. persistence or transience) of the measured level of LCN2, LCN2-MMP9, and/or OSM similar to the one or more reference profiles, is indicative of an increased risk of developing IBD, and
- wherein the subject has or suspected of having chronic inflammatory disease such as spondyloarthritis, optionally axial spondyloarthritis.

In some embodiments, the differential in the measured level of LCN2, LCN2-MMP9, and/or OSM compared to the previous sample and/or one or more reference profiles is an elevation in the measured level of LCN2, LCN2-MMP9, and/or OSM compared to the previous sample and/or one or more reference profiles. In some embodiments, the pattern is transient elevation of the measured level of LCN2, LCN2-MMP9, and/or OSM compared to the previous sample and/or one or more reference profiles. In some embodiments, the pattern is persistent elevation of the measured level of LCN2, LCN2-MMP9, and/or OSM compared to the previous sample and/or one or more reference profiles. In some embodiments, the subject having the measured level of LCN2, LCN2-MMP9, and/or OSM similar to a reference profile of LCN2normalLCN2-MMP9elevated, LCN2normalLCN2-MMP9elevatedOSMnormal, LCN2normalLCN2-MMP9elevatedOSMelevated has an increased risk of developing IBD.

In some embodiments, the subject having the measured level of LCN2, LCN2-MMP9, and/or OSM similar to a reference profile of LCN2elevatedlLCN2-MMP9elevatedOSMelevated has an increased risk of developing IBD.

In some embodiments, the subject is female. In some embodiments, the subject is male. In some embodiments, the subject is a B27+ male. In some embodiments, the subject is a B27− male. In some embodiments, the subject is a B27+ female. In some embodiments, the subject is a B27− female.

The following non-limiting Examples are illustrative of the present disclosure:

EXAMPLES

Example 1: Presence of LCN2 (L), LCN2-MMP9 (LM) and OSM (O) Elevation Patterns Either Transient or Persistent in axSpA Patients Annual serial measurements of LCN2, LCN2-MMP9 and OSM levels (over a course of at least 4 years) from 286 patients, revealed two patterns of elevation: persistent or transient. Persistent elevation (p) is arbitrarily defined as elevation of LCN2 (Lp), LCN2-MMP9 (LMp), or OSM (Op) levels which are sustained over a period of at least 2 years. Transient elevation (t) is defined as a single elevation over an observation period >2 years (Lt, LMt and Ot). 43% (123/286) of axSpA patients have involvement of the LCN2 pathway alone (LpLMp, LpLMt, LpLMn, LtLMt, LtLMn). 9% (27/286) have involvement of the OSM pathway alone (Op and Ot). 26% (74/286) have involvement of both pathways. The remaining 22% (62/286) have normal LCN2 and OSM levels (LnOn; Table 1).

TABLE 1

The prevalence of axSpA patients with the involvement of LCN2, LCN2-MMP9, and/or OSM pathways.

| Pathway(s) Involved | axSpA (n) | % |
|---|---|---|
| LCN2 (L) [including LCN2-MMP9 (LM)] | 123 | 43 (123/286) |
| OSM (O) | 27 | 9 (27/286) |
| LCN2 + OSM | 74 | 26 (74/286) |
| Normalized (Ln, LMn, On) | 62 | 22 (62/286) |
| Total cases | 286 | 100 |

Figure 1A:
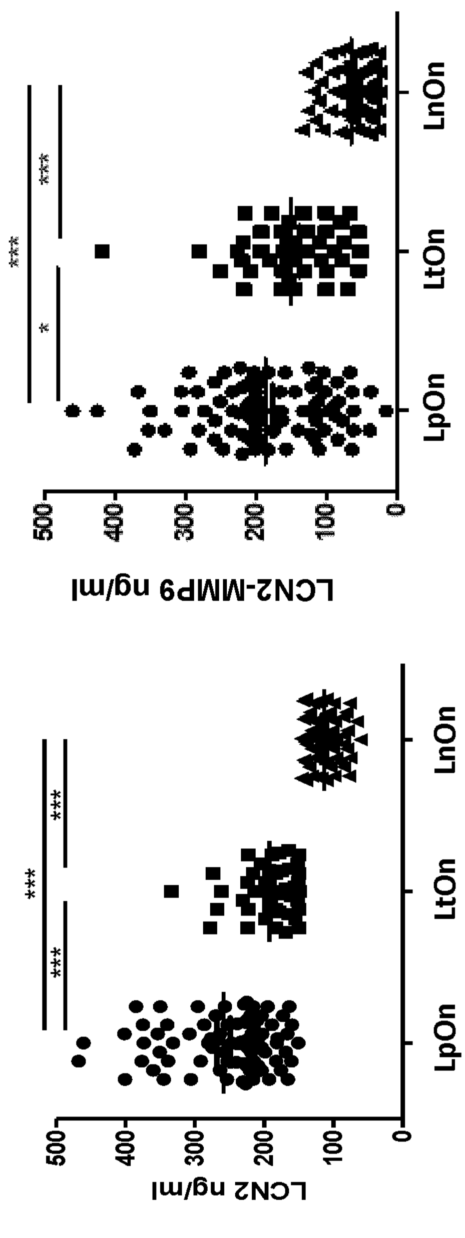

For patients with involvement of LCN2 pathway alone, none had detectable OSM levels (On). Significantly higher LCN2 levels (mean±SE) are found in those with persistent LCN2 (Lp) elevation (LpOn [n=81] vs LtOn [n=41]: 259 ng/ml±9 vs 193 ng/ml±7; p<0.0001). LnOn (n=62) patients have normal LCN2 levels (114 ng/ml±3; 150 ng/ml being the cutoff) and LCN2-MMP9 levels (for example, 66 ng/ml±4; 100 ng/ml being the cutoff) and undetectable OSM levels (FIG. 1A). The skilled person recognizes that to establish high sensitivity, which is desirable in laboratory test, lower limits for healthy reference range are desirable, as laboratory tests can be devised with a category of "may be at risk". In this overall context on a w/w basis, useful cut offs would be LCN2>100 ng/ml, LCN2-MMP-9 >50 ng/ml, and OSM >0.5 pg/ml. About 80% of healthy individuals would be expected to be below these levels.

Figure 1B:
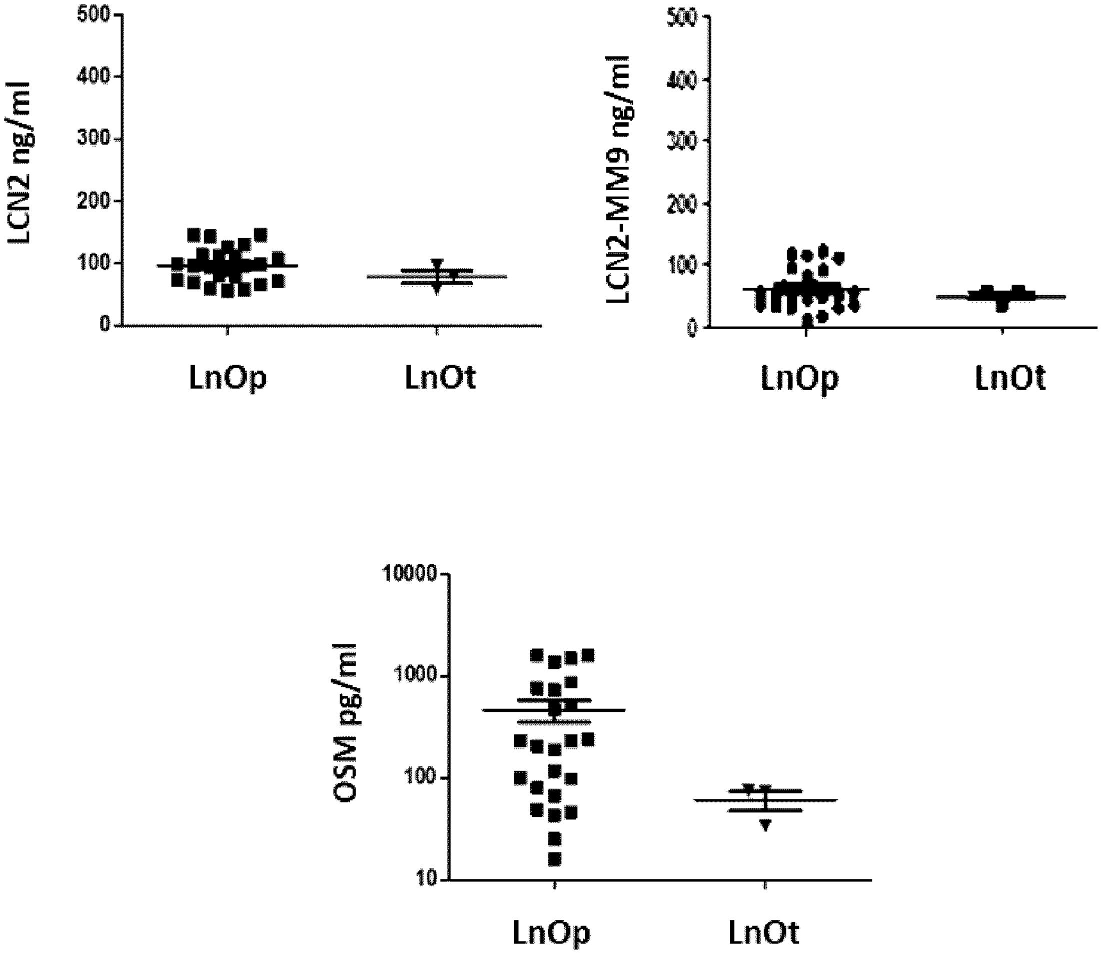

For patients with involvement of OSM pathway alone, all of them have normal LCN2 levels (LnOp [n=24] and LnOt [n=3]: 97 ng/ml±6, and 78 ng/ml±11, respectively) and normal LCN2-MMP9 levels (LnOp and LnOt: 62 ng/ml±7, and 50 ng/ml±6, respectively). Higher OSM levels are found in those with persistent OSM (Op) elevation (LnOp vs LnOt: 463 pg/ml±110 vs 61 pg/ml±14), though the difference is not significantly different. (FIG. 1B).

Figure 2A:
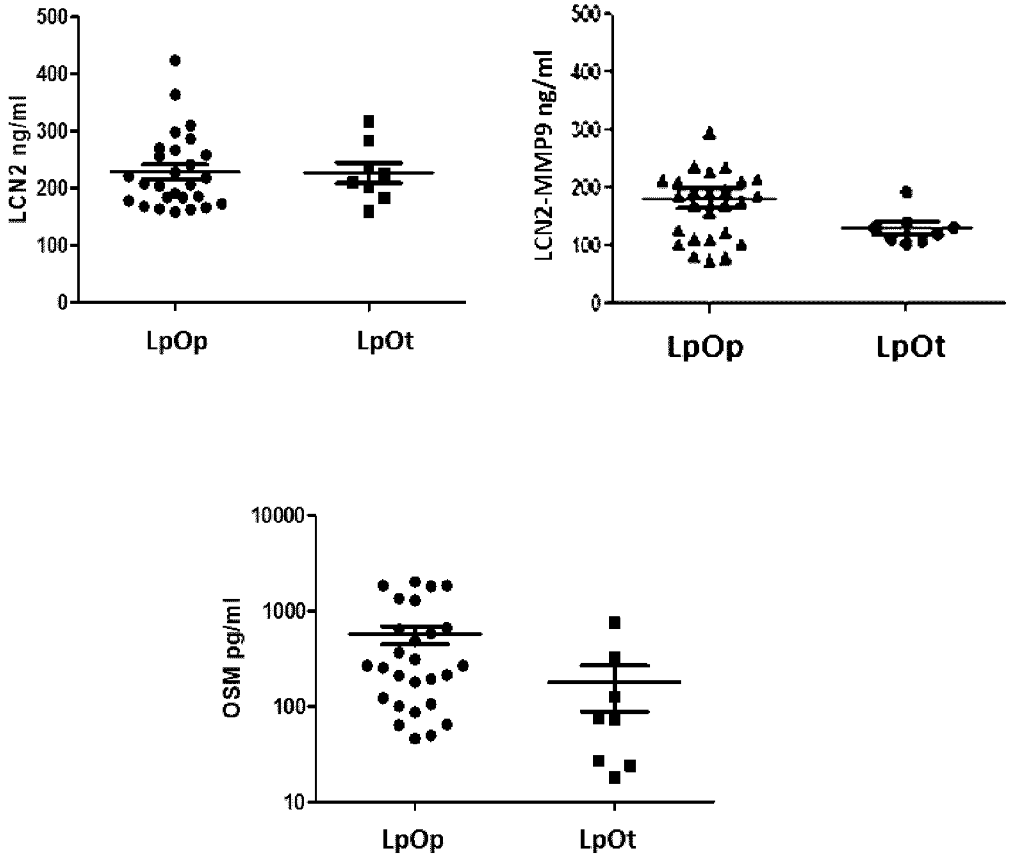
Figure 2B:
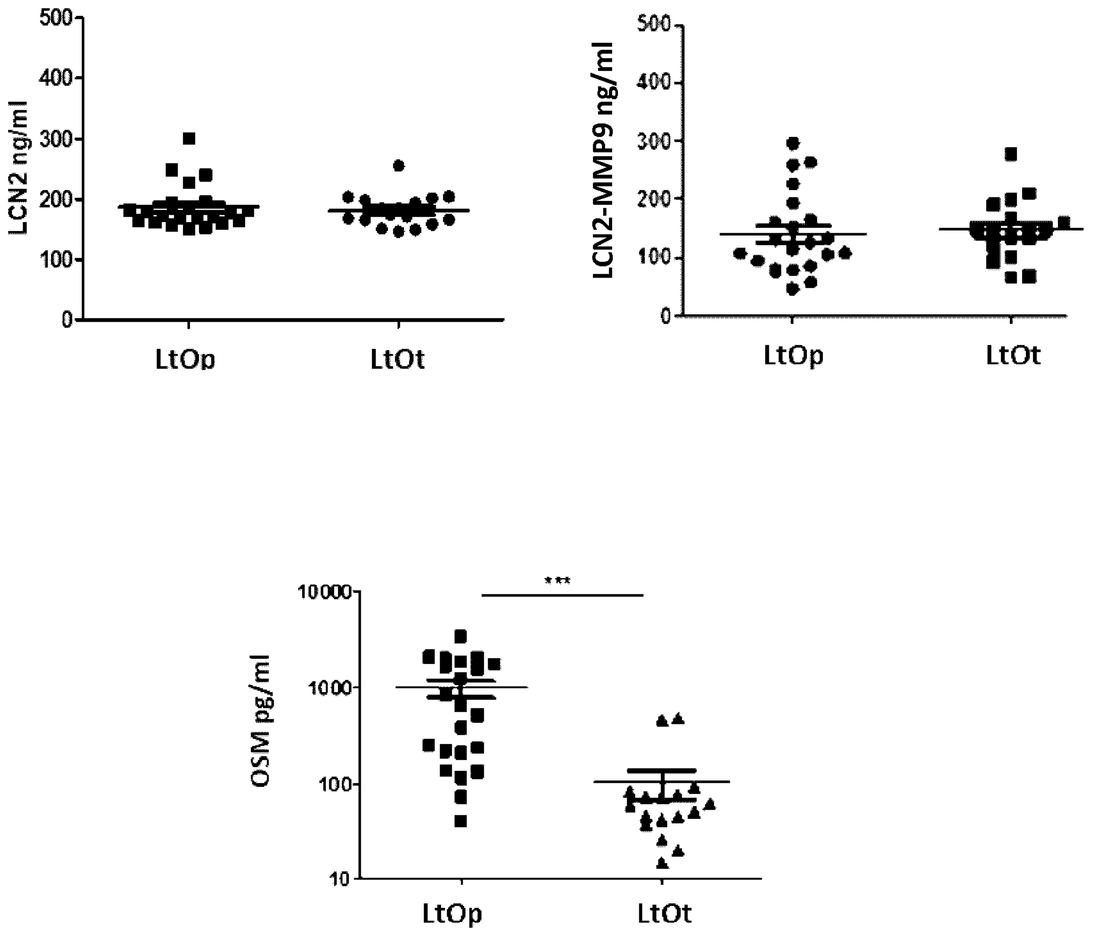

For patients with involvement of both LCN2 and OSM pathways, there are two distinct patient groups: Lp and Lt; each of which has 2 subgroups: Op and Ot. Comparison of patients LpOp (n=27) vs LpOt (n=8) reveals no significant difference in LCN2, LCN2-MMP9 and OSM levels (LCN2 levels in LpOp vs LpOt: 229 ng/ml±13 vs 227 ng/ml±18; LCN2-MMP9 levels in LpOp vs LpOt: 181 ng/ml±17 vs 129 ng/ml±10; OSM levels in LpOp vs LpOt: 575 pg/ml±125 vs 178 pg/ml±90; FIG. 2A). Comparison of patients LtOp (n=22) vs LtOt (n=17) shows no difference in LCN2 and LCN2-MMP9 levels (LCN2 levels in LtOp vs LtOt: 186 ng/ml±8 vs 181 ng/ml 7; LCN2-MMP9 levels in LtOp vs LtOt: 139 ng/ml±15 vs 148 ng/ml±13;); but there is significant difference in OSM levels (LtOp vs LtOt: 978 pg/ml±20 vs 103 pg/ml±34, p=0.0006; FIG. 2B). It appears that only when LCN2 is transiently elevated, persistently elevated OSM levels (Op) are much higher than transiently elevated OSM levels (Ot). The remaining results focus on analyses of patients who have involvement in a single pathway, either LCN2 or OSM. The different categories of patients with pathways involvements are summarized in Table 2.

TABLE 2

Summary of different categories of patients with the involvement of different pathways.

| Pathway(s) involved | | n |
|---|---|---|
| LCN2 (L) | LpOn | 82 |
| | LtOn | 41 |
| OSM (O) | LnOp | 24 |
| | LnOt | 3 |
| LCN2 + OSM | | |
| Group 1 | LpOp | 27 |
| | LpOt | 8 |
| Group 2 | LtOp | 22 |
| | LtOt | 17 |
| Normalized | LnOn | 62 |
| Total | | 286 |

Figure 3A:
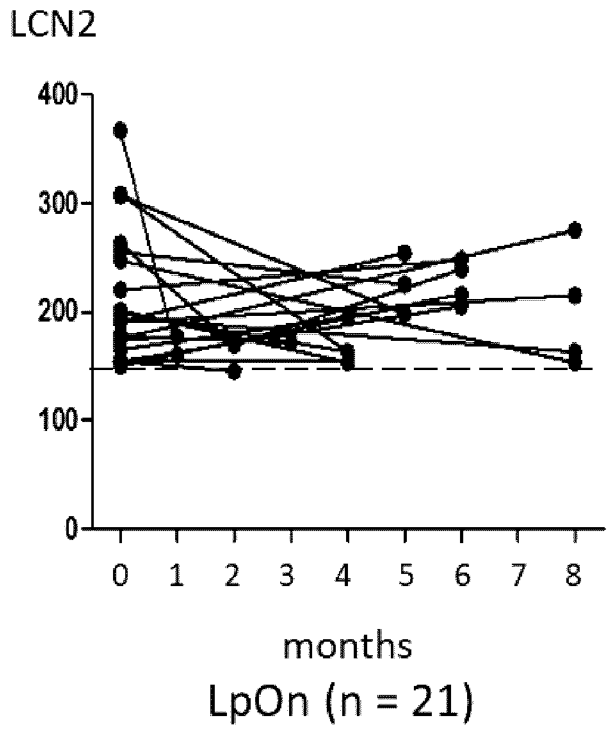
FIG. 3A shows sequential measurements of LCN2 levels within a year in patients with persistent LCN2 elevation but normal OSM (LpOn, n=21). Dashed line represents the cut-off level for LCN2 at 150 ng/ml.
Figure 3B:
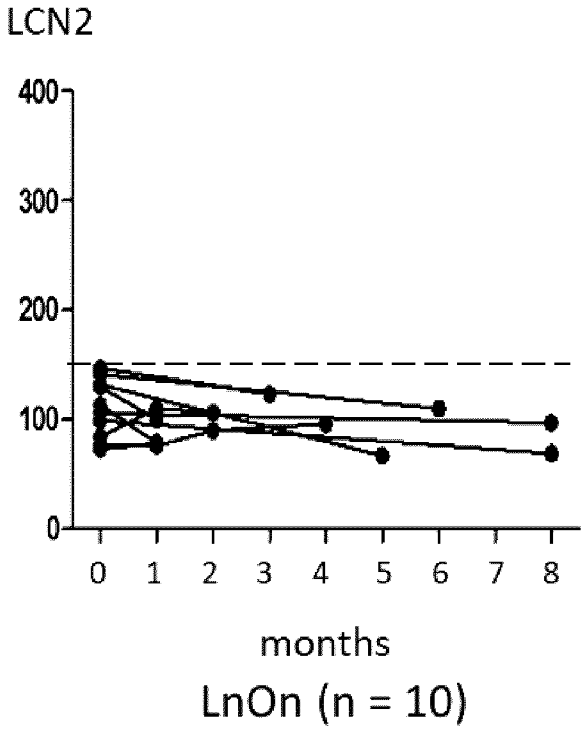
FIG. 3B shows sequential measurements of LCN2 levels within a year in patients with normal LCN2 and OSM (LnOn, n=10). Dashed line represents the cut-off level for LCN2 at 150 ng/ml.
Figure 3C:
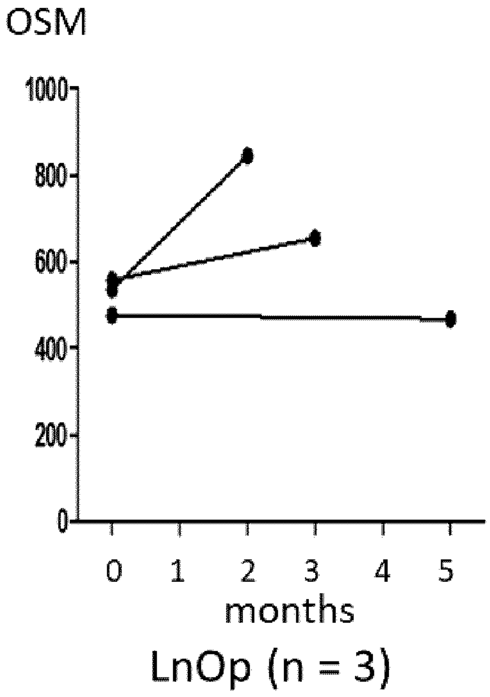
FIG. 3C shows sequential measurements of OSM levels within a year in patients with persistent OSM elevation but normal LCN2 (LnOp, n=3).

The above results were based on annual measurements of LCN2 or OSM to establish the pattern of elevation: transient or persistent. Whether the elevation patterns could be established in less than a year was assessed. About 10% (34/286) of the axSpA patients in the cohort had more frequent serial assessment mainly due to acute increased back pain. FIG. 3A, FIG. 3B, and FIG. 3C showed sequential measurements of LCN2 or OSM from these patients. The results indicated that the pattern of LCN2 or OSM elevation or normalization could be established with repeat measurements 3 months apart.

Figure 4A:
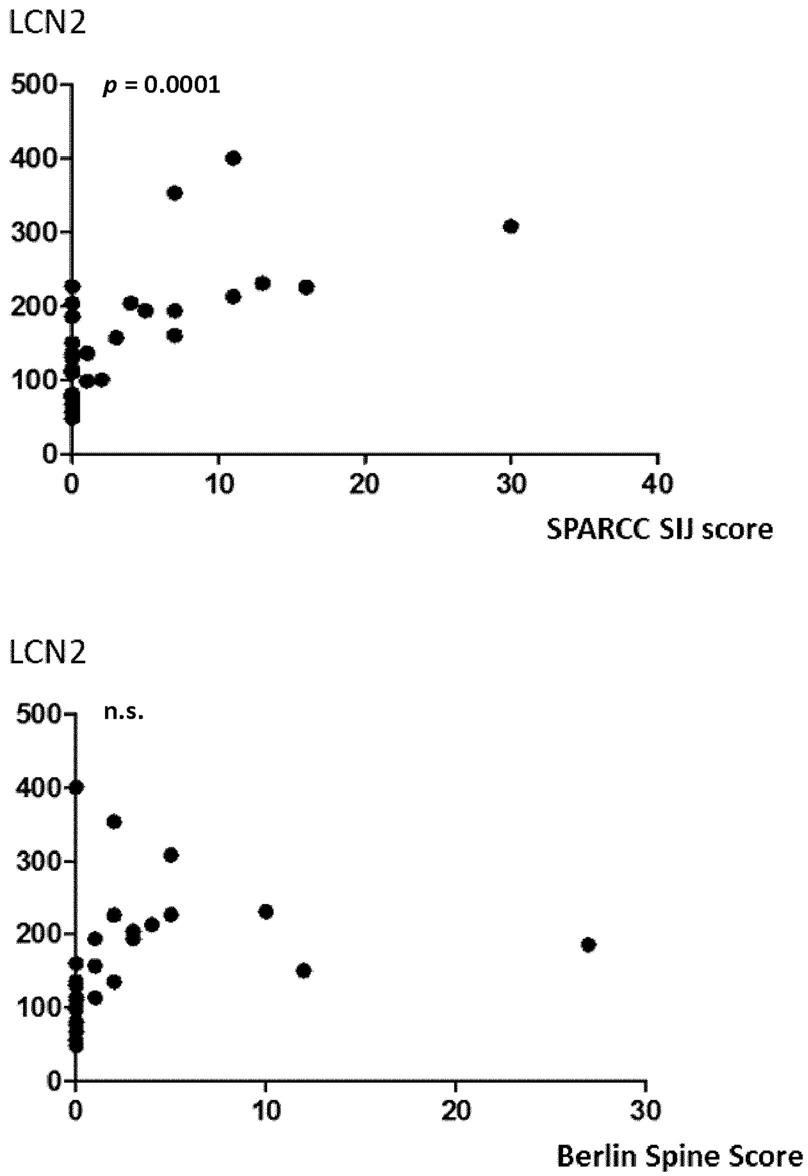
FIG. 4A shows the correlation of LCN2 levels with SPARCC SIJ scores and Berlin Spine scores in patients with the involvement of LCN2 pathway alone (LpOn, n=15) and with normal LCN2 and OSM (LnOn, n=13). Pearson's correlation coefficient test was used. n.s. stands for not significant.
Figure 4B:
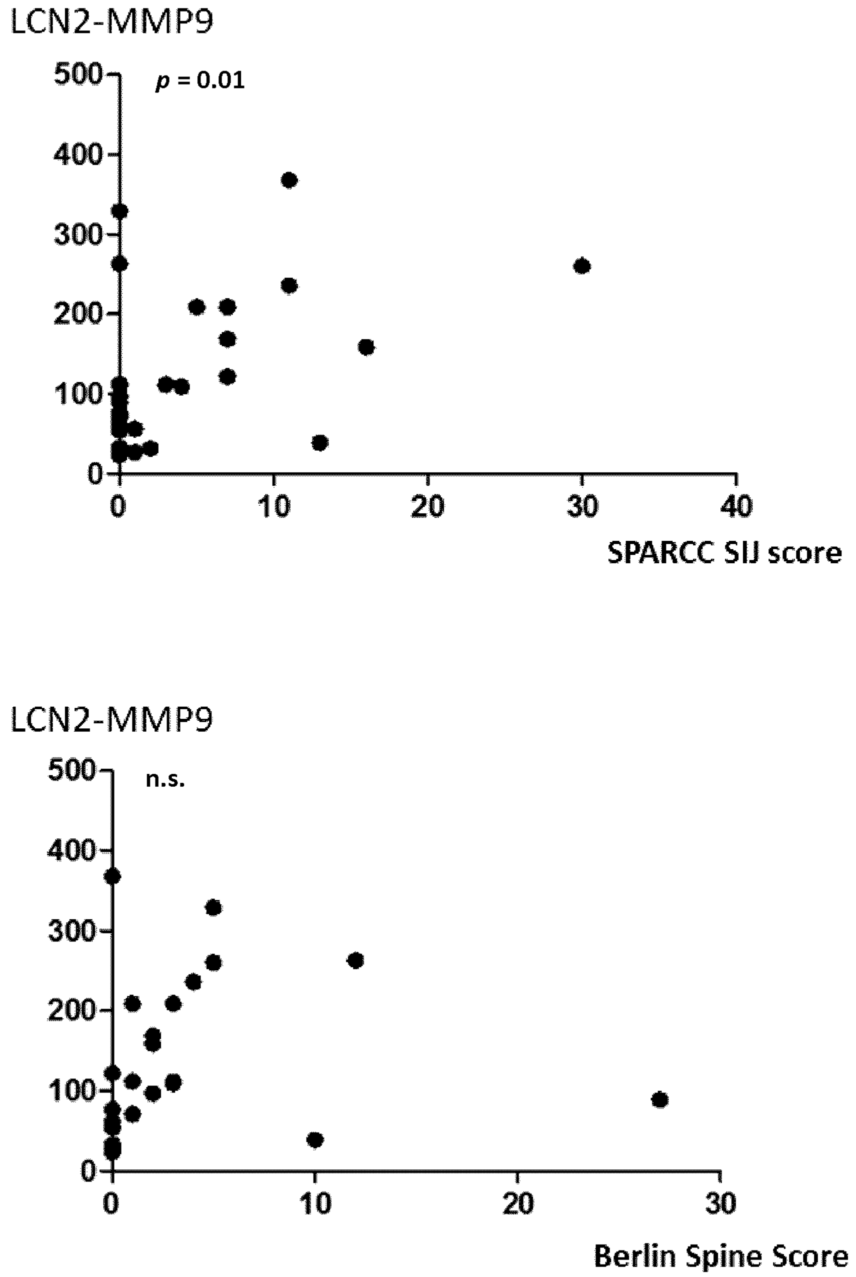
FIG. 4B shows the correlation of LCN2-MMP9 levels with SPARCC SIJ scores and Berlin Spine scores in patients with the involvement of LCN2 pathway alone (LpOn, n=15) and with normal LCN2 and OSM (LnOn, n=13). Pearson's correlation coefficient test was used. n.s. stands for not significant.
Figure 4C:
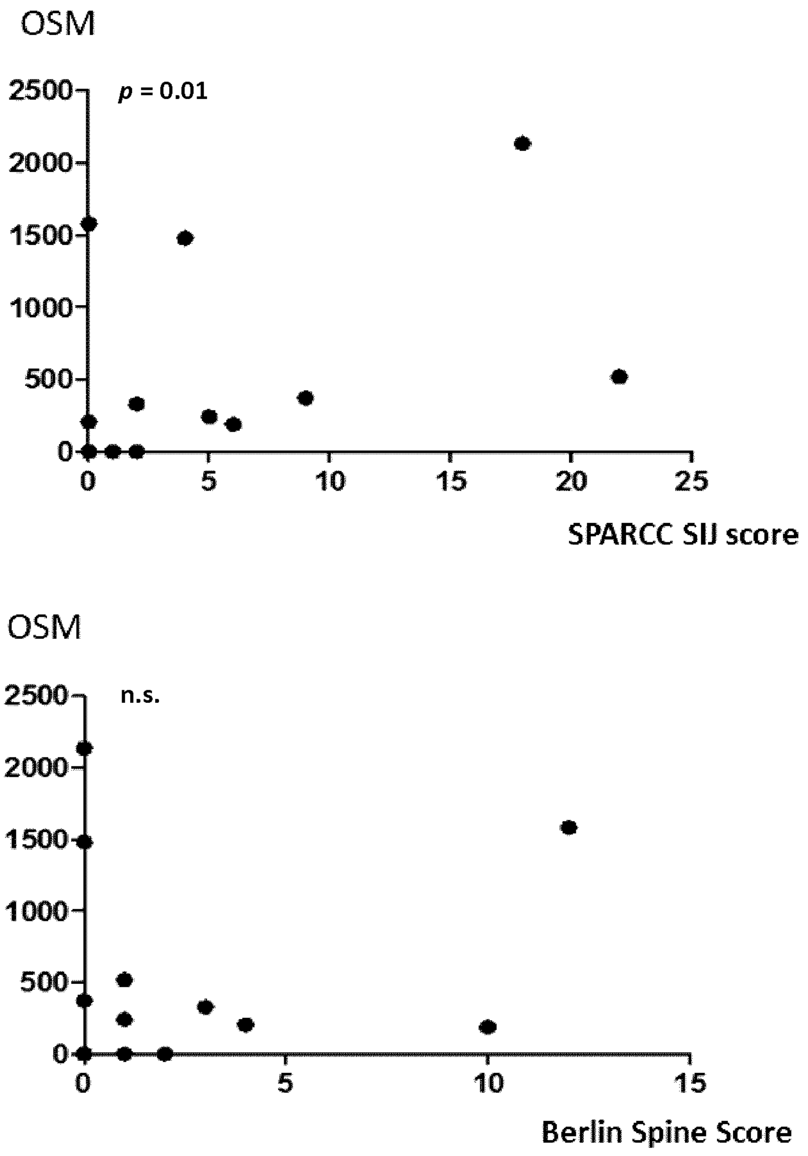
FIG. 4C shows the correlation of OSM levels with SPARCC SIJ scores and Berlin Spine scores in patients with the involvement of OSM pathway alone (LnOp, n=9) and with normal LCN2 and OSM (LnOn, n=13). Pearson's correlation coefficient test was used. n.s. stands for not significant.

Example 2: MRI Evidence of Sacroiliac Joint (SIJ) Involvement is Correlated with Elevated LCN2, and OSM in axSpA Patients MRI scores (SPARCC SIJ vs Berlin spine; Hededal P, et al. 2018) are available from patients with single pathway involvements: LpOn (15 axSpA), LnOp (9 axSpA); and patients with normal LCN2 and OSM levels: LnOn (13 axSpA). MRI taken within 12 months of the time of biomarker measurements were used for this analysis. Correlation are made between LCN2, LCN2-MMP9, or OSM levels, and the SPARCC SIJ and Berlin spine scores. In all axSpA patients, significant correlations are present between LCN2 levels and SPARCC SIJ scores (Pearson's correlation coefficient=0.66, p=0.0001), but not with Berlin spine scores (Pearson's correlation coefficient=0.22, p=0.27) in LpOn (n=15) and LnOn (n=13) patients (n=28; FIG. 4A). Similarly, levels of LCN2-MMP9 are correlated with SPARCC SIJ scores (Pearson's correlation coefficient=0.5, p=0.01), but not Berlin spine scores (Pearson's correlation coefficient=0.2, p=0.39) in LpOn (n=15) and LnOn (n=13) patients (n=28; FIG. 4B). For LnOp (n=9) and LnOn (n=13) patients, there is significant correlation between OSM levels and SPARCC SIJ scores only (n=22; Pearson's correlation coefficient=0.53, p=0.01; FIG. 4C). There is no correlation between OSM levels and Berlin Spine scores in these patients (n=22; Pearson's correlation coefficient=0.3, p=0.17; FIG. 4C). These results show that persistent elevation of LCN2, LCN2-MMP9, and/or OSM is associated with SIJ inflammation.

Example 3: Association of Treatment Outcome with Pathway Involvement

Since persistent elevation of LCN2 or OSM reflects SIJ inflammation, whether there is any association of LCN2 or OSM levels with the central clinical symptom back pain in the evaluation of treatment response of the patients was assessed. Using sequential LCN2 and OSM measurements and sequential back pain scores (question 2 of BASDAI survey; Garrett S 1994), concordant vs discordant association were observed in responses to all treatments (both with and without TNFi). Responder (R) and non-responder (NR) are patients with the concordant pattern. R had normalized LCN2, and/or OSM levels as well as reduced back pain scores (<4) after treatments. NR remained having persistently elevated LCN2 and/or OSM, and back pain scores (>4) after treatments. Patients with Pain Resolved (PR; LCN2/OSM elevated) and Pain Persisting (PP; LCN2/OSM normal) belong to the discordant group. The persistent back pain in this group of patients is likely not due to involvement of LCN2 and OSM pathways and could reflect a possibly non-inflammatory nature of their back pain in question.

How the pathway involving LCN2 or OSM might affect the outcome of treatments was assessed, both with and without TNFi. Treatment response was compared in patients having involvement of the LCN2 pathway alone. For patients with persistent LCN2 elevation (LpOn), profiling indicated that both concordant and discordant patterns were observed. Patients with concordant response were mostly NR (35% [29/82]). Only 12% [10/82] are R. Most of the patients with discordant response are PR (pain resolved but LCN2 remained elevated; 50% [41/82]). Only two patients with discordant response are PP (pain persisted but with normal LCN2; 2% [2/82]; Table 3A). Similarly, both concordant and discordant treatment responses are observed in patients with transient LCN2 elevation (LtOn). However, for patients with concordant treatment responses, significantly more of them are responders [R] (LpOn vs LtOn; R: 11% vs 71%; NR: 35% vs 7%; Pearson's $chi^2$=27.9, p<0.00001; Table 3B).

TABLE 3A

Comparison of treatments outcome in patients with normal OSM but persistent LCN2 elevation vs. transient LCN2 elevation vs. normal LCN2.

| | | All treatments (with and without TNFi) | | | |
|---|---|---|---|---|---|
| | LCN2 (L) | Concordant (LCN2 vs back pain) | | Discordant (LCN2 vs back pain) | |
| Pathway involved | mean ± SE (ng/ml) | R (%) | NR (%) | PR (%) | PP (%) |
| LpOn (n = 82) | 259 ± 9 | 10/82 (12) | 29/82 (35) | 41/82 (50) | 2/82 (2) |
| LtOn (n = 41) | 193 ± 7 | 29/41 (71) | 4/41 (10) | 1/41 (2) | 7/41 (17) |
| LnOn (n = 62) | 114 ± 3 | 36/62 (58) | | | 26/62 (42) |

TABLE 3B

Comparison of treatments outcome in patients with normal OSM but persistent LCN2 elevation vs. transient LCN2 elevation.

| Rx response | R | NR | chi² (p-value) |
|---|---|---|---|
| LpOn | 10 | 29 | |
| LtOn | 29 | 4 | |
| | | | 27.9 (<0.00001) |

Out of 62 LnOn patients, 58% (36/62) are deemed responders [R] as defined by normal LCN2, undetectable OSM and low back pain scores. The remaining 42% (26/62) showed discordant treatment response, having the PP pattern as both LCN2 and OSM were persistently normal, but back pain persisted (Table 3A).

To evaluate whether LCN2-MMP9 are informative in treatment response, patterns are redefined only for this specific analysis (Table 4A and Table 4B). R had normalized LCN2-MMP9 and/or OSM levels as well as reduced back pain scores (<4) after treatments. NR remained having persistently elevated LCN2-MMP9 and/or OSM, and back pain scores (>4) after treatments. Patients with Pain Resolved (PR; LCN2-MMP9/OSM elevated) and Pain Persisting (PP; LCN2-MMP9/OSM normal) belong to the discordant group. Treatment response was compared in patients having involvement of the LCN2-MMP9 alone. For patients with persistent LCN2-MMP9 elevation (LMpOn), profiling indicated that both concordant and discordant patterns were observed. Patients with concordant response were mostly NR (33% [15/46]). Only 13% [6/46] are R. Most of the patients with discordant response are PR (pain resolved but LCN2 remained elevated; 54% [25/46]). No patients with discordant response are PP (Table 4A). Similarly, both concordant and discordant treatment responses are observed in patients with transient LCN2-MMP9 elevation (LMtOn). However, for patients with concordant treatment responses, significantly more of them are responders [R] (LpOn vs LtOn; R: 13% vs 40%; NR: 33% vs 23%; Pearson's $chi^2$=7.1, p=0.008; Table 4B).

TABLE 4A

Comparison of all treatment outcomes in patients with normal OSM but persistent LCN2/MMP9 elevation vs. transient LCN2/MMP9 elevation.

| | | All treatments (with and without TNFi) | | | |
|---|---|---|---|---|---|
| | LCN2/ MMP9 (LM) | Concordant (LM vs back pain) | | Discordant (LM vs back pain) | |
| | mean ± SE (ng/ml) | R (%) | NR (%) | PR (%) | PP (%) |
| LMpOn (n = 46) | 228 ± 9 | 6/46 (13) | 15/46 (33) | 25/46 (54) | |
| LMt/nOn (n = 77) | 130 ± 8 | 31/77 (40) | 18/77 (23) | 18/77 (23) | 10/77 (13) |

TABLE 4B

Comparison of concordant treatments outcome in patients with normal OSM but persistent LCN2/MMP9 elevation vs. transient LCN2/MMP9 elevation.

| Rx response | R | NR | chi² (p-value) |
|---|---|---|---|
| LMpOn | 6 | 15 | |
| LMtOn | 31 | 18 | |
| | | | 7.1 (0.008) |

Profiling treatment responses in patients with involvement of OSM (O) pathway alone (LnOp and LnOt) revealed differences compared with those found in LpOn patients with involvement of LCN2 (L) alone. All LnOp patients with concordant treatment responses are NR (63% [15/24]; with persisting elevated OSM levels and back pain >4). Those with discordant treatment response are all PR (pain resolved but elevated OSM levels persisted; 38% [9/24]; Table 5). Unlike LnOp patients, all LnOt patients in the cohort (n=3) are R with both pain resolved and OSM levels normalized. Thus, among patients with involvement of only one pathway (either LCN2 or OSM alone; comprising 43% and 9% of the present cohort, respectively; Table 1), transient elevation of LCN2 or OSM during the disease course (LtOn or LnOt) appears to be an indicator of better response to all treatments (Tables 3B and 5). In addition, current treatments are less effective in LnOp patients. None of the 24 LnOp patients in the cohorts were R, although about half of them are PR with back pain resolved but OSM elevation persisted (Table 5).

TABLE 5

Comparison of treatments outcome in patients with normal LCN2 but persistent OSM elevation vs. transient OSM elevation.

| | | | All treatments (with and without TNFi) | | | |
|---|---|---|---|---|---|---|
| | LCN2 (L) | OSM (O) | Concordant (OSM vs back pain) | | Discordant (OSM vs back pain) | |
| Pathway involved | mean ± SE (ng/ml) | mean ± SE (pg/ml) | R (%) | NR (%) | PR (%) | PP (%) |
| LnOp (n = 24) | 97 ± 6 | 463 ± 110 | | 15/24 (63) | 9/24 (38) | |
| LnOt (n = 3) | 78 ± 11 | 61 ± 14 | 3/3 (100) | | | |

Treatment response was also analyzed based on patients receiving TNFi vs no TNFi. The results are summarized in Tables 6A, 6B, 6C, 7A and 7B. In general, treatment response profiles (with vs without TNFi) are similar. Table 6A presents treatment outcomes in patients treated with TNFi who had normal OSM levels but persistent LCN2 elevation (LpOn, n=59)) vs. transient LCN2 elevation (LtOn, n=31) vs. normal LCN2 (LnOn, n=42). For TNFi-treated patients with LCN2 involvement only, Lp patients with concordant treatment response, compared to Lt patients, significantly more of them are responders [R] (LpOn vs LtOn; R: 12% vs 74%; NR: 44% vs 6%; Pearson's $chi^2$=28.5, p<0.00001; Table 6B). Table 6C presents treatment outcomes in patients treated with no TNFi who had normal OSM levels but persistent LCN2 elevation (LpOn, n=23) vs. transient LCN2 elevation (LtOn, n=10) vs. normal LCN2 (LnOn, n=20). Though the trend is similar in patients not treated with TNFi to those treated with TNFi, there are no significant differences when not treated with TNFi. This implicates TNFi as being more effective in patients with LCN2 pathway involvement. Table 7A presents treatment outcomes in patients treated with TNFi who had normal LCN2 levels but persistent OSM elevation (LnOp, n=16) vs. transient OSM elevation (LnOt, n=2). Table 7B presents treatment outcomes in patients treated with no TNFi who had normal LCN2 levels but persistent OSM elevation (LnOp, n=8) vs. transient OSM elevation (LnOt, n=1).

TABLE 6A

Association of treatment outcome in patients with the involvement of LCN2 pathway alone treated with TNFi.

| | LCN2 (L) | Concordant (LCN2 vs back pain) | | Discordant (LCN2 vs back pain) | |
|---|---|---|---|---|---|
| Pathway involved | mean ± SE (ng/ml) | R (%) | NR (%) | PR (%) | PP (%) |
| LpOn (n = 59) | 253 ± 9 | 7/59 (12) | 26/59 (44) | 24/59 (41) | 2/59 (3) |
| LtOn (n = 31) | 196 ± 8 | 23/31 (74) | 2/31 (6) | 1/31 (3) | 5/31 (16) |
| LnOn (n = 42) | 112 ± 4 | 25/42 (60) | | | 17/42 (40) |

TABLE 6B

Comparison of concordant treatments outcome in patients with normal OSM but persistent LCN2 elevation vs. transient LCN2 elevation.

| TNFi | R | NF | $chi^2$ (p-value) |
|---|---|---|---|
| LpOn | 7 | 26 | |
| LtOn | 23 | 2 | |
| | | | 28.5 (<0.00001) |

TABLE 6C

Association of treatment outcome in patients with the involvement of LCN2 pathway alone treated with no TNFi.

| | LCN2 (L) | Concordant (LCN2 vs back pain) | | Discordant (LCN2 vs back pain) | |
|---|---|---|---|---|---|
| Pathway involved | mean ± SE (ng/ml) | R (%) | NR (%) | PR (%) | PP (%) |
| LpOn (n = 23) | 273 ± 24 | 3/23 (13) | 3/23 (13) | 17/23 (74) | |
| LtOn (n = 10) | 184 ± 13 | 6/10 (60) | 2/10 (20) | | 2/10 (20) |
| LnOn (n = 20) | 117 ± 5 | 11/20 (55) | | | 9/20 (45) |

TABLE 7A

The association of treatment outcome in patients with the involvement of OSM pathway alone treated with TNFi.

| | LCN2 (L) | OSM (O) | Concordant (OSM vs back pain) | | Discordant (OSM vs back pain) | |
|---|---|---|---|---|---|---|
| Pathway involved | mean ± SE (ng/ml) | mean ± SE (pg/ml) | R (%) | NR (%) | PR (%) | PP (%) |
| LnOp (n = 16) | 102 ± 7 | 397 ± 120 | | 12/16 (75) | 4/16 (25) | |
| LnOt (n = 2) | 78 | 55 | 2/2 (100) | | | |

TABLE 7B

The association of treatment outcome in patients with the involvement of OSM pathway alone treated without TNFi.

| | LCN2 (L) | OSM (O) | Concordant (OSM vs back pain) | | Discordant (OSM vs back pain) | |
|---|---|---|---|---|---|---|
| Pathway involved | mean ± SE (ng/ml) | mean ± SE (pg/ml) | R (%) | NR (%) | PR (%) | PP (%) |
| LnOp (n = 8) | 87 ± 9 | 595 ± 231 | | 3/8 (38) | 5/8 (63) | |
| LnOt (n = 1) | 79 | 74 | 1/1 (100) | | | |

Profiling of treatment responses in r-axSpA vs nr-axSpA patients showed similar patterns. Whether HLA B27 status, gender, and comorbidities affected the outcome of treatment response by biomarkers profiling was assessed. None of these cofactors affected the analyses.

Example 4: Association of Treatment Outcome with Patterns of CRP Elevation

CRP is a well-established contributor to systemic inflammation (Sproston NR 2018). Elevation of CRP is common in r-axSpA patients but less so in nr-axSpA patients. As stated in previous sections, persistently elevated LCN2 and OSM are observed in axSpA patients. To further evaluate whether persistent elevation of CRP could be found in r-axSpA patients in this cohort was examined. Nr-axSpA patients are excluded in this analysis as only 2 or these patients had elevated CRP in the cohort.

Figure 5A:
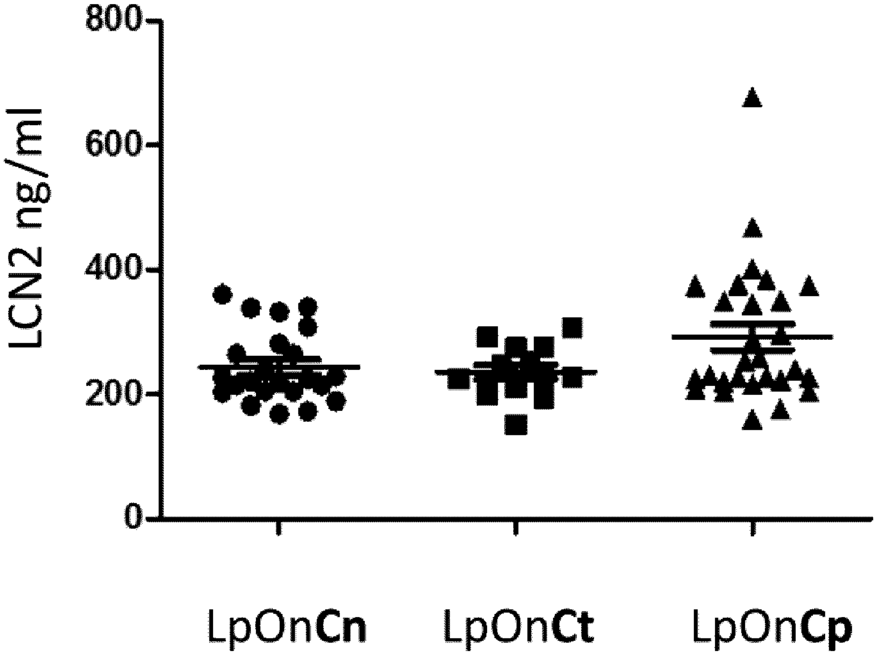
FIG. 5A shows a comparison of LCN2 levels in r-axSpA patients with normal CRP (LpOnCn, n=23) vs. transient CRP elevation (LpOnCt, n=14) vs. persistent CRP elevation (LpOnCp, n=28). One-way analysis of variance (ANOVA) followed by Bonferroni's multiple comparison test and Student't test were used.
Figure 5B:
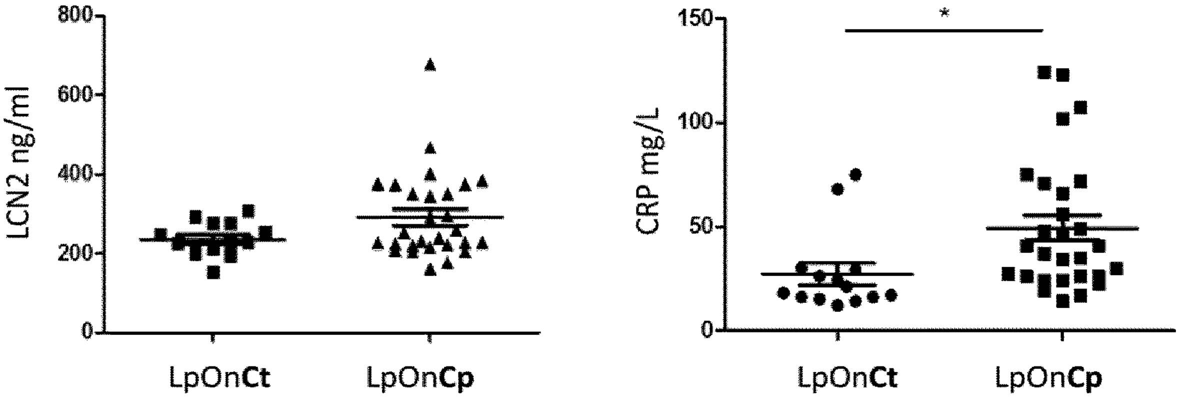
FIG. 5B shows a comparison of LCN2 (left) and CRP (right) levels in r-axSpA patients with transient CRP elevation (LpOnCt) vs. persistent CRP elevation (LpOnCp). Student's t test was used.

Similar to LCN2 and OSM, both transient and persistent elevations of serum CRP are found in r-axSpA patients as expected. Patients with any CRP elevation (Cp or Ct) are predominantly found in patients with LCN2 pathway involvement (LpOnCp and LpOnCt; 43% [28/65] and 22% [14/65] respectively of LpOn patients in the present cohort). LpOnCp patients had higher LCN2 levels (compared to levels from LpOnCt and LpOnCn patients; 293 ng/ml±21 [LpOnCp] vs 235 ng/ml±11 [LpOnCt] vs 243 ng/ml±12 [LpOnCn]; one-way ANOVA p=0.04; FIG. 5A). LpOnCp patients also had higher CRP levels, compared to levels from LpOnCt patients (49 mg/L±6 [LpOnCp] vs 27 mg/L±5 [LpOnCt]; Student's t test p=0.02; FIG. 5B).

Whether persistent vs transient CRP elevation might have differential effects on treatment response (with and without TNFi) in LpOn patients (LpOnCp vs LOnCt) was evaluated. LpOnCp patients have higher and lower % of non-responders [NR] and responders [R] respectively (NR: 36% vs 21%; R: 7% vs 29%; LpOnCp vs LpOnCt respectively; Table 8A); though p=0.06 for Pearson's $chi^2$ test (Table 8B). This is likely due to the low numbers for statistical analysis. Taken together, persistent CRP elevations (Cp) likely have a small effect, if any, on treatment response outcome in LpOn patients.

TABLE 8A

Comparison of treatment outcomes in patients with normal CRP vs. transient CRP elevation vs. persistent CRP elevation.

| All treatments (with and without TNFi) | | | | Concordant (LCN2 vs back pain) | | Discordant (LCN2 vs back pain) | |
|---|---|---|---|---|---|---|---|
| | | LCN2 (L) | CRP (C) | | | | |
| pathways(s) involved | AS (n) | mean ± SE (ng/ml) | mean ± SE (mg/L) | R (%) | NR (%) | PR (%) | PP (%) |
| LpOn Cn | 23 | 243 ± 12 | <11 (normal) | 3/23 (13) | 8/23 (35) | 11/23 (48) | 1/23 (4) |
| LpOn Ct | 14 | 235 ± 11 | 27 ± 5 | 4/14 (29) | 3/14 (21) | 7/14 (50) | |
| LpOn Cp | 28 | 293 ± 21 | 49 ± 6 | 2/28 (7) | 10/28 (36) | 16/28 (57) | |

TABLE 8B

Comparison of treatment outcomes in patients with transient CRP elevation vs. persistent CRP elevation.

| Rx response | R | NR | $chi^2$ (p-value) |
|---|---|---|---|
| LpOnCt | 4 | 3 | |
| LpOnCp | 2 | 10 | |
| | | | 3.4 (0.06) |

Thus, the biomarkers disclosed herein are more sensitive than CRP, as there more positive cases than CRP.

Example 5: Treatments Result in Clinical Improvement Reflected by Changes of LCN2 and/or LCN2-MMP9 in axSPA with OSM Normal Table 9 shows levels of LCN2 (L) and LCN2-MMP9 (LM) change in response to the switch/initiation of specific treatment(s) at a given time. The cutoffs for L and LM are 150 ng/ml and 100 ng/ml, respectively

TABLE 9

Levels of LCN2 (L) and LCN2-MMP2 (LM) in response to the switch or initiation of specific treatments.

| | Patient # | Bleed Date | L | LM | O | Rx |
|---|---|---|---|---|---|---|
| ASM− | 551 | 2010.8 | 207 | 125 | 0 | Ns8 |
| | | 2011.6 | 86 | 33 | 0 | Ns8Bg14 |
| | | 2011.9 | 85 | 25 | 0 | Ns8Bg14 |
| ASF− | 485 | 2009.4 | 224 | 154 | 0 | Bg16 |
| | | 2010.3 | 140 | 73 | 0 | Bg16 |
| | | 2011.3 | 89 | 42 | 0 | Bg16 |
| ASM− | 1233 | 2014.6 | 199 | 123 | 0 | Ns4 |
| | | 2014.10 | 163 | 83 | 0 | Ns4 |
| | | 2015.4 | 156 | 77 | 0 | Ns4Bg15 |
| | | 2015.9 | 105 | 33 | 0 | Ns4Bg15 |
| ASF+ | 622 | 2009.3 | 182 | 83 | 0 | Ns8Dm8 |
| | | 2010.2 | 141 | 67 | 0 | Dm8 |
| | | 2013.5 | 75 | 18 | 0 | Dm8 |
| ASF+ | 784 | 2012.8 | 197 | 69 | 0 | Ns2 |
| | | 2013.6 | 126 | 35 | 0 | Ns2 |
| | | 2015.2 | 117 | 57 | 0 | Ns2 |
| ASM+ | 609 | 2009.2 | 182 | 93 | 0 | Bg14Ns8 |
| | | 2010.1 | 204 | 112 | 0 | Bg14Ns8 |
| | | 2012.7 | 147 | 73 | 0 | Bg15Ns8 |
| | | 2014.7 | 89 | 16 | 0 | Bg15Ns8 |
| ASM− | 862 | 2011.2 | 129 | 121 | 0 | Ns3 |
| | | 2012.3 | 83 | 46 | 0 | Ns10 |
| | | 2013.3 | 93 | 61 | 0 | Ns10 |
| ASM+ | 60 | 2008.12 | 140 | 131 | 0 | Bg16 |
| | | 2010.12 | 90 | 91 | 0 | Bg16 |
| | | 2011.12 | 90 | 102 | 0 | Bg16 |
| | | 2013.3 | 64 | 53 | 0 | Bg16 |

For patient 551: L and LM levels were elevated (207 ng/ml and 125 ng/ml, respectively) in August 2010, under an NSAID treatment Ns8. With the initiation of a biologic treatment (Bg14) since June 2011, both L and LM were normalized and remained normal to the next assessment in September 2011. This indicates that Bg14 worked effectively in controlling inflammation in this patient.

For patient 485: This patient has been on a biologic treatment (Bg16) since April 2009. The L and LM levels were elevated in 2009. With Bg16 for almost a year, the L and LM levels were normalized in March 2010 and remained normal ever since. Bg16 works in this patient.

For patient 1233: This patient had elevated L and LM in June 2014. With an NSAID treatment (Ns4) for 4 months, levels of LM went back to normal while L remained elevated in October 2014. Since the initiation of a biologic treatment (Bg15) in April 2015, his L levels were normalized in September 2015. This indicates that Ns4 is insufficient in controlling inflammation, while Bg15 is effective in this patient.

For patient 622: This patient had elevated levels of L and normal LM in March 2009, when she was under an NSAID treatment (Ns8) in combination with a DMARD treatment (Dm8). After removal of Ns8, her L levels were normalized and LM remained normal, indicating that Ns8 might not be necessary for this patient.

For patient 784: This patient showed elevated L and normal LM in August 2012. After 10 month of NSAID treatment (Ns2), levels of L were normalized and both L and LM remained normal since then. This indicates that NSAID treatment is effective in controlling inflammation in this patient, the expensive biologic treatments might not be necessary.

For patient 609: This patient had elevated L and normal LM in February 2009, and elevated L and LM in January 2010. During this time period, he has been under Bg14 in combination with Ns8. In July 2012 after switching biologic treatments from Bg14 to Bg15, both L and LM were normalized and remained normal. This shows that Bg15 but not Bg14 is effective for this patient.

For patient 862: This patient had elevated LM and normal L in February 2011 under an NSAID (Ns3) treatment. Since the change of NSAID from Ns3 to Ns10 in March 2012, his L and LM levels were normal. This indicates that different NSAID treatments may have differential effect in normalizing LM.

For patient 60: This patient had normal L throughout the assessment period. However, despite the unchanged Bg16 treatment, the levels of LM fluctuated during the 4 time points from December 2008 to March 2013.

Example 6: Association of LCN2, LCN2-MMP9, and OSM in the Ankylosis Aspect of axSpA In order to assess whether LCN2, LCN2-MMP9, and OSM could predict disease progression, Modified Stoke Ankylosing Spondylitis Spinal Score (mSASSS), which reflects the degree of neo-ossification in the spine of patients with r-axSpA, was compared. Higher mSASSS indicates a more advanced stage of the r-axSpA disease. Levels of LCN2-MMP9 are significantly correlated with mSASSS (n=197; Pearson's correlation coefficient=0.15, p=0.04; FIG. 6). When patients are further categorized by the pattern of elevation of LCN2 and OSM, there is a positive correlation of the levels of LCN2-MMP9 with mSASSS in patients with persistent elevation of LCN2 and OSM (LpOp; n=20; Pearson's correlation coefficient=0.5, p=0.01; FIG. 7). However, such association is not discovered in the levels of LCN2 (n=20; Pearson's correlation coefficient=0.2, p=0.4) or CRP (n=20; Pearson's correlation coefficient=0.1, p=0.6).

Regardless of OSM status, there is a higher percentage of LpLMp patients with high mSASSS (mSASSS>10) compared to those with LpLMt (LpLMp vs LpLMt; mSASSS>10: 83% vs 45%; $chi^2$=8.1, p=0.004; Table 10).

TABLE 10

Association between the degree of ankylosis (mSASSS) and LCN2-MMP9 status in axSpA patients with persistent elevation of LCN2.

| | | | | Back pain duration (years) | |
|---|---|---|---|---|---|
| | mSASSS > 10 (%) | mSASSS < 10 (%) | $Chi^2$ (p value) | mSASSS > 10 | mSASSS < 10 |
| LpLMp (n = 30) | 25/30 (83) | 5/30 (17) | | 5-42 | 12-30 |
| LpLMt (n = 20) | 9/20 (45) | 11/20 (55) | | 5-41 | 17-54 |
| LpLMp vs LpLMt | 25/30 vs 9/20 | 5/30 vs 11/20 | 8.1 (0.004**) | | |

In those with OSM pathway involvement, high proportion of patients with mSASSS>10 is observed (75%; Table 11) in LnLMnOp patients, indicating higher risk of disease progression for patients with persistent elevation. The proportion of patients with more severe spinal ankylosis (mSASSS>10) is further increased in those with persistently elevated LCM2, LCN2-MMP9 and OSM (LpLMpOp; Table 11).

TABLE 11

The association between the degree of ankylosis (mSASS scores) and persistently elevated OSM in axSpA patients with persistent elevation or normal levels of LCN2 and LCN2-MMP9.

| | | | Back pain duration (years) | |
|---|---|---|---|---|
| | mSASSS > 10 (%) | mSASSS < 10 (%) | mSASSS > 10 | mSASSS < 10 |
| LnLMnOp (n = 8) | 6/8 (75) | 2/8 (25) | 1-31 | 12-23 |
| LpLMpOp (n = 7) | 7/7 (100) | 0/7 (0) | 5-38 | |

Herein provided is an example of a method for prognosticating r-axSpA patients. Both LCN2 and OSM pathways are involved in spinal ankyloses development in r-axSpA patients. For LCN2 pathway, persistent elevation of both LCN2 and LCN2-MMP9 is indicative of the likelihood of the subject to have progression in ankylosis. Persistent elevation of all 3 biomarkers (LCN2, LCN2-MMP9 and OSM; signature LpLMpOp) is a predictor of disease severity, having synergistic effect on spinal ankylosis.

As LCN2, LCN2-MMP9, and OSM are associated with local joint inflammation and ankylosis in axSpA, normalization of all three biomarkers controls inflammation and disease progression (FIG. 8).

Methods

Patient Selection:

286 axSpA patients (200 r-axSpA and 86 nr-axSpA) followed yearly (as per protocol) in the Toronto Western Hospital Spondylitis Clinics for up to 12 years, were used in this retrospective longitudinal association study. Sequential serum samples were obtained at each visit. Demographic features of this cohort are summarized in Table 12. Clinical parameters available include age, gender, B27 status, duration of back pain, comorbidities, BASDAI, ESR and CRP. The study was approved by UHN ethics committee, and all participating patients provided written informed consent.

TABLE 12

Demographics of axSpA patients in different categories.

| Pathway(s) involved | | n | B27 + ve (%) | TNFi treated (%) | no comorbidities (%) |
|---|---|---|---|---|---|
| LCN2 (L) | LpOn | 82 | 58/82 (71) | 59/82 (72) | 33/82 (40) |
| | LtOn | 41 | 32/41 (78) | 31/41 (76) | 17/41 (41) |
| OSM (O) | LnOp | 24 | 22/24 (92) | 17/24 (71) | 13/24 (54) |
| | LnOt | 3 | 1/3 (33) | 2/3 (67) | 3/3 (100) |
| LCN2 + OSM | | | | | |
| Group 1 | LpOp | 27 | 21/27 (78) | 21/27 (78) | 12/27 (44) |
| | LpOt | 8 | 8/8 (100) | 7/8 (88) | 5/8 (63) |
| Group 2 | LtOp | 22 | 17/22 (77) | 17/22 (77) | 10/22 (45) |
| | LtOt | 17 | 11/17 (65) | 12/17 (71) | 6/17 (35) |
| Normalized | LnOn | 62 | 47/62 (76) | 44/62 (71) | 28/62 (45) |
| Total | | 286 | 217/286 (76) | 210/286 (73) | 127/286 (44) |

Samples from 99 healthy male controls and 98 healthy female controls were used. Serum analytes were measured once in each control group.

Blood Sample:

Blood samples were collected and allowed to clot at 4° C. Samples were then centrifuged for 10 min at 3000 g. Serum samples were aliquoted and stored at −70° C. until use.

Back Pain Scoring:

The second question of the BASDAI questionnaire was used as the back pain score. It is a subjective self-assessment of neck, back and hip pain.

MRI Scoring:

Information on MRI assessment is available from 37 axSpA patients in this cohort. For evaluation of SIJ and spinal joint imaging, Spondyloarthritis Research Consortium of Canada (SPARCC) scoring and Berlin spinal joint scoring (Maksymowych WP 2005a; 2005b) were used. Scoring were done independently by two central readers. Discordant cases were settled through consensus. The mean scores from the two readers were used for statistical analysis.

Determination of Serum LCN2, LCN2-MMP9 and OSM Levels:

Aliquots of serum samples were stored at −70° C. until use. The sequential samples from each patient were thawed and analyzed at the same time to minimize assessment variabilities. Both LCN2 and OSM levels were measured by ELISA according to manufacturer's protocol and is known to the person skilled in the art. The ELISA kits used in this example for measuring L and LM are from R&D Systems:

Cat #: DLCN20: Quantikine ELISA for human Lipocalin-2/NGAL. Recombinant LM cross-reacts ~0.3% in this assay.

Cat #: DM9L20: Quantikine ELISA for human MMP9/NGAL complex. No significant cross-reactivity or interference with recombinant human LCN2. Recombinant human MMP9/TIMP1 complex interferes at concentrations >25 ng/ml.

The ELISA kit for measuring OSM is from Thermo Scientific (Cat #EHOSM: Human Oncostatin M (OSM) ELISA kit).

Statistical Analysis:

One-way analysis of variance (ANOVA), Pearson's correlation coefficient, student's t-test were carried using GraphPad Prism program. Chi-square ($Chi^2$) tests were calculated using an online calculator (socsistatistics.com). A two-tailed p-value of less than 0.05 is considered statistically significant.

Example 7. LCN2 and OSM Monitoring Outperforms CRP

Two pathways involving LCN2, LCN2-MMP9 and OSM, acting singly or in combinations, are identified in axSpA pathogenesis. The use of data from patients with single pathway involvement facilitates association of individual biomarkers with specific clinical outcome such as MRI and treatment outcome (back pain score).

A combinational monitoring of LCN2, LCN2-MMP9 and OSM levels, and concurrent back pain scores during the disease course can effectively predict treatment responses in axSpA patients, notwithstanding that back pain is a confounding variable, showing the importance of LCN2, LCN2-MMP9, and/or OSM levels in treatment response prediction. In r-axSpA, a subjective assessment of back pain as defined by the patient using functional index questionnaires is still used as the key clinical decision making by rheumatologists. A few percent of long standing r-axSpA patients have fused spine but no back pain. These patients can have high bios with ongoing inflammation indicating that these patients may have defects in pain perception. This points to the need for a gold standard for disease inflammatory activity as described in this disclosure. The deficiency of subjective assessment to inform on treatment response reiterates the importance of LCN2, LCN2-MMP9, and/or OSM levels in treatment response prediction. The strategy is informative when used in patients with single pathway involvement (LCN2 or OSM). AxSpA patients with discordant treatment responses (PR) having back pain resolved but LCN2 or OSM remaining elevated. For axSpA, the central clinical symptom is back pain. By tracking LCN2, LCN2-MMP9, and OSM levels which are associated with MRI evidence of SIJ inflammation, with back pain scores, different patterns of treatment responses were shown: concordant vs discordant. Detection of the discordant treatment response of PP (persisting pain with normal LCN2 and OSM levels) implicates a non-inflammatory nature of the patients' pain, and this would guide physicians to look for other causes of the back pain.

LCN2 levels in r-axSpA have recently been reported in a large r-axSpA cohort (462 r-axSpA patients; Lin A 2020) and a smaller sample which reported normal levels (21 r-axSpA patients; Turina MC 2017). Elevated baseline OSM levels have been reported in axSpA patients (18 r-axSpA and 9 nr-axSpA; Korkosz M 2018).

Two patterns of LCN2, LCN2-MMP9, and OSM elevation (persistent vs transient) were observed. Persistent elevation of LCN2 alone (LpOn; 43%:123/286) is more prevalent than persistent elevation of OSM alone (LnOp; 9%: 27/286). In these two groups of patients, MRI SPARCC SIJ scores were significantly correlated with both elevated LCN2, LCN2-MMP9 and OSM levels. This shows that persistent elevation of either LCN2 and/or LCN2-MMP9 and/or OSM reflects inflammation in the SIJ. There is no correlation between CRP levels and MRI SPARCC SIJ scores (Pearson's correlation coefficient=0.1, p=0.5) or MRI Berlin Spine Scores (Pearson's correlation coefficient=0.3, p=0.1; FIG. 9). In this regard, LCN2 LCN2-MMP9, and OSM outperform CRP. Among the MRI-negative patients in the present cohort, there are 12 axSpA patients who had persistent back pain despite normal LCN2, OSM, and CRP levels. The source of back pain in these patients is suggested to be non-inflammatory in origin.

Patients with persistent vs transient elevation of either LCN2 or OSM were assessed for differential treatment outcome. In both groups of patients with involvement of a single pathway, significantly more treatment responders [R] with pain and normalized LCN2 and OSM, were found in patients with transient elevation of LCN2 (LpOn vs LtOn; Table 3b) and no such responders were found in patients with persistent elevation of OSM (LnOp vs LnOt; Table 5). Half of all patients with persistent elevation of OSM, irrespective of the status of LCN2 involvement (LnOp, LtOp, LpOp) were deemed non-responders [NR, both pain and LCN2/OSM persisted], and the rest had back pain resolved [PR; 51% (37/73); but LCN2/OSM persisted] with and without TNFi treatment.

A schematic is shown in FIG. 8. It also reflects the inability of TNFi alone to obliterate LCN2-mediated inflammatory effects. While TNFi block TNFα, other cytokines may persist to maintain the inflammatory process. IL17 synergizes with IL22 and TNFα to induce LCN2 expression in the colonic epithelium (Stallhofer J 2015) as well as in bone cells (Sims NA 2014). To date, TNFi and IL17i agents seem comparable in efficacy in axSpA (van der Heijde 2018).

There is a need for better therapeutic agents especially for blocking inflammation resulting from persistent OSM elevation. IBD patients have elevated OSM which may drive intestinal inflammation (Stallhofer J 2015). Elevated mucosal OSM levels have been reported as the primary cause of non-responsiveness to TNFi in IBD patients (West NR 2017). LCN2, LCN2-MMP9, and/or OSM In the cohort of axSpA patients, the correlation of SIJ MRI scores (but not spine MRI scores) with persistently elevated LCN2, LCN2-MMP9 and OSM levels implicates local SIJ inflammation due to these three factors.

It is demonstrated that persistently elevated LCN2, LCN2-MMP9, and/or OSM impacted the treatment response outcome (back pain) in axSpA patients, but persistently elevated CRP appeared to have less, if any, contribution to treatment response outcome. Previous report in the literature showed poor correlation of CRP with clinical response of biologic treatments (De Vries MK 2009). Thus, together with the present MRI results, it appears that LCN2, LCN2-MMP9 and OSM (but not CRP) are the main contributors of axSpA development, in the promotion of SIJ inflammation. Poor correlation of CRP levels with MRI inflammation has been reported (Magrey M 2019). CRP has been shown to be a predictor of r-axSpA radiographic progression especially in men (Ismail S 2019).

In the cohort, patients with longer duration follow-up (6-12 years) revealed two categories of Responders [R]. One subgroup had no serological markers of inflammation (normalized LCN2, OSM and CRP) and no back pain. Another subgroup had "flares" (fluctuating pattern of biomarkers). Most r-axSpA patients have a course of exacerbations and remissions in clinical disease activity. This subgroup differs from the Pain Resolved (PR) category in which both inflammation and pain were resolved for several years. Transient pain and inflammation resumed, but both resolved again in response to treatments, usually with change in medications. A different approach to assess treatment outcome was used. Instead of addressing all contributors to axSpA disease activity, early events due to LCN2- and OSM- related inflammation and back pain for the symptomatic read-out were focused on. Using this strategy, HLA B27 positivity, gender and comorbidities involvement did not affect the analyses on treatment response. The interpretation is that axSpA patients have common early pathogenic events. Heterogeneity of disease may be introduced later as influenced by cofactors such as HLA B27 status, gender and comorbidities.

LCN2, LCN2-MMP9 and OSM monitoring outperforms CRP and provides an objective assessment of these patients with respect to chronic local inflammation.

Example 8. LCN2 and LCN2-MMP9 in Inflammatory Bowel Disease

Materials and Methods:

Serum was obtained at a single time point from 63 adult males with chronic inflammatory bowel disease (IBD) on various anti-inflammatory therapies. None of the patients had clinical spondyloarthritis.

LCN2, LCN2-MMP9 and OSM assays were performed by same ELISA methods as for axSpA.

Results and Discussion

FIG. 9 shows the level of LCN2, LCN2-MMP9 and OSM in serum obtained from adult males with chronic IBD on various anti-inflammatory therapies. LCN2 and LCN2-MMP9 analytes trended directionally in the same way in all patients. Elevated LCN2 and/or LCN2-MMP9 were seen in some IBD patients both with ulcerative colitis and Crohn's disease. However, the ratios of LCN2-MMP9:LCN2 varied from patient to patient. In some patients [LCN2-MMP9]>>[LCN2]. 26 (41%) patients were OSM+. 9 patients (14%) showed OSM >500 pg/ml.

As LCN2 expression is associated with active inflammation and LCN2-MMP9 is associated with connective tissue repair and remodeling and can be associated with excessive repair (fibrosis) in the presence of inflammation, this supports that patients with elevated LCN2, normal LCN2-MMP9 have active inflammation, that patients with elevated LCN2-MMP9 and normal LCN2 likely have predominant fibrosis activity (progression), and that patients with normal levels of all analytes including OSM have quiescent controlled disease. Patients with elevated OSM have active inflammation.

Example 9: The Application of LCN2, LCN2-MMP9 and OSM in (1) Predicting the Development of IBD in axSpA; (2) Predicting the Development of axSpA in IBD Patients IBD is a common comorbidity of axSpA. Conversely, axSpA is a common comorbidity of IBD. Herein provided is an assessment on whether elevated levels of LCN2, LCN2-MMP9 and/or OSM can (1) differentiate male patients with IBD only vs those with axSpA-IBD and (2) differentiate male patients with axSpA only vs those with axSpA-IBD.

As these results are from IBD male patients, the analysis is focused on male patients in different groups. Nonetheless, the skilled person recognizes that the insight gained from these findings may be applied to a subject irrespective of gender. The male patients evaluated herein are categorized into three groups based on LCN2 vs LCN2-MMP9 levels: (1) Regardless of OSM status (Tables 13A, 13B), patients are categorized by LCN2 elevation alone (L+), with LCN2-MMP9 elevation alone (LM+), or with concurrent LCN2 and LCN2-MMP9 elevation (L+LM+); (2) When OSM is not detected (Tables 14A, 14C, 14D): patients are categorized by LCN2 elevation alone (L+O−), with LCN2-MMP9 elevation alone (LM+O−), or with concurrent LCN2 and LCN2-MMP9 elevation (L+LM+O−); (2) When OSM is positive (Tables 14B, 14E), patients are categorized by LCN2 elevation alone (L+O+), with LCN2-MMP9 elevation alone (LM+O+), or with concurrent LCN2 and LCN2-MMP9 elevation (L+LM+O+), or with normal LCN2 and LCN2-MMP9 (LnLMnO+). There is significant difference in the pattern of these biomarker combinations in OSM positive patients in axSpA-only compared to axSpA-IBD.

TABLE 13A

Comparison between male patients with IBD and axSpA-IBD.

| Male | L+ (%) | LM+ (%) | L+LM+ (%) | $chi^2$ (p-value) |
|---|---|---|---|---|
| IBD (n = 41) | 4 (10) | 24 (59) | 13 (32) | |
| axSpA-IBD (n = 25) | 5 (20) | 3 (12) | 17 (68) | |
| | | | | 13.9 (0.001) |

L+: LCN2 >150 ng/ml; LM+: LCN2-MMP9 >100 ng/ml)

TABLE 13B

Comparison between male patients with IBD and axSpA only.

| Male | L+ (%) | LM+ (%) | L+LM+ (%) | $chi^2$ (p-value) |
|---|---|---|---|---|
| IBD (n = 41) | 4 (10) | 24 (59) | 13 (32) | |
| axSpA only (n = 82) | 14 (17) | 7 (9) | 61 (74) | |
| | | | | 36.4 (<0.00001) |

L+: LCN2 >150 ng/ml; LM+: LCN2-MMP9 >100 ng/ml)

TABLE 14A

Comparison of male patients with axSpA only vs IBD vs axSpA-IBD when OSM is undetected.

| Male | L+O− (%) | LM+O− (%) | L+LM+O− (%) | $chi^2$ (p-value) |
|---|---|---|---|---|
| axSpA only | 7 (12) | 3 (5) | 48 (83) | |
| IBD | 2 (9) | 13 (59) | 7 (32) | |
| axSpA-IBD | 3 (20) | 2 (13) | 10 (67) | |
| | | | | 31.7 (<0.00001) |

TABLE 14B

Comparison of male patients with axSpA only vs IBD vs axSpA-IBD when OSM is detected.

| Male | L+O+ (%) | LM+O+ (%) | L+LM+O+ (%) | LnLMnO+ (%) | $chi^2$ (p-value) |
|---|---|---|---|---|---|
| axSpA only | 7 (18) | 4 (10) | 13 (33) | 16 (40) | |
| IBD | 2 (8) | 11 (42) | 6 (23) | 7 (27) | |
| axSpA-IBD | 2 (16) | 1 (8) | 7 (53) | 3 (23) | |
| | | | | | 14.2 (0.027*) |

TABLE 14C

Comparison of male patients with IBD vs axSpA-IBD when OSM is undetected.

| Male | L+O− (%) | LM+O− (%) | L+LM+O− (%) | $chi^2$ (p-value) |
|---|---|---|---|---|
| IBD | 2 (9) | 13 (59) | 7 (32) | |
| axSpA-IBD | 3 (20) | 2 (13) | 10 (67) | |
| | | | | 7.7 (0.02*) |

TABLE 14D

| Comparison of male patients with axSpA only vs axSpA-IBD when OSM is undetected. | | | | |
|---|---|---|---|---|
| Male | L+O− | LM+O− | L+LM+O− | $chi^2$ (p-value) |
| axSpA only | 7 | 3 | 48 | |
| axSpA-IBD | 3 | 2 | 10 | |
| | | | | 2.1 (0.35) |

TABLE 14E

| Comparison of male patients with axSpA only vs axSpA-IBD when OSM is detected. | | | | | |
|---|---|---|---|---|---|
| Male | L+O+ (%) | LM+O+ (%) | L+LM+O+ (%) | LnLMnO+ (%) | $chi^2$ (p-value) |
| axSpA only | 7 (18) | 4 (10) | 14(35) | 16(40) | |
| axSpA-IBD | 2 (16) | 1 (8) | 9(64) | 3(23) | |
| | | | | | 3.64 (0.05) |

(1) Predicting the Development of IBD in axSpA axSpA male patients with the pattern LM+ (when L is normal)) have increased risk of developing IBD. Regardless of OSM status, when patients are categorized based on levels of LCN2 and LCN2-MMP9 (L+ vs LM+ vs L+LM+), there are significantly more LM+ IBD patients (59% [24/41]; Table 13) compared to axSpA-IBD (12% [3/25]; $chi^2$=13.9, p=0.001; Table 13A); and compared to axSpA only patients (with no comorbidities (9% [7/82]; $chi^2$=36.4, p<0.00001; Table 13B). This is further confirmed when the OSM status is considered: Based on results when patients have undetectable OSM (L+O− vs LM+O− vs L+LM+O−), there are significantly more LM+ IBD patients (59% [13/22]; Table 14A) compared to axSpA-IBD patients (13% [2/15]; Table 14A); and compared to axSpA only patients (with no comorbidities (3% [5/58]; $chi^2$=31.7, p<0.00001; Table 14A). Similar findings are observed in IBD vs axSpA-IBD vs axSpA only patients with detectable OSM levels (L+O+ vs LM+O+ vs L+LM+O+; $chi^2$=14.2, p=0.027; Table 14B).

Moreover, axSpA male patients with the pattern L+LM+O+ are more susceptible to have concurrent IBD. There are significantly more axSpA-IBD patients (64% [9/14]; Table 14E) than axSpA only patients with the pattern L+LM+O+ (35% [14/40]; chi=3.64, p=0.05; Table 14E). However, the pattern L+LM+O+ failed to distinguish IBD only patients from axSpA-IBD patients.

(2) Predicting the Development of axSpA in IBD Patients

IBD male patients with the pattern L+O− and/or L+LM+O− are more susceptible to have articular development. Based on results when patients have undetected OSM (L+O− vs LM+O− vs L+LM+O−), there are significantly more L+O− and L+LM+O− axSpA-IBD patients (20% [3/15] with L+O− and 67% [10/15] with L+LM+O−; Table 14C) compared to IBD patients (9% [2/22] with L+O− and 32% [7/22]; $chi^2$=7.7, p=0.02; Table 14C). This indicates the roles of patterns L+O− and/or L+LM+O− in indicating articular development in IBD patients. However, based on this type of analysis, axSpA only patients cannot be distinguished from axSpA-IBD patients, likely due to the existence of subclinical IBD in axSpA only patients (Table 14D).

Example 10. Elevated LCN2-MMP9 with Normal LCN2

Introduction

Herein provided is an assessment on whether in spondyloarthritis, at the same time point, LCN2-MMP9 can be elevated when LCN2 is within the normal range.

Results and Discussion

Table 15 shows LCN2 and LCN2-MMP9 level from male r-axSpA patients without inflammatory bowel disease (IBD). Using upper limits of normal specified in Table 15 (i.e. LCN2 monomer and/or homodimer: 150 ng/ml; LCN2-MMP9 heterodimer: 100 ng/ml), it is determined that in spondyloarthritis, at the same time point, LCN2-MMP9 can be elevated when LCN2 is within the normal range. An elevation of either [LCN2] or [LCN2-MMP9] is indicative of active inflammation.

TABLE 15

| LCN2 and LCN2-MMP9 levels from male r-axSpA patients without inflammatory bowel disease (IBD). | | | |
|---|---|---|---|
| Case # | LCN2 <150 ng/ml | LCN2-MMP9 <100 ng/ml | Notes |
| Case 62 | 138 | 172 | |
| Case 253 | 119 | 159 | |
| Case 424 | 99 | 177 | |
| Case 247 | 163 | 232 | Borderline elevated LCN2 |

Example 11: LCN2-MMP9:LCN2 Ratios Predicting Risk of Spondyloarthritis Development Introduction When [LCN2]:[LCN2-MMP9]=1±0.2, axial spondyloarthritis at least is unstable. Disease instability means inflammation levels are likely to fluctuate overtime irrespective of current therapy. This is the situation even when [LCN2]:[LCN2-MMP9]=1 and [LCN2], [LCN2-MMP9] are within normal limits.

Definitions of terms used in Table 16 as follows:

[L] serum LCN2 monomer, homodimer, ng/ml;

[LM] serum LCN2-MMP9 heterodimer, ng/ml;

i[LM] initial concentration of LCN2-MMP9 on first clinical presentation;

[L]=[LM] initial concentrations identical within 20%;

[L]>[LM] initial concentrations >20% difference;

Upper limit of normal (definition), serum analytes:

[L]=150 ng/ml;

[LM]=100 ng/ml

Response categories in Table 16, assessed by [L] only, as follows:

L: [L]<150 ng/ml at each time point. Same as CL Constant Low;

N: [L]>150 ng/ml initially, <150 ng/ml at most recent time point. Normalization;

F: [L] initially at any level. If <150 ng/ml, rises then decreases to <150 ng/ml and rises again. At most recent sample >150 ng/ml is categorized as "Fluctuating"

H: [L] initially >150 ng/ml and remains elevated at subsequent time points. Same as CH, constant high;

In the above definitions, cases that fluctuate in serial determinations in the N and H categories are ignored. However, some cases in each of these categories do fluctuate.

f is a broader definition of fluctuation that includes cases in N, F, H categories that fluctuate but at time of most recent serum sample, analytes remain elevated.

Fluctuation is an index of instability or periodicity of disease activity as many of these cases occur without a change in therapy.

Cases that fluctuate can have [L] [LM], whereas cases that do not fluctuate usually have [L]>[LM]. This is the situation even in cases where i[LM] is low. Although not all cases that fluctuate have [L]=[LM], when [L]=[LM] is seen initially these cases are likely to fluctuate.

Results and Discussion

Table 16 shows summary of serum concentrations of LCN2 and LCN2-MMP9 in r-axSpA and nr-axSpA patients, showing statistics on concentration of serum LCN2 and LCN2-MMP9 by [L]=[LM] and [L]>[LM]. The study set has 281 patients, of which 184 have r-axSpA and 87 have nr-axSpA, with serial analytes available.

TABLE 16

Summary of serum concentrations of LCN2 and LCN2-MMP9 in r-axSpA and nr-axSpA patients.

| i[LM] | <50 n | 51-100 n | 101-200 n | >200 n | Total n |
|---|---|---|---|---|---|
| L | | | | | |
| [L] > [LM] | 49 | 34 | 0 | 0 | 83 |
| [L] = [LM] | 0 | 0 | 0 | 0 | 0 |
| N | | | | | |
| [L] > [LM] | 3 | 19 | 27 | 3 | 52 |
| [L] = [LM] | 0 | 0 | 5 (1 f) | 10 (4 f) | 15 (5 f) |
| F | | | | | |
| [L] > [LM] | 7 | 17 | 27 | 9 | 60 (60 f) |
| [L] = [LM] | 4 | 2 | 16 | 12 | 34 (34 f) |
| H | | | | | |
| [L] > [LM] | 0 | 0 | 5 | 19 | 24 (12 f) |
| [L] = [LM] | 0 | 0 | 3 | 10 | 13 (3 f) |
| Total | | | | | |
| [L] > [LM] | 59 | 70 | 59 | 31 | 219 |
| [L] = [LM] | 4 | 2 | 24 | 32 | 62 |
| Grand Total | 63 | 72 | 839 | 63 | 281 |

The following observations are made about the results shown in Table 16:

[L] [LM] is present in 624281(22%) of cases.

[L] [LM] is present in 0/83 L (Low) cases.

[L]=[LM] is present in 34/90 of F (Fluctuation) cases.

[L]=[LM] is present in 6/136 i[LM] cases <100, all 6 of which the in F (Fluctuation) category.

Fluctuation (f) is detected in 5/13 N cases and 15/37 H cases as well as 94/94 F cases.

[L]=[LM] is present in 25 non F cases (10 N, 15H) total cases.

[L]=[LM] is present in 10/15 N cases, with no fluctuation.

These results may reasonably be interpreted to mean that these cases were intrinsically unstable cases that have been successfully treated.

Example 12: axSpA Patients have Elevated LCN2 (L and LCN2-MMP9 (LM) Levels

Methods

Patients:

It was shown in Example 1 that 69% (197/286) of axSpA patients have elevated LCN2 levels and 62% (123/197) of them have single LCN2 pathway involvement. The instant Example and Examples 13-16 below focus on assessing the group of axSpA patients having elevated LCN2 (L) levels but no detectable OSM levels. This is mainly for minimizing complexity in data interpretation as there are some indications that there is interaction between the LCN2 associated and the OSM pathways. For analyzing this subgroup of OSM negative patients, L and LCN2-MMP9 (LM) levels from a single blood sample in 190 axSpA patients (123 radiographic and 67 non-radiographic axSpA) were measured. Different groups/subgroups of axSpA patients were used in separate assessments as specified in Examples 12-16. All patients assessed had serum banking and concurrent clinical parameters. Table 17 summarizes demographic features of this cohort.

TABLE 17

Demographics of axSpA patients with LCN2-associated pathway involvement.

| | | axSpA patients (OSM negative) | | | |
|---|---|---|---|---|---|
| | | B27+ | | B27− | |
| | | n (%) | no comorbidities | n (%) | no comorbidities |
| nr-axSpA (n = 67) | M (n = 29) | 23 (79) | 13/23 | 6 (21) | 5/6 |
| | F (n = 38) | 26 (68) | 17/26 | 12 (32) | 7/12 |
| r-axSpA (n = 123) | M (n = 94) | 72 (77) | 39/72 | 22 (23) | 14/22 |
| | F (n = 29) | 19 (66) | 10/19 | 10 (34) | 9/10 |

Study Approval:

The study was approved by University Health Network (UHN) research ethics committee. All participating patients provided written informed consent, which was received from participants prior to inclusion in the study. Participants were identified by study number in the analyses.

MRI and Radiographic Damage Scoring:

Among patients who had MRI assessments, 29 of them were used for association analysis. Spondyloarthritis Research Consortium of Canada (SPARCC) scoring and Berlin spinal joint scoring (Maksymowych W P et al, 2005a; Maksymowych W P et al, 2005b; Hededal P et al, 2018) were evaluated. Scoring was done independently by two readers. The mean scores were used for correlation analysis with L or LM levels (Pearson's correlation and Spearman's Rho [nonparametric] correlation). MRI taken within 12 months of the time of biomarker measurements were used for this analysis.

Radiographic damage was assessed by the modified Stoke Ankylosing Spondylitis Spinal Score (mSASSS) (Maksymowych W P et al, 2014). mSASSS at the time of biomarker measurements were used for correlation analysis. Comparisons of biomarkers levels were made between 54 male vs 22 female r-axSpA patients with mSASSS<10. For correlation analysis of B27+ male r-axSpA patients, 32 with mSASSS>11 and 16 with mSASSS<10 were used.

Quantification of Serum LCN2, LCN2-MMP9, and OSM Levels:

The samples (stored at −70° C.) from each patient were thawed and analyzed at the same time to minimize assessment variabilities. L and LM levels were measured by sandwich ELISA according to manufacturer's protocol (LCN2 ELISA kit: R & D Systems, DLCN20; human MMP9/NGAL complex kit: R & D Systems, DY8556). The mean minimum detectable limit for human LCN2 and LCN2-MMP9 was 0.012 ng/ml and 0.013 ng/ml respectively (R & D Systems). The LCN2 kit showed no cross reactivity with human MMP9 and does not measure LCN2 hetero-complexes. The LCN2-MMP9 kit exhibited no cross reactivity with LCN2 monomers or homodimers. Same as in Examples 1 and 10, 150 ng/ml was used as a cut-off for LCN2 (as determined by mean+2SD of healthy controls). The cut-off for LM is 100 ng/ml. The low cut off used for OSM is "undetectable level".

Results

Examples above show that axSpA patients have pathological involvement of two pathways (LCN2 associated and OSM), acting singly or in combination. About 60% of axSpA patients have LCN2 involvement only. The instant Example focused on analyzing this subgroup with undetectable OSM in the circulation. Comparisons between the LCN2 (L) vs LCN2-MMP9 (LM) levels were made from a single blood sample in 190 axSpA patients (123 radiographic and 67 non-radiographic axSpA; FIG. 10). The cut-offs for L and LM are 150 ng/ml and 100 ng/ml, respectively. Overall, the L and LM level of this subgroup is 187 ng/ml±5 and 124 ng/ml±6, respectively. 52% (98/190) of the patients are L+LM+ concurrently. 22% (42/190) are L+, but with normal LM levels. 6% (11/190) are LM+, but with normal L levels. 21% (39/190) have normal levels of both L and LM (LnLMn).

Example 13: Correlation of LM Levels with MRI Scores in axSpA Patients

It was shown in Example 7 that elevated L levels are correlated significantly with MRI SPARCC SIJ scores in axSpA patients. In the instant Example, whether both L+ and LM+ levels reflect joint inflammation in axSpA patients was assessed. Comparisons of L and LM levels in L+LM+ axSpA patients (n=16) vs LnLMn patients with normal L and LM levels (n=13) with MRI SPARCC SIJ and Berlin Spine scores were made. Both L and LM levels correlate significantly with MRI SPARCC SIJ scores. In both cases, p-values of Pearson's r are 0.0004 (n=29, FIG. 11A; and n=29, FIG. 11B). For correlation with MRI Berlin Spinal scores, significant correlation is found with LM but not L levels, using Pearson's r correlation (n=29; p-value=0.004 for LM levels and p-value=0.28 for L levels; FIG. 11A for LM correlations and FIG. 11B for L correlations). However, using nonparametric Spearman's rho correlation, both LM and L levels had significant correlation with MRI Berlin Spinal scores. The correlation is more robust with LM levels (n=29; p-value=0.0003) vs 0.003 for L levels (FIG. 11A and FIG. 11B). Thus, compared to L levels, LM is a more robust indicator of spinal joint inflammation.

As controls, whether there is any correlation of L levels in L+ patients (n=8) compared to Ln patients (n=13) was assessed. No correlation is found in this comparison for both MRI SPARCC SIJ scores (Pearson's correlation coefficient=0.32, p=0.16) and MRI Berlin Spinal scores (Pearson's correlation coefficient=0.21, p=0.37;). L+ patients have lower L levels (n=8, 169 ng/ml±8) compared to L+LM+ patients (n=16, 235 ng/ml±21; one-way ANOVA p<0.00001; Tukey Honestly Significant Difference test p=0.03 between L+LM+ and L+, and p=0.02 between L+ and Ln [n=13]; FIG. 11C). In addition, L+ patients have low MRI scores and thus might explain why no correlation is found.

There were too few LM+ patients (<3) with MRI scores to address similar correlations. Taken together, higher L and LM levels in L+LM+ patients are associated with SIJ and spinal inflammation. This observation shows that L+LM+ patients have more severe SIJ and spinal inflammation.

Example 14: Gender Differences in r-axSpA Patients with Minimal Spinal Ankylosis (mSASSS<10)

This Example assessed the role of LM in joint inflammation. As there were more r-axSpA patients in this cohort, a subgroup of these patients with minimal ankylosis was selected to avoid complication of data interpretation for distinguishing the potential role of LM in ankylosis. While male (M) and female (F) r-axSpA patients have similarly elevated L levels (184 ng/ml±7 vs 193 ng/ml±10, M [n=54] vs F [n=22] respectively), female patients have significantly lower LM levels compared to male patients (141 ng/ml±8 for male vs 99 ng/ml±9 for female patients; p-value=0.03; FIG. 12A).

Profiling of the prevalence of L+, LM+ L+LM+ patients also revealed gender differences. 65% male patients (35/54) are L+LM+, while 64% (14/22) female patients are L+ ($chi^2$=16.6, p-value=0.00025; Table 18 and FIG. 12B). Higher L and LM levels are found in male r-axSpA L+LM+ patients with no ankylosis, compared to L+ or LM+ male patients (FIG. 12C). L levels in L+LM+ patients (n=35) are 207 ng/ml±9. This is significantly higher than L levels in L+ patients (n=9; 165 ng/ml±7; one-way ANOVA p<0.00001, Tukey Honestly Significant Difference p=0.05; FIG. 12C). Similarly, higher LM levels are present in L+LM+ patients (n=35, 166 ng/ml±9) vs LM+ patients (n=10; 122 ng/ml±8; one-way ANOVA p<0.00001, Tukey Honestly Significant Difference p=0.04; FIG. 12C). In female patients, there is also significant L level differences in L+LM+ patients (n=7; 232 ng/ml±25) vs L+ patients (n=14; 177 ng/ml±5; one-way ANOVA p<0.006, Tukey Honestly Significant Difference p=0.02; FIG. 12D). The L levels in female L+LM+ patients are also higher than L levels in male L+ patients (232 ng/ml±25 vs 165 ng/ml±7, respectively; p=0.004; FIG. 12D).

TABLE 18

Gender differences in LCN2 (L) and LCN2-MMP9 (LM) patterns in r-axSpA patients with mSASSS < 10 r-axSpA patients (mSASSS < 10)

| | L+LM+ (n) | L+ (n) | LM+ (n) | $chi^2$ (p-value) |
|---|---|---|---|---|
| Male (M) | 35 | 9 | 10 | |
| Female (F) | 7 | 14 | 1 | |
| | | | | 16.6 (0.00025) |

In view of this gender difference of 65% vs 30% L+LM+ in male vs female patients, respectively, and 17% vs 64% L+ in male vs female patients, respectively, concurrently higher L+ and LM+ levels are shown to be related to enhance spinal ankylosis progression. As female patients have lower LM levels, this explains a longtime clinical observation that there are fewer female patients with spinal ankylosis compared to male patients.

Example 15: B27 Positivity Related Differences in r-axSpA Male Patients

Aside from the observation that spinal ankylosis is more prevalent in male r-axSpA patients compared to female patients (Tournadre A et al, 2013), it has also been known for decades that B27 positive (B27+) male patients have more severe spinal radiographic progression and worse spinal mobility (Hededal P et al, 2018). The current cohort has too few female r-axSpA patients (less than 30) to assess this issue in detail and thus the instant Example is focused on male r-axSpA patients. As it was shown that both L and LM levels correlated to MRI SPARCC SIJ and Berlin Spine Scores, whether elevated L/LM levels might also reflect spinal radiographic progression in male r-axSpA patients was assessed. For this analysis, the cohort has 48 B27-positive (B27+) and 20 B27-negative (B27−) male r-axSpA patients; 67% (32/48) and 40% (8/20) respectively have mSASSS>11 ($chi^2$ 4.1; p=0.04).

There are significant differences in the elevated L vs LM profiles between B27+ vs B27− patients (FIG. 13A and FIG. 13B). Higher L and LM levels are present in B27+ compared to B27− patients (B27+ vs B27−: L levels; 242 ng/ml±10 vs 192 ng/ml±12, p=0.002; LM levels; 190 ng/ml±12 vs 102 ng/ml±13, p=0.00005; Student's t-test; Table 19).

TABLE 19

Comparison between B27+ and B27− male r-axSpA patients.

| | B27+ | B27− | t-test p value |
|---|---|---|---|
| n | 48 | 20 | |
| L Levels | 242 ± 10 | 192 ± 12 | 0.002** |
| LM Levels | 190 ± 12 | 102 ± 13 | 0.00005**** |

Profiling was carried out in B27+ vs B27− patients, both separately in two subgroups based on the status of spinal ankylosis (mSASSS <10 vs mSASSS >11). For B27+ patients, irrespective of spinal ankylosis status, most of them are L+LM+ patients (94% [15/16] vs 88% [28/32] for mSASSS<10 vs mSASSS>11 patients, respectively). In these two patient subgroups, significantly higher L and LM levels are present in mSASSS>11 patients (L levels: 263 ng/ml±15 vs 203 ng/ml±8, p=0.004; LM levels: 232 ng/ml±14 vs 157 ng/ml±12, p=0.0005; FIG. 14A). In contrast, for B27− patients, irrespective of spinal ankylosis status, L+ patients are prevalent (67% [8/12] vs 50% [4/8] for mSASSS<10 vs mSASSS>11 patients respectively). Elevation of L levels in mSASSS>11 patients are higher than those in mSASSS<10 patients (205 ng/ml±26 vs168 ng/ml±7, p=0.05; FIG. 14B).

65% (28/43) L+LM+B27+ male r-axSpA patient have higher L and LM levels when their mSASSS progressed to >11. Compared to B27+ patients, the prevalence of B27− L+LM+ patients is lower (50%, 4/8), and the LM levels overlap with patients with minimal spinal ankylosis (mSASSS<10), showing indirectly that higher LM levels likely facilitate spinal radiographic progression.

Example 16: Correlation of L Vs LM Levels with Spinal Ankylosis in Male r-axSpA Patients Via Comparison of Patients without and with Spinal Ankylosis In Example 13, it was shown that in L+LM+ r-axSpA patients, significant correlation of MRI Berlin Spine score is robust with LM levels, indicating that elevated LM levels reflect spinal joint inflammation. Thus, whether LM levels correlate with spinal ankylosis in L+LM+B27+ male r-axSpA patients was examined. Comparisons between 15 L+LM+B27+ mSASSS<10 patients and 20 L+LM+B27+ patients with mSASSS 11-55 were made. Both L and LM levels (but not CRP) correlate with mSASS scores (Pearson's r 0.42 for L [p=0.013] and 0.5 for LM [p=0.002]; FIG. 15A).

As shown in Example 15, 60% (12/20; FIG. 14B) of B27− male r-axSpA patients are in the L+ category (i.e. with normal LM levels). Therefore, whether L levels in these patients correlate with mSASS scores was assessed. 33% (4/12) L+ patients have mSASSS >11 and their L levels correlate with mSASSS (Pearson's r 0.76, p=0.004; FIG. 15B). This observation shows that elevated L levels alone (in the absence of LM elevation) reflect likely both spinal inflammation and ankylosis. In this comparison, there is no correlation of CRP with mSASS scores.

Taken together, the more severe spinal radiographic damage observed in male B27+ r-axSpA patients could be explained by the cumulative effects of both L+ and LM+ on spinal inflammation and ankylosis. However, it is difficult to distinguish whether L+ and LM+ levels in r-axSpA patients with ankylosis truly reflect the degree of spinal ankylosis or merely reflect the extent of spinal inflammation at different stages of radiographic progression.

In general, experience shows that B27− female r-axSpA patients usually have a milder disease course. Whether there is an additive effect in B27 positivity and sex was assessed by comparing B27+ male vs B27+ female patients in their L/LM pattern profiles. For mSASSS <10 male patients, 15 are L+LM+ and only one L+. For mSASSS >11 male patients, there are 28 L+LM+ and 4 L+. In contrast, for mSASSS<10 female patients, 5 of them are L+LM+ vs 6 L+. There are only 1 L+LM+ and 1 L+ female patients with mSASSS>11. There is a significant gender difference in the profiles of these B27 positive patients (Pearson's $chi^2$=23, p<0.00004; Table 20), indicating an additive effect of B27 positivity and maleness. L+LM+ is the predominant pattern irrespective of mSASSS status in the B27+ male r-axSpA patients, indicating that the additive effect of B27 positivity and maleness likely occurs prior to spinal ankylosis progression.

TABLE 20

Additive effect of HLA-B27 positivity and maleness in r-axSpA patients.

| | mSASSS < 10 | | mSASSS > 11 | | |
|---|---|---|---|---|---|
| B27+ r-axSpA | L + LM+ (n) | L+ (n) | L + LM+ (n) | L+ (n) | $chi^2$ (p-value) |
| M | 15 | 1 | 28 | 4 | |
| F | 5 | 6 | 1 | 1 | |
| | | | | | 23 (0.00004) |

As spinal inflammation could subside in patients with near fused spines (mSASSS 56-72), comparisons between 8 L+LM+B27+ patients with mSASSS 56-72 and 15 L+LM+ B27+ mSASSS<10 patients were made. L levels remain correlated with mSASSS (Pearson's r 0.48, p=0.02; FIG. 16A); but LM levels no longer correlate with mSASSS (Pearson's r 0.35, p=0.1; FIG. 16A). This observation shows that joint inflammation in patients with near fused spine is likely due to L but not LM elevation.

In this cohort, there are 2 male B27+ r-axSpA patients with completely fused spine (mSASSS 72), and sequential L/LM measurements are available post spinal fusion for up to 12 years. For both patients, during this long follow-up period, LM levels remain normal, but there were fluctuating elevations of L levels despite continual biologics treatments (FIG. 16B). This observation shows that elevation of L exists throughout the disease course irrespective of ankylosis status; and thus L elevation mainly reflect joint inflammation in male r-axSpA patients.

Elevation of LM levels is more prominent in male B27+ r-axSpA patients during spinal radiographic progression as MRI data show that LM levels reflect spinal inflammation more robustly than elevated L levels (FIG. 11A and FIG. 11B). FIG. 17 shows a schematic of this perspective. The thickness of the bars indicates the intensities of inflammation during the disease course of male B27+ vs B27− r-axSpA patients. FIG. 18 shows a model of a perspective for r-axSpA development based on these data.

Example 17: OSM (O) Positivity is Associated with Lower LCN2 (L) & LCN2-MMP9 (LM) Levels in B27 Positive Male r-axSpA Patients It was shown in Example 1 that axSpA patients have pathological involvement of two pathways (LCN2 associated and OSM) acting singly or in combination. About 26% of axSpA patients have involvement of both pathways. Whether there is any interactions between the two pathways in this group of patients was assessed. As it was also shown in Examples 14-16 that there are gender and B27 status differences in L and LM elevated levels, whether there is any relationship between elevated O vs L/LM levels in B27+ male r-axSpA patients was assessed. The L vs LM levels from a single blood sample in 126 B27+ male r-axSpA patients were compared. 72 of these patients are OSM− (black dots; FIG. 19A) and 54 are OSM+ (43%, gray dots; FIG. 19A). The cut-offs for L and LM were the same as in Examples 1, 10 and 12, namely 150 ng/ml and 100 ng/ml, respectively. Both the L and the LM levels are significantly lower in OSM+ patients (for OSM+ vs OSM− patients; L levels: 217 ng/ml±9 vs 159 ng/ml±12 respectively, p-value=0.00005; LM levels: 169 ng/ml±10 vs 103 ng/ml±10 respectively, p-value <0.00001; FIG. 19A). Thus, OSM positivity is associated with lower L and LM levels in B27+ male r-axSpA patients.

To assess whether this association is coincidental, whether similar association is present in patients with 2 consecutive samples in which one sample is OSM− and the other is OSM+ was examined. There are 8 patients (mSASSS<10 in patients 1-4 and mSASSS>11 in patients 5-8) with these measurements (FIG. 19B). As in the single sample analysis, OSM positivity is associated with lower L and LM levels (For OSM+ vs OSM− samples; L levels: 210 ng/ml±26 vs 119 ng/ml±16 respectively, p-value=0.005; LM levels: 151 ng/ml±38 vs 51 ng/ml±6 respectively, p-value=0.01; FIG. 19B).

These results show that OSM elevation in B27+ male r-axSpA patients correlates with lower L and LM levels throughout the disease course.

Among the 72 OSM− patients, 32 of them (44%) have mSASSS>11; while 31% (17/54) OSM+ patients have mSASSS>11. There is no significant difference in the prevalence of patients with mSASSS>11 irrespective of OSM status, even though OSM+ mSASSS>11 patients have significantly higher L and LM levels compared to the OSM− mSASSS>11 patients (L levels: 262 ng/ml±14 vs 162 ng/ml±17, respectively {p=0.00003}; LM levels: 205 ng/ml±16 vs 105 ng/ml±18, respectively {p=0.0001}; FIG. 19C). These results show that elevated OSM levels reflect joint inflammation despite their association of lower L/LM levels. Examples 2 and 7 documented correlations between OSM levels and MRI inflammatory scores in patients with a persistently elevated OSM level, even though they have normal L/LM levels.

Example 18: OSM Positivity is Associated with Lower LCN2 Levels in B27 Negative Male r-axSDA Patients Example 15 showed that B27− OSM− male r-axSpA patients have significantly lower LM levels than their B27+ OSM− counterparts (Table 19: 102 ng/ml±13 vs 190 ng/ml±12 respectively; p-value=0.00005). Whether there are any differences in OSM interactions relating to B27 status of the patients was therefore assessed. L vs LM levels were compared in B27− OSM− (n=21) vs B27− OSM+ (n=20) male r-axSpA patients. Different from B27+ patients, OSM+ is associated with lower L levels compared to OSM− (139 ng/ml±10 vs 187 ng/ml±9 respectively, p=0.0006). LM levels are not different (101 ng/ml±14 vs 100 ng/ml±13 respectively, p=0.48; FIG. 20A).

Comparison of OSM levels in B27+ vs B27− male r-axSpA patients showed that OSM+B27− patients (n=20) have significantly higher OSM levels compared to OSM+ B27+ patients (n=54; O levels: 730 pg/ml±211 vs 379 pg/ml±72 respectively, p=0.02). In B27− OSM+ patients, LM (but not L) levels correlate with OSM levels (Pearson's r correlations: p-value=0.0009 for LM levels and p-value=0.7 for L levels; FIG. 20B). It has been reported that OSM together with interleukin 1 upregulate MMP9 particularly in chondrocytes (Gilbert S J et al. 2012). The present results show that in B27− male r-axSpA patients, the correlation of OSM with LM levels is due to increased MMP9 availability consequent to OSM induction. In B27+ r-axSpA male patients, there is no correlation between OSM and L/LM levels, likely due to masking by other covariates in the B27+ patients.

There are 5 main patterns of biomarkers which reflect joint inflammation: two in OSM− patients: L+LM+ and L+; and three in OSM+ patients: L+LM+O+, L+O+ and LnLMnO+. The profile of these 5 patterns differs significantly in B27+ vs B27− male r-axSpA patients (Pearson's chi$^2$=20.5; p=0.0004; Table 21).

TABLE 21

Profile of LCN2, LCN2/MMP9, and OSM expression patterns differ between B27+ and B27− male r-axSpA patients.

| r-axSpA | OSM −ve | | OSM +ve | | | Chi² |
|---|---|---|---|---|---|---|
| (male) | L + LM+ | L+ | L + LM + O+ | L + O+ | LnLMnO+ | (p-value) |
| B27 −ve (n = 35) | 8 | 11 | 6 | 2 | 8 | |
| B27 +ve (n = 114) | 56 | 6 | 22 | 7 | 23 | |
| | | | | | | 20.5 (0.0004) |

Taken together, these observations show OSM being protective (via lowering L/LM levels) especially in B27+ male r-axSpA patients. However, persistently elevated OSM by itself (even when L/LM levels are normal) reflects mainly SIJ inflammation (MRI data reported in Examples 2 and 7, above).

There are no differences in the L/LM levels when comparing OSM− vs OSM+ female axSpA patients (both r- and nr-) and male nr-axSpA patients.

CITATIONS FOR REFERENCES REFERRED TO IN THE SPECIFICATION

Abella V, Scotece M, Conde J, Gómez R, Lois A, Pino J et al. The potential of lipocalin-2/NGAL as biomarker for inflammatory and metabolic diseases. Biomarkers. 2015 December; 20(8):565-71.

Argollo M C, Allocca M, Furfaro F, Peyrin-Biroulet L, Danese S. Interleukin-23 blockers: Born to be first-line biologic agents in inflammatory bowel disease? Curr Pharm Des. 2019; 25(1):25-31. Available from: doi: 10.2174/1381612825666190313140811.

Ataseven A, Kesli R, Kurtipek G S, Ozturk P. Assessment of lipocalin 2, clusterin, soluble tumor necrosis factor receptor-1, interleukin-6, homocysteine, and uric acid levels in patients with psoriasis. *Dis Markers* 2014 April; 541709. Available from: doi: 10.1155/2014/541709.

Bandinelli F, Manetti M, Ibba-Manneschi L. Occult spondyloarthritis in inflammatory bowel disease. Clin Rheumatol. 2016 February; 35(2):281-9. Available from: doi: 10.1007/s10067-015-3074-z.

Benhamou M, Gossec L, Dougados M. Clinical relevance of C reactive protein in ankylosing spondylitis and evaluation of the NSAIDs/cyclo-oxygenase-2 inhibitors' treatment effect on C reactive protein. *Rheumatology.* 2010 March; 49(3):536-41.

Braun J, Baraliakos X, Deodhar A, Baeten D, Sieper J, Emery P, et al. Effect of secukinumab on clinical and radiographic outcomes in ankylosing spondylitis: 2-year results from the randomised phase Ill MEASURE 1 study. Ann Rheum Dis. 2017 June; 76(6):1070-7. Available from: doi:10.1136/annrheumdis-2016-209730

Brown M A, Li Z, Cao K L. Biomarker development for axial spondyloarthritis. *Nat Rev Rheumatol.* 2020 August; 16(10):448-63.

Chan J, Sari I, Salonen D, Silverberg M S, Haroon N, Inman R D. Prevalence of sacroiliitis in inflammatory bowel disease using a standardized computed tomography scoring system. Arthritis Care Res. 2018 May; 70(5):807-10. Available from: doi: 10.1002/acr.23323.

Ciccia F, Rizzo A, Triolo G. Subclinical gut inflammation in ankylosing spondylitis. Curr Opin Rheumatol. 2016 January; 28(1):89-96.

Conde J, Otero M, Scotece M, Abella V, L6pez V, Pino J, et al. E74-like factor 3 and nuclear factor-κB regulate lipocalin-2 expression in chondrocytes. *J Physiol.* 2016 November; 594(21):6133-46.

Cuvelier C, Barbatis C, Mielants H, De Vos M, Roels H, Veys E. Histopathology of intestinal inflammation related to reactive arthritis. Gut 1987 April; 28(4):394-401.

Cuvelier C A, Mielants H, Ouatacker J, De Vos M, Veys E, Roels H. Immunopathogenetic mechanisms in spondylarthropathy and gut inflammation. Adv Exp Med Biol. 1995; 371B:1379-80.

Davies S C, Nguyen T M, Parker C E, MacDonald J K, Jairath V, Khanna R, et al. Anti-IL-12/23p40 antibodies for maintenance of remission in Crohn's disease. Cochrane Database Syst Rev. 2019 December; 12(12): CD012804. Available from: doi: 10.1002/14651858.CD012804.pub2.

Dakwar E, Reddy J, Vale F L, Uribe J S. A review of the pathogenesis of ankylosing spondylitis. Neurosurg Focus 2008; 24(1):E2. Available from: doi: 10.3171/FOC/2008/24/1/E2.

de Bruyn M, Arijs I, Wollants W J, Machiels K, Van Steen K, Van Assche G, et al. Neutrophil gelatinase B-associated lipocalin and matrix metalloproteinase-9 complex as a surrogate serum marker of mucosal healing in ulcerative colitis. Inflamm Bowel Dis. 2014 July; 20(7):1198-207.

de Bruyn M, Arijs I, De Hertogh G, Ferrante M, Van Assche G, Rutgeerts P, et al. Serum neutrophil gelatinase B-associated lipocalin and matrix metalloproteinase-9 complex as a surrogate marker for mucosal healing in patients with Crohn's disease. J Crohns Colitis. 2015 December; 9(12):1079-87.

De Vries M K, van Eijk I C, van der Horst-Bruinsma I D, Peters MJL, Nurmohamed M T, Dijkmans BAC, et al. Erythrocyte sedimentation rate, C reactive protein level, and serum amyloid a protein for patient selection and monitoring of anti-tumor necrosis factortreatment in ankylosing spondylitis. Arthritis Rheum 2009 November; 61(11):1484-90.

Ellinghaus D, Jostins L, Spain S L, Cortes A, Bethune J, Han B, et al. Analysis of five chronic inflammatory diseases identifies 27 new associations and highlights disease-specific patterns at shared loci. Nat Genet. 2016 May; 48(5):510-8.

Fernández C A, Yan L, Louis G, Yang J, Kutok J L, Moses M A. The matrix metalloproteinase-9/neutrophil gelatin associated lipocalin complex plays a role in breast tumor growth and is present in the urine of breast cancer patients. Clin Cancer Res. 2005 August; 11(15):5390-5.

Garrett S, Jenkinson T, Kennedy G, Whitelock H, Gaisford P, Calin A. A new approach to defining disease status in ankylosing spondylitis: The Bath Ankylosing Spondylitis Disease Activity Index. J Rheumatol. 1994 December; 21(12): 2286-91.

Gilbert S J, Blain E J, A I-Sabah A, Zhang Y, Duance V C, Mason D J. Protein kinase R plays a pivotal role in oncostatin M and inteleukin-1 signalling in bovine articular cartilage chondrocytes. Eur Cell Mater. 2012 January; 23:41-57.

Glintborg B, Østergaard M, Krogh N S, Tarp U, Manilo N, Loft A G, et al. Clinical response, drug survival and predictors thereof in 432 ankylosing spondylitis patients after switching tumour necrosis factor α inhibitor therapy: results from the Danish nationwide DANBIO registry. Ann Rheum Dis 2013 July; 72(7):1149-55.

Gracey E, Qaiyum Z, Almaqhlouth I, Lawson D, Karki S, Avvaru N, et al. IL-7 primes IL-17 in mucosal-associated invariant T (MAIT) cells, which contribute to the Th17-axis in ankylosing spondylitis. Ann Rheum Dis. 2016 December; 75(12):2124-32.

Gupta K, Shukla M, Cowland J B, Malemud C J, Haqqi T M. Neutrophil gelatinase-associated lipocalin is expressed in osteoarthritis and forms a complex with matrix metalloproteinase 9. Arthritis Rheum. 2007 October; 56(10):3326-35.

Hededal P, Østergaard M, Sorensen I J, Loft A G, Hindrup J S, Thamsborg G, et al. Development and validation of MRI sacroiliac joint scoring methods for the semi axial scan plane corresponding to the Berlin and SPARCC MRI scoring methods, and of a new global MRI sacroiliac joint method. J Rheumatol. 2018 January; 45(1):70-7.

Jacques P, Elewaut D, Mielants H. Interaction between gut inflammation and arthritis/spondylitis. Curr Opin Rheumatol. 2010 July; 22(4):368-74.

Kelly O B, Li N, Smith M, Chan J, Inman R D, Silverberg M S. The prevalence and clinical associations of subclinical sacroiliitis in inflammatory bowel disease. Inflamm Bowel Dis. 2019 May; 25(6):1066-71.

Kerfoot S M, Raharjo E, Ho M, Kaur J, Serirom S, McCafferty D M, et al. Exclusive neutrophil recruitment with Oncostatin M in a human system. Am J Pathol. 2001 October; 159(4):1531-9.

Kim T H, Uhm W S, Inman R D. Pathogenesis of ankylosing spondylitis and reactive arthritis. Curr Opin Rheumatol. 2005 July; 17(4):400-5.

Korkosz M, Czepiel M, Gula Z, Stec M, Weglarczyk K, Rutkowska-Zapala M, et al. Sera of patients with axial spondyloarthritis (axSpA) enhance osteoclastogenic potential of monocytes isolated from healthy individuals. BMC Musculoskelet Disord. 2018 December; 19(1):434. Available from: doi: 10.1186/s12891-018-2356-4.

Lin A, Inman R D, Streutker C K, Zhang Z, Pritzer KPH, Tsui H W, et al. Lipocalin 2 links inflammation and ankyloses in the clinical overlap of inflammatory bowel disease (IBD) and ankylosing spondylitis (AS). Arthritis Res Ther. 2020 March; 22(1):51. Available from: doi: 10.1186/s13075-020-02149-4.

Lu F, Inoue K, Kato J Minamishima S, Morisaki H. Functions and regulation of lipocalin-2 in gut-origin sepsis: a narrative review. Crit Care. 2019 August; 23(1):269-76.

Luyckx V A, Cairo L V, Compston C A, Phan W L, Mueller T F. Oncostatin M pathway plays a major role in the renal acuter phase response. Am J Physiol Renal Physiol. 2009 April; 296(4): F875-83.

Machado P, Landewe R, Lie E, Kvien T K, Braun J, Baker D, et al. Ankylosing Spondylitis Disease Activity Score (ASDAS): defining cut-of values for disease activity states and improvement scores. Ann Rheum Dis. 2011 January; 70(1):47-53.

Maksymowych W P, Inman R D, Salonen D, Dhillon S S, Williams M, Stone M, et al. Spondyloarthritis Research Consortium of Canada magnetic resonance imaging index for assessment of sacroiliac joint inflammation in ankylosing spondylitis. Arthritis Rheum. 2005a October; 53(5):703-9.

Maksymowych W P, Inman R D, Salonen D, Dhillon S S, Krishnananthan R, Stone M, et al. Spondyloarthritis Research Consortium of Canada magnetic resonance imaging index for assessment of spinal inflammation in ankylosing spondylitis. Arthritis Rheum. 2005bAug; 53(4):502-9.

Maksymowych W P, Learch R, Lambert R G, Ward M, Haroon N, Inman R, et al. Development and validation of the spondyloarthritis radiography module for calibration of readers using the modified stoke ankylosing spondylitis spine score. Arthritis Care Res. 2014 January; 66(1):55-62.

Manica S R, Baraliakos X, Nikiphorou E. Early Recognition and Treatment of Spondyloarthritis: A Timeless Challenge. EMJ Rheumatol. 2020; 7(1):72-9.

Moschen A R, Adolph T E, Gerner R R, Wieser V, Tilg H. Lipocalin-2: a master mediator of intestinal and metabolic inflammation. *Trends Endocrinol Metab.* 2017; 28:388-97.

Rudwaleit M, Baeten D. Ankylosing spondylitis and bowel disease. Best Pract Res Clin Rheumatol. 2006 June; 20(3):451-71.

Richards C D. The enigmatic cytokine oncostatin m and roles in disease. ISRN Inflamm. 2013 December; 512103. Available from: doi: 10.1155/2013/512103

Shen F, Hu Z, Goswami J, Gaffen S L. Identification of common transcriptional regulatory elements in interleukin-17 target genes. J Biol Chem. 2006 August; 281 (34):24138-48.

Sieper J, van der Heijde, Dougados M, Mease P J, Maksymowych W P, Brown M A, et al. Efficacy and safety of adalimumab in patients with non-radiographic axial spondyloarthritis: results of a randomised placebo-controlled trial (ABILITY-1). Ann Rheum Dis. 2013 June; 72(6): 815-22.

Singh V, Yeoh B S, Chassaing B, Zhang B, Saha P, Xiao X, et al. Microbiota-inducible innate immune, siderophore binding protein lipocalin 2 is critical for intestinal homeostasis. Cell Mol Gastroenterol Hepatol. 2016 July; 2(4): 482-98.

Song I H, Poddubnyy D A, Rudwaleit M, Sieper J. Benefits and risks of ankylosing spondylitis treatment with nonsteroidal anti-inflammatory drugs. Arthritis Rheum 2008 April; 58(4):929-38.

Sproston N R, Ashworth J J. Role of C-Reactive Protein at sites of inflammation and infection. Front Immunol. 2018 April; 9:754. Available from: doi: 10.3389/fimmu.2018.00754

Stallhofer J, Friedrich M, Konrad-Zerna A, Wetzke M, Lohse P, Glas J, et al. Lipocalin-2 is a disease activity marker in inflammatory bowel disease regulated by IL-17A, IL-22, and TNF-α and modulated by IL23R genotype status. Inflamm Bowel Dis. 2015 October; 21(10):2327-40.

Stone M A, Pomeroy E, Keat A, Sengupta R, Hickey S, Dieppe P, et al. Assessment of the impact of flares in ankylosing spondylitis disease activity using the Flare Illustration. Rheumatology. 2008 August; 47(8):1213-18.

Tournadre A, Pereira B, Lhoste A, Dubost J J, Ristori J M, Claudepierre P, et al. Differences between women and men with recent-onset axial spondyloarthritis: results from a prospective multicenter French cohort. Arthritis Care Res. 2013 September; 65(9):1482-9.Turina M C, Landewe R, Baeten D. Lessons to be learned from serum biomarkers in psoriasis and IBD—the potential role in SpA. Expert Rev Clin Immunol. 2017 April; 13(4):333-44.

van der Heijde D, Braun J, Deodhar A, Baraliakos X, Landewé R, Richards H B, et al. Modified stoke ankylosing spondylitis spinal score as an outcome measure to assess the impact of treatment on structural progression in ankylosing spondylitis. Rheumatology. 2019 March; 58(3):388-400.

Veeriah V, Zanniti A, Paone R, Chatterjee S, Rucci N, Teti A, et al. Interleukin-1β, lipocalin 2 and nitric oxide synthase 2 are mechano-responsive mediators of mouse and human endothelial cell-osteoblast crosstalk. Sci Rep. 2016 July; 6:29880. Available form: doi: 10.1038/srep29880

Verstockt B, Ferrante M, Vermeire S, Van Assche G. New treatment options for inflammatory bowel diseases. J Gastroenterol. 2018 May:53(5):585-90.

Verstockt S, Verstockt B, Vermeire S. Oncostatin M as a new diagnostic, prognostic and therapeutic target in inflammatory bowel disease (IBD). Expert Opin Ther Targets 2019 November; 23(11):943-54.

Walker E C, McGregor N E, Poulton I J, Solano M, Pompoli S, Fernandes T J, et al. Oncostatin M promotes bone formation independently of resorption when signaling through leukemia inhibitory factor receptor in mice. J Clin Invest. 2010 February; 120(2): 582-92.

Wang Q, Li S, Tang X, Liang L, Wang F, Du H. Lipocalin 2 protects against *Escherichia coli* infection by modulating neutrophil and macrophage function. Front Immunol. 2019 November; 10:2594. Available from: doi: 10.3389/fimmu.2019.02594

West N R, Owens B M J, Hegazy A N. The oncostatin M-stromal cell axis in health and disease. Scand J Immunol. 2018 September; 88(3):e12694. Available from: doi: 10.1111/sji.12694.

Wu Q, Inman R D, Davis K D. Tumor necrosis factor inhibitor therapy in ankylosing spondylitis: differential effects on pain and fatigue and brain correlates. Pain 2015 February:156(2):297-304.

Xu M J, Feng D, Wu H, Wang H, Chan Y, Kolls J, et al. The liver is the major source of elevated serum lipocalin-2 levels after bacterial infection or partial hepatectomy: a critical role for IL-6/STATs. Hepatology. 2015 February; 61(2):692-702.

Yan L, Borregaard N, Kjeldsen L, Moses M A. The high molecular weight urinary matrix metalloproteinase (MMP) activity is a complex of gelatinase B/MMP-9 and neutrophil gelatinase-associated lipocalin (NGAL). Modulation of MMP-9 activity by NGAL. J Biol Chem. 2001 October; 276(40):37258-65.

The invention claimed is:

1. A method of treating a subject with a chronic inflammatory disease, optionally axial spondyloarthritis, the method comprising:

a) administering to the subject a suitable treatment, optionally an anti-inflammatory therapy, an anti-inflammatory agent, an anti-fibrotic therapy, or an anti-fibrotic agent, when a sample from the subject exhibits a lipocalin 2 (LCN2) and LCN2-Matrix metallopeptidase 9 heterodimer (LCN2-MMP9), and optionally oncostatin M (OSM) elevation compared to a previous sample and/or one or more reference profiles; or b) i) monitoring clinical disease activity, treatment response, disease progression, and/or active repair in the subject by measuring in vitro a level of lipocalin2 (LCN2) and a level of LCN2-Matrix metallopeptidase 9 heterodimer (LCN2-MMP9), and optionally a level of oncostatin M (OSM) in a sample obtained from the subject; and comparing the measured level of LCN2 and LCN2-MMP9, and optionally OSM to level in a previous sample and/or one or more reference profiles;

wherein a differential in the measured level of LCN2 and LCN2-MMP9, and optionally OSM compared to the previous sample or a differential in the measured level of LCN2 and LCN2-MMP9, and optionally OSM compared to the one or more reference profile of the measured level of LCN2 and LCN2-MMP9, and optionally OSM similar to the one or more reference profile, is indicative of clinical disease activity, disease progression, treatment response, active repair, and/or risk of developing a disease; and ii) administering to the subject a suitable treatment, optionally an anti-inflammatory therapy, an anti-inflammatory agent, an anti-fibrotic therapy, or an anti-fibrotic agent, when a sample from the subject exhibits an LCN2 and LCN2-MMP9, and optionally OSM elevation compared to a previous sample and/or one or more reference profiles, optionally wherein the suitable treatment, optionally an inflammatory agent, is administered until the level of LCN2 and LCN2-MMP9, and optionally OSM is decreased or about normal, optionally wherein the subject is also afflicted with inflammatory bowel disease.

2. The method of claim 1, wherein the suitable treatment is an anti-inflammatory agent optionally wherein the anti-inflammatory agent is or comprises a nonsteroidal anti-inflammatory drug (NSAID), a disease modifying anti-rheumatic drug (DMARD), a tumor necrosis factor alpha (TNF-alpha) inhibitor, and/or an interleukin 17 inhibitor, optionally the interleukin 17 inhibitor is secukinumab, or wherein the suitable treatment is an anti-inflammatory agent optionally wherein the anti-inflammatory agent is or comprises a tumor necrosis factor alpha (TNF-alpha) inhibitor, optionally the TNF-alpha inhibitor comprises adalimumab, certolizumab, etanercept, golimumab, infliximab, or a combination thereof, optionally when the sample exhibits elevated level of LCN2, or elevated level of LCN2 and LCN2-MMP9, or elevated level of LCN2, LCN2-MMP9 and OSM compared to a previous sample and/or one or more reference profiles, or wherein the anti-inflammatory agent lacks a TNF-alpha inhibitor, optionally the subject was previously receiving a TNF alpha inhibitor, or wherein the suitable treatment is an anti-fibrotic agent, optionally the anti-fibrotic agent is or comprises nintedanib or pirfenidone.

3. The method of claim 1, wherein the sample exhibits LCN2normal persistent increased OSM and the subject is receiving anti-inflammatory treatment and the administering comprises administering an increased dosage of the anti-inflammatory agent or the anti-inflammatory agent administered is different from the anti-inflammatory treatment.

4. The method of claim 1, wherein the chronic inflammatory disease is axSpA, and wherein a good treatment response comprises improvement or resolve of inflammatory back pain, SIJ inflammation, persistent pain, and/or pain flare up frequency or intensity.

5. The method of claim 1, wherein the sample is a blood, serum, or plasma sample.

6. The method of claim 1, wherein the level of LCN2 and LCN2-MMP9, and optionally OSM, is measured by enzyme-linked immunosorbent assay (ELISA).

7. The method of claim 1, wherein the sample exhibits a weight ratio of concentration of LCN2 to concentration of LCN2-MMP9 less than about 1:1.

8. The method of claim 1, wherein the subject has axial spondyloarthritis and inflammatory bowel disease.

9. The method of claim 1, wherein the administering comprises administering an increased dosage of the anti-inflammatory agent, or administering an anti-inflammatory agent different from a previously administered anti-inflammatory agent, when the sample exhibits persistent elevation of LCN2 and LCN2-MMP9 compared to a previous sample and/or one or more reference profiles.

* * * * *